US012758583B2

(12) United States Patent
Wen

(10) Patent No.: US 12,758,583 B2
(45) Date of Patent: Oct. 13, 2026

(54) TARGETABLE IMMUNE CHECKPOINT FOR IMMUNOTHERAPY

(71) Applicant: Ohio State Innovation Foundation, Columbus, OH (US)

(72) Inventor: Haitao Wen, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 841 days.

(21) Appl. No.: 18/153,426

(22) Filed: Jan. 12, 2023

(65) Prior Publication Data

US 2023/0338423 A1 Oct. 26, 2023

Related U.S. Application Data

(60) Provisional application No. 63/378,271, filed on Oct. 4, 2022, provisional application No. 63/336,502, filed on Apr. 29, 2022, provisional application No. 63/298,808, filed on Jan. 12, 2022.

(51) Int. Cl.

*A61K 35/17* (2025.01)
*A61P 35/00* (2006.01)
*C07K 16/28* (2006.01)

(52) U.S. Cl.

CPC .............. *A61K 35/17* (2013.01); *A61P 35/00* (2018.01); *C07K 16/2896* (2013.01)

(58) Field of Classification Search

None
See application file for complete search history.

(56) References Cited

PUBLICATIONS

Shi. Chimeric antigen receptor for adoptive immunotherapy of cancer: latest research and future prospects. Mol Cancer, 13(219): 1-8. (Year: 2014).*
Hematological Malignancies (https://hmrn.org/about/classification). (Year: 2021).*
Pan. CSBF/C10orf99, a novel potential cytokine, inhibits colon cancer cell growth through inducing G1 arrest. Sci Rep, 4(6812):1-10 and Supplementary Information p. 1-6. (Year: 2014).*
Zhang. Downregulation of endometrial mesenchymal marker SUSD2 causes cell senescence and cell death in endometrial carcinoma cells. PloS One; 12: e0183681. (Year: 2017).*
Zhao. Modulation of CD8 T cell antitumor function by an immune inhibitory molecule sushi domain containing 2. J Immunol, 206(1): Supplement p. 57.27. (Year: 2021).*
Schoenfeld, A.J. & Hellmann, M.D. Acquired Resistance to Immune Checkpoint Inhibitors. Cancer Cell 37, 443-455 (2020).
Binnewies, M., et al. Understanding the tumor immune microenvironment (TIME) for effective therapy. Nat Med 24, 541-550 (2018).
Altorki, N.K., et al. The lung microenvironment: an important regulator of tumour growth and metastasis. Nature reviews 19, 9-31 (2019).
Herbst, R.S., Morgensztern, D. & Boshoff, C. The biology and management of non-small cell lung cancer. Nature 553, 446-454 (2018).
Andrews, L.P., Yano, H. & Vignali, D.A.A. Inhibitory receptors and ligands beyond PD-1, PD-L1 and CTLA-4: breakthroughs or back-ups. Nat Immunol 20, 1425-1434 (2019).
Kalbasi, A. & Ribas, A. Tumour-intrinsic resistance to immune checkpoint blockade. NatRev Immunol 20, 25-39 (2020).
Leonard, W.J., Lin, J.X. & O'Shea, J.J. The gammac Family of Cytokines: Basic Biology to Therapeutic Ramifications. Immunity 50, 832-850 (2019).
Morgan, Doris Anne, Francis W. Ruscetti, and Robert Gallo. "Selective in vitro growth of T lymphocytes from normal human bone marrows." *Science* 193.4257 (1976): 1007-1008.
Pipkin, M.E., et al. Interleukin-2 and inflammation induce distinct transcriptional programs that promote the differentiation of effector cytolytic T cells. Immunity 32, 79-90 (2010).
Kalia, V., et al. Prolonged interleukin-2Ralpha expression on virus-specific CD8+ T cells favors terminal-effector differentiation in vivo. Immunity 32, 91-103 (2010).
Spolski, R., Li, P. & Leonard, W.J. Biology and regulation of IL-2: from molecular mechanisms to human therapy. Nat Rev Immunol 18, 648-659 (2018).
Boyman, O., Kovar, M., Rubinstein, M.P., Surh, C.D. & Sprent, J. Selective stimulation of T cell subsets with antibody-cytokine immune complexes. Science 311, 1924-1927 (2006).
Williams, M.A., Tyznik, A.J. & Bevan, M.J. Interleukin-2 signals during priming are required for secondary expansion of CD8+ memory T cells. Nature 441, 890-893 (2006).
Scott, E.N., Gocher, A.M., Workman, C.J. & Vignali, D.A.A. Regulatory T Cells: Barriers of Immune Infiltration Into the Tumor Microenvironment. Front Immunol 12, 702726 (2021).
Boyman, O. & Sprent, J. The role of interleukin-2 during homeostasis and activation of the immune system. Nat Rev Immunol 12, 180-190 (2012).
Wang, X., Rickert, M. & Garcia, K.C. Structure of the quaternary complex of interleukin-2 with its alpha, beta, and gammac receptors. Science 310, 1159-1163 (2005).
Rickert, M., Wang, X., Boulanger, M.J., Goriatcheva, N. & Garcia, K.C. The structure of interleukin-2 complexed with its alpha receptor. Science 308, 1477-1480 (2005).
Bachmann, M.F., Wolint, P., Walton, S., Schwarz, K. & Oxenius, A. Differential role of IL-2R signaling for CD8+ T cell responses in acute and chronic viral infections. Eur J Immunol 37, 1502-1512 (2007).
Sugahara, T., et al. Isolation of a novel mouse gene, mSVS-1/SUSD2, reversing tumorigenic phenotypes of cancer cells in vitro. Cancer Sci 98, 900-908 (2007).
Souri, M., Kaetsu, H. & Ichinose, A. Sushi domains in the B subunit of factor XIII responsible for oligomer assembly. Biochemistry 47, 8656-8664 (2008).

(Continued)

*Primary Examiner* — Maureen Varina Driscoll
(74) *Attorney, Agent, or Firm* — Meunier Carlin & Curfman LLC

(57) ABSTRACT

The present disclosure relates to the field of T cell-based immunotherapy to promote anticancer effector functions.

21 Claims, 80 Drawing Sheets

Specification includes a Sequence Listing.

(56) References Cited

PUBLICATIONS

Watson, A.P., Evans, R.L. & Egland, K.A. Multiple functions of sushi domain containing 2 (SUSD2) in breast tumorigenesis. Mol Cancer Res 11, 74-85 (2013).
Pan, W., et al. CSBF/C10orf99, a novel potential cytokine, inhibits colon cancer cell growth through inducing G1 arrest. Sci Rep 4, 6812 (2014).
Cai, C., et al. Reduced expression of sushi domain containing 2 is associated with progression of non-small cell lung cancer. Oncol lett 10, 3619-3624 (2015).
Sheets, J.N., et al. SUSD2 expression in high-grade serous ovarian cancer correlates with increased patient survival and defective mesothelial clearance. Oncogenesis 5, e264 (2016).
Hultgren, E.M., Patrick, M.E., Evans, R.L., Stoos, C.T. & Egland, K.A. SUSD2 promotestumor-associated macrophage recruitment by increasing levels of MCP-1 in breast cancer. PloS One 12, e0177089 (2017).
Zhang, S., et al. Downregulation of endometrial mesenchymal marker SUSD2 causes cell senescence and cell death in endometrial carcinoma cells. PloS One 12, e0183681 (2017).
Umeda, S., et al. Expression of sushi domain containing two reflects the malignant potential of gastric cancer. Cancer Med 7, 5194-5204 (2018).
Li, X., et al. Myeloid-derived cullin 3 promotes STAT3 phosphorylation by inhibiting OGT expression and protects against intestinal inflammation. J Exp Med 214, 1093-1109 (2017).
McLane, L.M., Abdel-Hakeem, M.S. & Wherry, E.J. CD8 T Cell Exhaustion During Chronic Viral Infection and Cancer. Annu Rev Immunol 37, 457-495 (2019).
Miller, B.C., et al. Subsets of exhausted CD8(+) T cells differentially mediate tumor control and respond to checkpoint blockade. Nat Immunol 20, 326-336 (2019).
Chen, Z., et al. TCF-1-Centered Transcriptional Network Drives an Effector versus Exhausted CD8 T Cell-Fate Decision. Immunity 51, 840-855 e845 (2019).
Hudson, W.H., et al. Proliferating Transitory T Cells with an Effector-like Transcriptional Signature Emerge from PD-1(+) Stem-like CD8(+) T Cells during Chronic Infection. Immunity 51, 1043-1058 e1044 (2019).
Zander, R., et al. CD4(+) T Cell Help Is Required for the Formation of a Cytolytic CD8(+) T Cell Subset that Protects against Chronic Infection and Cancer. Immunity 51, 028-1042 e1024 (2019).
Lin, H., et al. Host expression of PD-L1 determines efficacy of PD-L1 pathway blockade-mediated tumor regression. J Clin Invest 128, 805-815 (2018).
Wen, H., Dou, Y., Hogaboam, C.M. & Kunkel, S.L. Epigenetic regulation of dendritic cell-derived interleukin-12 facilitates immunosuppression after a severe innate immune response. Blood 111, 1797-1804 (2008).
Mo, F., et al. An engineered IL-2 partial agonist promotes CD8(+) T cell stemness. Nature 597, 544-548 (2021).
Chen, J., et al. NR4A transcription factors limit CAR T cell function in solid tumours. Nature 567, 530-534 (2019).
Lotze, M.T., et al. High-dose recombinant interleukin 2 in the treatment of patients with disseminated cancer. Responses, treatment-related morbidity, and histologic findings. JAMA 256, 3117-3124 (1986).
Dudley, M.E., et al. Cancer regression and autoimmunity in patients after clonal repopulation with antitumor lymphocytes. Science 298, 850-854 (2002).
Zhu, E.F., et al. Synergistic innate and adaptive immune response to combination immunotherapy with anti-tumor antigen antibodies and extended serum half-life IL-2. Cancer Cell 27, 489-501 (2015).
Moynihan, K.D., et al. Eradication of large established tumors in mice by combination immunotherapy that engages innate and adaptive immune responses. Nature medicine 22, 1402-1410 (2016).
Hsu, E.J., et al. A cytokine receptor-masked IL2 prodrug selectively activates tumor-infiltrating lymphocytes for potent antitumor therapy. Nat Commun 12, 2768 (2021).
Levin, A.M., et al. Exploiting a natural conformational switch to engineer an interleukin-2 'superkine'. Nature 484, 529-533 (2012).
Silva, D.A., et al. De novo design of potent and selective mimics of IL-2 and IL-15. Nature 565, 186-191 (2019).
Bentebibel, S.E., et al. A First-in-Human Study and Biomarker Analysis of NKTR-214, a Novel IL2Rbetagamma-Biased Cytokine, in Patients with Advanced or Metastatic Solid Tumors. Cancer Discov 9, 711-721 (2019).
Diab, A., et al. Bempegaldesleukin (NKTR-214) plus Nivolumab in Patients with Advanced Solid Tumors: Phase I Dose-Escalation Study of Safety, Efficacy, and Immune Activation (PIVOT-02). Cancer Discov 10, 1158-1173 (2020).
Hashimoto, M., et al. CD8 T Cell Exhaustion in Chronic Infection and Cancer: Opportunities for Interventions. Annu Rev Med 69, 301-318 (2018).
Beltra, J.C., et al. Developmental Relationships of Four Exhausted CD8(+) T Cell Subsets Reveals Underlying Transcriptional and Epigenetic Landscape Control Mechanisms. Immunity 52, 825-841 e828 (2020).
West, E.E., et al. PD-L1 blockade synergizes with IL-2 therapy in reinvigorating exhausted T cells. J Clin Invest 123, 2604-2615 (2013).
Wen, H., Lei, Y., Eun, S.Y. & Ting, J.P. Plexin-A4-semaphorin 3A signaling is required for Toll-like receptor- and sepsis-induced cytokine storm. J Exp Med 207, 2943-2957 (2010).
Zilionis, R., et al. Single-cell barcoding and sequencing using droplet microfluidics. Nat rotoc 12, 44-73 (2017).
Zuo, D., et al. PlasmID: a centralized repository for plasmid clone information and distribution. Nucleic Acids Res 35, D680-684 (2007).
Lin, Y.H., et al. Self-Assembled STrap for Global Proteomics and Salivary Biomarker Discovery. J Proteome Res 18, 1907-1915 (2019).
Tyanova, S., Temu, T. & Cox, J. The MaxQuant computational platform for mass spectrometry-based shotgun proteomics. Nat Protoc 11, 2301-2319 (2016).

* cited by examiner gRNA 1: GTCCACAGGTGCCGATAGACAGG
gRNA 1: GAAATGGGAGCTTCCAACGCAGG Genotyping:
Primer 1: CAACACTTCTCCATCAGTAACCTGCACT
Primer 2: ACTCTAAAGCTGGCTGGCTATTCATCA
Primer 3: CTCACGGACAGTTATGGAACCGTG a Human *IL2RA* sequencing:

CAATGGGAGCAATAGCAGAGCTCGTTTAGTGACCGTCAGAATTAACCATGGACTACAAAGACCATGA
CGGTGATTATAAAGATCATGACATCGATTACAAGGATGACGATGACAAGCTTGCGGCCGCGAATTCA
ATGGATTCATACCTGCTGATGTGGGGACTGCTCACGTTCATCATGGTGCCTGGCTGCCAGGCAGAGCT
CTGTGACGATGACCCGCCAGAGATCCCACACGCCACATTCAAAGCCATGGCCTACAAGGAAGGAACC
ATGTTGAACTGTGAATGCAAGAGAGGTTTCCGCAGAATAAAAAGCGGGTCACTCTATATGCTCTGTACA
GGAAACTCTAGCCACTCGTCCTGGGACAACCAATGTCAATGCACAAGCTCTGCCACTCGGAACACAAC
GAAACAAGTGACACCTCAACCTGAAGAACAGAAAGAAAGGAAAACCACAGAAATGCAAAGTCCAATGC
AGCCAGTGGACCAAGCGAGCCTTCCAGGTCACTGCAGGGAACCTCCACCATGGGAAAATGAAGCCAC
AGAGAGAATTTATCATTTCGTGGTGGGGCAGATGGTTTATTATCAGTGCGTCCAGGGATACAGGGCTC
TACACAGAGGTCCTGCTGAGAGCGTCTGCAAAATGACCCACGGGAAGACAAGGTGGACCCAGCCCCA
GCTCATATGCACAGGTGAAATGGAGACCAGTCAGTTTCCAGGTGAAGAGAAGCCTCAGGCAAGCCCC
GAAGGCCGTCCTGAGAGTGAGACTTCCTGCCTCGTCACAACAACAGATTTTCAAATACAGACAGAAAT
GGCTGCAACCATGGAGACGTCCATATTTACAACAGAGTACCAGGTAGCAGTGGCCGGCTGTGTTTTCC
TGCTGATCAGCGTCCTCCTCCTGAGTGGGCTCACCTGGCAGCGGAGACAGAGGAAGAGTAGAAGAAC
AATCTAGTCTAGAGGATCCCGGGTGGCATCCCTGTGACCCCTCCCCAGTGCCTCTCCTGGCCCTGGA
AGTTGCCACTCCAGTGCCCACCAGCCTTGTCCTAATAAAATTAAGTTGCATCATTTTGTCTGACTAGGT
GTCCTTCTATATATTATGGGGTGGAGGGGGGKGKGGWWWKGRRSCAAGGGGCAAGTTGGGAAGAMA
CCTGTAGGGCCTGCGGGTYTATTGGGAACCAAGCTGGAGTGCAGKGCACATCTGGCTCMCTGCATCT
CCGCCTCCTGGGTCAGCGATCTCCTGCCTCAGCCTCCCGAGTTGTGGGATTCAGGCATGCATGACAG
GCTCAGCTATTTTTGTTTTTTGTARRACGGTTTCACCATATTGGCAGCTGGTCTCCACTCCTATYYCAG
GKGATCTACCCACCTTGGCCTCCAAA SEQ ID NO. 34

Underline: 3×Flag tag; ATG and TAG represent the start and stop codon, respectively.

FIG. 12A

TARGETABLE IMMUNE CHECKPOINT FOR IMMUNOTHERAPY

CROSS-REFERENCE TO RELATED APPLICATIONS

This application claims the benefit of U.S. Provisional Application No. 63/298,808, filed on Jan. 12, 2022, U.S. Provisional Application No. 63/336,502, filed on Apr. 29, 2022, and U.S. Provisional Application No. 63/378,271, filed on Oct. 4, 2022, which are incorporated herein by reference in their entirety.

STATEMENT REGARDING FEDERALLY SPONSORED RESEARCH

This invention was made with Government Support under Grant No. R01AI62779 awarded by the National Institutes of Health. The Government has certain right in the invention.

REFERENCE TO SEQUENCE LISTING

A Sequence Listing conforming to the rules of WIPO Standard ST.26 is hereby incorporated by reference. Said Sequence Listing has been filed as an electronic document via Patent Center in ASCII format encoded as XML. The electronic document, created on Jan. 12, 2023, is entitled "103361-221US1.xml", and is 34,278 bytes in size.

FIELD

The present disclosure relates to the field of T cell-based immunotherapy to promote anticancer effector functions.

BACKGROUND

Despite the recent development of immune checkpoint blockade (ICB) as a revolutionizing cancer treatment, only a small fraction of patients gain sustained clinical benefit from this therapy.

The failure in achieving durable clinical response is largely due to the establishment of an immunosuppressive tumor microenvironment (TME). Decline of immune function in effector $CD8^+$ T cells is a key feature of immunosuppressive TME in cancer patients who show resistance to ICB treatment. Therefore, how to restore effector functions of $CD8^+$ T cells represents a central theme for the development of effective cancer immunotherapy. However, a major challenge remaining in ICB immunotherapy is the existence of multiple immune checkpoint molecules. As a result, targeting of a single molecule cannot override compensatory signals from other immune inhibitory molecules. As such, there is an urgent need to identify new therapeutic targets to rejuvenate $CD8^+$ T cell antitumor immunity, either alone or in combination with existing ICB treatments. There is a need to address these problems associated with treating and preventing cancers with immunosuppressive tumor microenvironments.

The compounds, compositions, and methods disclosed herein address these and other needs.

SUMMARY

The present disclosure provides genetically modified cells and compositions for anticancer immunotherapies. The present disclosure also provides methods of treating cancer using the genetically modified cells and compositions.

In one aspect, disclosed herein is a genetically modified cell comprising a deletion of the SUSD2 gene or a fragment thereof. In some embodiments, the cell comprises a complete deletion of the SUSD2 gene. In some embodiments, the cell is a T cell. In some embodiments, the T cell is a $CD8^+$ T cell. In some embodiments, the cell comprises a chimeric antigen receptor (CAR).

In one aspect, disclosed herein is a composition comprising the cell of any preceding aspect and an anticancer agent. In some embodiments, the anticancer agent is an immunotherapeutic agent. In some embodiments, the immunotherapeutic agent comprises a PD-L1 antibody. In some embodiments, the immunotherapeutic agent comprises a PD-1 antibody.

In one aspect, disclosed herein is a method of treating a cancer comprising administering to a subject a genetically modified cell comprising deletion of the SUSD2 gene or a fragment thereof. In some embodiments, the cell comprises a complete deletion of the SUSD2 gene. In some embodiments, the cell is a T cell. In some embodiments, the T cell is a $CD8^+$ T cell.

In some embodiments, the cell comprises a chimeric antigen receptor (CAR). In some embodiments, the subject is further administered an anticancer agent. In some embodiments, the subject is further administered an immunotherapeutic agent.

In some embodiments, the subject is further administered a PD-L-1 antibody. In some embodiments, the subject is further administered a PD-1 antibody. In some embodiments, the subject is further administered a CTLA-4 antibody.

In some embodiments, the cancer is a colon adenocarcinoma. In some embodiments, the cancer is a lymphoma.

BRIEF DESCRIPTION OF FIGURES

The accompanying figures, which are incorporated in and constitute a part of this specification, illustrate several aspects described below.

FIGS. 1A-1C shows the tumor growth at day 7, 9, 11, 13, 15, 17, 19 and 21 post inoculation with MC38, EG7, or B16-OVA tumor cells in wild-type (WT) and $Susd2^{-/-}$ mice. Dotted lines, values from individual mouse; solid lines, mean values. FIGS. 1D-1E shows the uniform manifold approximation and projection (UMAP) of intratumoral $CD45^+$ cells and quantitation of each cell type in WT and $Susd2^{-/-}$ mice at day 18 post-inoculation with MC38 tumors. Clusters denoted by numbers 0-17 are labeled with inferred cell types. FIGS. 1F-1G shows the UMAP and quantitation of intratumoral $Cd8a^+Trbc1^+Trbc2^+$ cells in WT and $Susd2^{-/-}$ mice at day 18 post-inoculation with MC38 tumors. Clusters are labeled with inferred intratumoral $CD8^+$ cell subtypes. FIGS. 1H-1I shows the heatmap of differentially expressed genes between WT and $Susd2^{-/-}$ intratumoral $CD8^+$ cells and violin plots showing Ifng and Gzmb expression in WT and $Susd2^{-/-}$ intratumoral $CD8^+$ cells from mice as in FIGS. 1D-1E. FIG. 1J shows the Gene Ontology (GO) enrichment in WT and $Susd2^{-/-}$ intratumoral $CD8^+$ cells from mice as in FIGS. 1D-1E. Hypergeometric test was used for functional enrichment in Enrichr. All P-values were Benjamini-Hochberg adjusted for multiple comparisons. n=10; n=7; WT, n=6, $Susd2^{-/-}$, n=7. Data in are representative of four independent experiments. Statistical significance was calculated with two-way ANOVA followed by Tukey's multiple comparisons test with P values noted in the figure.

FIGS. 2A-2B show flow cytometry analysis showing percentage of CD4$^+$ and CD8$^+$ T cells and CD25$^+$Foxp3$^+$ Treg cells in MC38 subcutaneous tumor isolated from WT or Susd2$^{-/-}$ mice at day 18 post-tumor inoculation. FIG. 2M-2Q show the tumor growth and survival in WT and Susd2$^{-/-}$ mice inoculated with EG7, B16-F10, and MC38 tumor cells and injected with control IgG or PD-1 antibody at day 7, 10 and 13 post tumor inoculation. FIGS. 2A-2D and 21; n=5; FIG. 2E; WT, n=6, Susd2$^{-/-}$, n=7; FIGS. 2F-2H and 2K; n=8; FIG. 21; n=7; FIGS. 2J and 2M; n=10. n, number of mice per group. Data are representative of three independent experiments and two independent experiments. Statistical significance was determined by two-tailed unpaired Student's t-test, the P value was calculated using two-sided Wilcoxon's rank-sum test and adjusted with Bonferroni's correction, two-way ANOVA followed by Tukey's multiple comparisons test, or Log-rank (Mantel-Cox) test survival analysis with P values noted in the figure. The data represent mean±SD.

FIGS. 3A-3C shows the transcript and protein of SUSD2 in various immune cell types isolated from mouse spleen or human PBMCs. FIG. 3M shows the in vitro killing of OVA257-264 peptide-pulsed MC38 (upper), EG7 (middle) and B16-OVA (lower) cells by WT or Susd2$^{-/-}$ OT-I T cells after co-culture for 4 h. FIGS. 3O-3T shows the flow cytometry analysis showing Thy1.2$^+$CD8$^+$ T cells, IFN-γ+CD8$^+$ T cells, GzmB$^+$CD8$^+$ T cells, TNF$^+$CD8$^+$ T cells, TCF-1$^+$PD-1$^+$CD8$^+$ T cells and Tim-3$^+$ PD-1$^+$CD8$^+$ T cells in EG7 isolated from OVA257-264 primed WT or Susd2$^{-/-}$ OT-I T cells transferred tumor bearing mice at day 18 post tumor inoculation. TCF-1$^+$PD-1$^+$CD8$^+$ T cells were gated from PD-1$^+$CD8$^+$ T cells. FIGS. 3A, 3B, 3D-3F, and 3H-3M; n=3; FIGS. 3N-3Q; n=5. n, number of mice per group. Data are representative of three independent experiments and four independent experiments. Statistical significance was determined by one-way ANOVA followed by Tukey's test, two-tailed unpaired Student's t-test, or two-way ANOVA followed by Sidak's multiple comparisons test, or Tukey's multiple comparisons test with P values noted in the figure. The data represent mean±SD.

FIG. 4A shows the LC-MS/MS of Susd2-interacting proteins in Susd2-containing protein complex immunoprecipitated from Susd2$^{-/-}$ OT-I T cells reconstituted with either V5-tagged mouse Susd2 or empty vector (PSMs, peptide-spectrum matches). FIG. 4B shows the schematic domain structure of SUSD2 and IL-2Rα, SP, signal peptide, SD, sushi domain, TM, transmembrane domain. FIGS. 4C-4D shows the immunoblotting of IL-2Rα, IL-2Rβ or common γ chain and IL-15Rα in Susd2 precipitates immunoprecipitated from Susd2$^{-/-}$ OT-I T cells reconstituted with either empty vector or V5-tagged mouse Susd2. FIGS. 4E-4F shows the immunoblot analysis of V5-SUSD2 and Flag-IL-2Rα in V5-SUSD2 or Flag-IL-2Rα precipitates immunoprecipitated from 293T cells transfected with V5-SUSD2 and Flag-IL2RA. FIG. 4G shows the immunofluorescence of 293T cells transfected with mCherry-SUSD2 and eGFP-IL2RA at 48 hours after transfection. FIG. 4H the immunoblot analysis of SUSD2 and IL-2Rα in V5-SUSD2 precipitates immunoprecipitated from Jurkat T cells transduced with either V5-SUSD2 or empty vector. FIG. 4I shows the immunoblot analysis of V5-SUSD2$^{FL}$, V5-SUSD2$^{\Delta SD}$ and Flag-Il-2Rα in V5-SUSD2$^{FL}$ or V5-SUSD2$^{\Delta SD}$ precipitates immunoprecipitated from 293T cells transfected with V5-SUSD2$^{FL}$, V5-SUSD2$^{\Delta SD}$ and Flag-Il2rα. FIG. 4J-4K shows the immunoblot analysis of V5-SUSD2, Flag-IL-2Rα, Flag-IL-2Rα$^{SD1}$ and Flag-IL-2Rα $^{SD2}$ in V5-SUSD2 precipitates immunoprecipitated from 293T cells transfected with V5-SUSD2, Flag-Il2RA, Flag-Il2RA$^{\Delta SD1}$ and Flag-Il2RA$^{\Delta SD2}$. FIG. 4A; n=4. Bars show medians and symbols show individual mice. Statistical significance was determined by two-tailed unpaired Student's t-test with P values noted in the figure. Data are from two independent experiments and three independent experiments. The data represent mean±SD. WCL, Whole cell lysate, EV, Empty Vector.

FIGS. 5A-5B shows the flow cytometry analysis of phosphorylated STAT5 (p-STAT5) and intracellular GzmB in OVA257-264-primed WT or Susd2$^{-/-}$ OT-I T cells rested overnight and then stimulated with IL-2 (100 U/ml), IL-7 (5 ng/ml) or IL-15 (10 ng/ml) for 0, 30, 60, 120 and 240 minutes. FIGS. 5C-5E shows the flow cytometry analysis of intracellular IFN-γ, GzmB, and cell apoptosis in WT or Susd2$^{-/-}$ OT-I T cells stimulated with 200 ng/ml OVA257-264 (suboptimal dose) for 48 hours. FIG. 5F shows the flow cytometry analysis of IL-2Rα expression in OVA257-264-stimulated WT or Susd2$^{-/-}$ OT-I T cells. FIG. 5G shows the flow cytometry analysis of binding of biotinylated IL-2 on 293T cells overexpressing SUSD2 and/or IL2RA. FIGS. 5H-5J shows the flow cytometry analysis of biotinylated IL-2 binding to WT or Susd2$^{-/-}$ OT-I T cells treated or not with unconjugated IL-2. FIGS. 5A-5H; n=3. n, number of mice per group. Data are representative of three independent experiments and four independent experiments. Statistical significance was determined by two-way ANOVA followed by Sidak's multiple comparisons test with P values noted in the figure. The data represent mean±SD.

FIG. 6A shows the flow cytometry analysis of GFP in $OVA_{257-264}$-primed $Susd2^{-/-}$ OT-I T cells transfected with EV-GFP or $SUSD2^{FL}$-GFP. FIGS. 6B-6D shows the flow cytometry of IFN-$\gamma^+CD8^+$ T cells, $GzmB^+CD8^+$ T cells and annexin-$V^+$ 7-$AAD^+CD8^+$ T cells in $OVA_{257-264}$-stimulated $Susd2^{-/-}$ OT-I T cells retrovirally transduced with EV-GFP, $SUSD2^{FL}$-GFP or $SUSD2^+$SD-GFP. FIGS. 6E-6F shows the binding of biotinylated IL-2 assessed by streptavidin staining and STAT5 phosphorylation in $OVA_{257-264}$-primed $Susd2^{-/-}$ OT-I T cells retrovirally transduced with EV-GFP, $SUSD2^{FL}$-GFP or $SUSD2^+$SD-GFP and stimulated with biotin-conjugated IL-2 for 1 h following overnight resting post-transduction. FIG. 6G shows the tumor growth in EG7-bearing Thy1.1 congenic mice at day 2, 4, 6, 8, 10, 12 and 14 post PBS treatment or post-transfer with $Susd2^{-/-}$ OT-I T cells transduced with EV-GFP, $SUSD2^{FL}$-GFP or $SUSD2^{\Delta SD}$-GFP. FIGS. 6H-6M shows the frequencies of $Thy1.2^+CD8^+$ T cells, IFN-$\gamma^+CD8^+$ T cells, $GzmB^+CD8^+$ T cells, $TNF^+CD8^+$ T cells, TCF-$1^+$PD-$1^+CD8^+$ T cells, and Tim-$3^+$ PD-$1^+CD8^+$ T cells in EG7 tumors isolated at day 18 post EG7 inoculation from Thy1.1 mice that received $Susd2^{-/-}$ OT-I T cells transduced with EV-GFP, $SUSD2^{FL}$-GFP or $SUSD2^+$SD-GFP at day 7 post EG7 inoculation. FIGS. 6A-6F; n=3; FIGS. 6G-6J; n=5. n, number of mice per group. Data are representative of five independent experiments and three independent experiments. Statistical significance was determined by two-way ANOVA followed by Tukey's multiple comparisons test, or one-way ANOVA followed by Tukey's test with P values noted in the figure. The data represent mean±SD.

FIG. 7A shows the tumor growth and survival in EL4-hCD19 tumors-bearing $Rag2^{-/-}$ mice that received adoptive transfer of WT or $Susd2^{-/-}$ CAR T cells at day 7 post tumor inoculation. FIGS. 7G-7S shows the frequencies of IFN-$\gamma^+CD8^+$ T cells, $GzmB^+CD8^+$ T cells, $TNF^+CD8^+$ T cells and IL-$2^+$ $CD8^+$ T cells, TCF-$1^+$PD-$1^+CD8^+$ T cells, and Tim-$3^+$ PD-$1^+CD8^+$ T cells in EL4-hCD19 tumors isolated from $Rag2^{-/-}$ mice transferred with sgRNA or Susd2 gRNA CAR T cells at day 18 post tumor inoculation. FIG. 7A, n=5-γ; FIG. 7F, n=5-8; FIGS. 7B-E and 7G-7I, n=5. n, number of mice per group. Data are representative of three independent experiments and two independent experiments. Statistical significance was determined by two-way ANOVA followed by Tukey's multiple comparisons test, Log-rank (Mantel-Cox) test survival analysis, or two-tailed unpaired Student's t-test with P values noted in the figure. The data represent mean±SD.

FIG. 8A shows a cartoon of the strategy to generate $Susd2^{-/-}$ mice with a CRISPR/Cas9-mediated genome engineering strategy. The sequences of two guide RNA and the primers used for genotyping were shown. FIG. 8B shows the genotyping results for WT or $Susd2^{-/-}$ alleles. FIGS. 8C-8G shows the flow cytometry analysis of T cells ($CD3^+$) and natural killer cells ($NK1.1^+$), $CD4^+$ and $CD8^+$ T cells, regulatory T cells in naïve status ($CD4^+CD25^+$), macrophage ($CD11b^+F4/80^+$), conventional dendritic cells ($CD11b^+CD11c^+$), monocytes ($CD11b^+Ly6C^+$), neutrophils ($CD11b^+Ly6G^+$), and histogram of B cells ($CD19^+$) in spleen from wild type and $Susd2^{-/-}$ mice were. FIG. 8C-8J, WT, n=4 mice, $Susd2^{-/-}$, n=5 mice. Data are representative of three independent experiments. Statistical significance was determined by two-tailed, unpaired Student's t-test, there is no significant difference between WT and $Susd2^{-/-}$ in (P>0.05). All data are mean±SD.

FIGS. 9A-9G shows the flow cytometry analysis of $CD11b^+$ $F4/80^+$macrophages, $CD11b^+CD11c^+$ dendritic cells, $CD11b^+Ly6C^+$ monocytes, $CD11b^+Ly6G^+$ neutrophils, $NK1.1^+$ NK cells, IFN-$\gamma^+$ $NK1.1^+$ NK cells, IFN-$\gamma^+CD4^+$, $GzmB^+CD4^+$ and $TNF^+CD4^+$ T cells in MC38 tumor isolated from WT or $Susd2^{-/-}$ mice at Day 18. FIG. 9H-9I shows the spectral flow cytometry analysis of intratumor $CD8^+$ T cells from WT and $Susd2^{-/-}$ mice at day 18 post MC38 tumor inoculation. UMAP of individual marker expression patterns and frequencies of individual clusters of WT and $Susd2^{-/-}$ samples, Boxes represent median and 25th to 75th percentiles, whiskers are minimum to maximum values excluding outliers (two-sided Wilcoxon's rank-sum P value). FIG. 9J-9L shows the flow cytometry analysis of PD-$1^+CD8^+$ T cells and LAG-$3^+$ $CD8^+$ T cells in MC38, EG7, or B16-OVA tumors isolated from WT or $Susd2^{-/-}$ mice at day 18 post tumor inoculation. FIGS. 9A-9D, 9G, and 9J-9L, n=5, FIGS. 9E, 9F, and 9I, n=8. n, number of mice per group. Data are representative of three independent experiments and two independent experiments. Statistical significance was determined by two-tailed, unpaired Student's t-test, there is no significant difference between WT and $Susd2^{-/-}$ group (P>0.05). All data are mean±SD.

FIG. 10A shows the flow cytometry analysis of IFN-$\gamma^+CD8^+$ T cells, $GzmB^+$ $CD8^+$ T cells and $TNF^+CD8^+$ T cells in different $OVA_{257-264}$ dosage stimulated splenocytes isolated from WT or $Susd2^{-/-}$ OT-I mice. FIGS. 10B-10E shows that $CD8^+$ T cells were isolated from total splenocytes of either WT or $Susd2^{-/-}$ OT-I mice left untreated or stimulated with $OVA_{257}$-264 for 3 days and were subjected to RNA-seq assay. The volcano plot of RNA-seq data demonstrates differential gene expression between WT and $Susd2^{-/-}$ $CD8^+$ T cells at Day 0 and Day 3. A heatmap of the top thirty genes representing genes differentially expressed between WT and $Susd2^{-/-}$ $CD8^+$ T cells at Day 0 and Day 3. FIG. 10F shows the intracellular accumulation of IFN-7 in $CD8^+$ T cells isolated from WT or $Susd2^{-/-}$ OT-I mice that were cocultured with either WT or $Susd2^{-/-}$ bone marrow-derived dendritic cells (BMDCs) that have been pulsed with OVA257-264. FIGS. 10A and 10F, n=3, FIG. 10B-10E, n=4. n, number of mice per group. Data are representative of four independent experiments and two independent experiments. Statistical significance was calculated using two-sided Wilcoxon's rank-sum test and adjusted with Bonferroni's correction. Statistical significance was determined by two-way ANOVA followed by Sidak's multiple comparisons test with P values noted in the figure. All data are mean±SD.

FIG. 11A shows the flow cytometry analysis of IFN-γ$^+$CD4$^+$ T cells, GzmB$^+$CD4$^+$ T cells and TNF$^+$CD4$^+$ T cells in $OVA_{323-339}$ stimulated splenocytes isolated from WT or Susd2$^{-/-}$ OT-II mice. FIG. 11B shows the flow cytometry analysis of intranuclear level of Foxp3 in spleen CD4$^+$ T cells from WT or Susd2$^{-/-}$ mice. FIG. 11C shows the cell proliferation of naïve CD4$^+$ T cells upon stimulation with CD3-CD28 antibody in the absence or presence of WT or Susd2$^{-/-}$ Treg cells at the indicated cell:cell ratio was measured by the staining of carboxyfluorescein diacetate succinimidyl ester (CFSE), followed by FACS analysis. FIGS. 11A-11C, n=3. n, number of mice per group. Data are representative of four independent experiments. Statistical significance was determined by two-tailed, unpaired Student's t-test, there is no significant difference between WT and Susd2$^{-/-}$ group in (P>0.05). All data are mean±SD.

FIGS. 12A and 12B show the authenticity of the IL-2Rα molecular weight. FIG. 12A shows the sanger sequencing result of pCMV3×Flag-IL2RA vector. FIG. 12B shows the transcript of Susd2 in mouse CD8$^+$ T cells stimulated with CD3-CD28 Ab, IL-2, IL-7 or IL-15 for 0, 1, 2 and 3 days. The sequence is FIG. 12A is SEQ ID NO:34.

FIG. 13A-13C show the immunoblotting of Flag-IL2Rα in 293T cells transfected with pCMV3×Flag-IL2RA vector. Data are representative of three independent experiments. FIGS. 13A-13C shows the immunoblotting of STAT5 in OVA257-264-primed WT or Susd2$^{-/-}$ OT-I T cells which were rested overnight, and then stimulated with IL-2 (100 U/ml), IL-7 (5 ng/ml) or IL-15 (10 ng/ml) for 0, 30, 60, 120 and 240 minutes. FIGS. 13D-13E shows the flow cytometry analysis of p-STAT5 in WT or Susd2$^{-/-}$ Treg cells stimulated with IL-2 (100 U/ml) for 0, 30, 60 and 120 minutes. FIG. 13F shows the CD8$^+$ T cells isolated from WT or Susd2$^{-/-}$ OT-I mice were cocultured with WT or Susd2$^{-/-}$ bone marrow-derived dendritic cells (BMDCs) that have been pulsed with OVA257-264.Intracellular accumulation of IFN-γ in WT or Susd2$^{-/-}$ CD8$^+$ T cells in the absence or presence of blocking antibodies against IL-2, IL-2Rα, or IL-2Rβ were measured by FACS analysis. FIGS. 13G-13H shows the tumor growth in WT and Susd2$^{-/-}$ mice bearing B16-F10 tumor cells which were injected with IL-2/AbCD25 complex or IL-2/AbCD122 complex. FIGS. 13I-K shows the flow cytometry analysis of intracellular accumulation of IFN-γ, GzmB and TNF-expressing intratumoral CD8$^+$ T cells. FIGS. 13A, 13E, and 13F, n=3; FIGS. 13G-13K, n=5. n, number of mice per group. Data are representative of three independent experiments and two independent experiments. Statistical significance was determined by two-way ANOVA followed by Sidak's multiple comparisons test or one-way ANOVA followed by Tukey's test with P values noted in the figure. All data are mean±SD.

FIG. 14A shows the validation of EL4 thymoma cell line expressing human CD19 (EL4-hCD19) with the deletion of its intracellular domain. FIG. 14B shows the percentages of CD8$^+$ T cells retrovirally transduced with a chimeric antigen receptor (CAR) containing a portion of hCD19 single chain variable fragment (ScFv) fused with signaling domains of mouse CD28 and mouse CD3 (sequence (with first and third ITAMs of the CD3 (molecule inactivated) before and after cell sorting were assessed by the staining with anti-Thy1.1 antibody. FIG. 14C shows the transcript of Susd2 in CAR T cells that have been electroporated with scrambled gRNA(sgRNA) or Susd2 gRNA-Cas9 nucleoprotein (RNP) complex, sgRNA versus Susd2 gRNA (P=0.0010). FIG. 14C, n=3. Data are representative of two independent experiments. Statistical significance was determined by two-tailed, unpaired Student's t-test with P values noted in the figure. The data represent mean±SD.

DETAILED DESCRIPTION

Figure 1A:
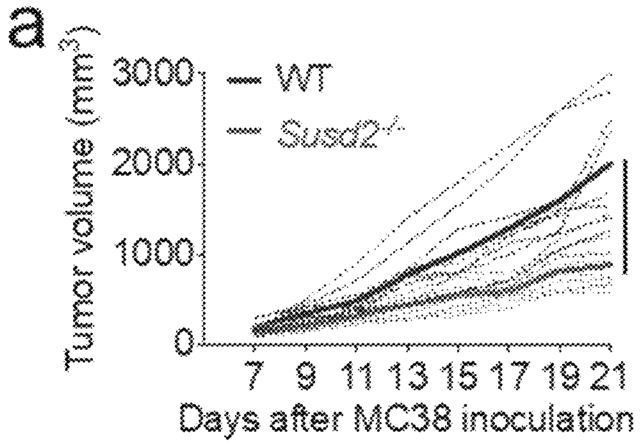
FIGS. 1A-1J show the genetic deletion of Susd2 results in improved antitumor immunity.

The present disclosure provides genetically modified cells and compositions for anticancer immunotherapies. The present disclosure also provides methods of treating cancer using the genetically modified cells and compositions.

Those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Reference will now be made in detail to the embodiments of the invention, examples of which are illustrated in the drawings and the examples. This invention may, however, be embodied in many different forms and should not be construed as limited to the embodiments set forth herein.

Terminology

Unless defined otherwise, all technical and scientific terms used herein have the same meaning as commonly understood to one of ordinary skill in the art to which this disclosure belongs. The following definitions are provided for the full understanding of terms used in this specification.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Amino acids" are used herein to refer to chemical compounds with the general formula: $NH_2$—CRH COOH, where R, the side chain, is H or an organic group. Where R is organic, R can vary and is either polar or nonpolar (i.e., hydrophobic). The following abbreviations are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine. Unless otherwise indicated, the term "amino acid" as used herein also includes amino acid derivatives that nonetheless retain the general formula.

As used herein, the term "genetically modified" refers to a living cell, tissue, or organism whose genetic material has been altered using genetic engineering techniques. The genetic modification results in an alteration that does not occur naturally by mating and/or natural recombination. Modified genes can be transferred within the same species, across species (creating transgenic organisms), and across kingdoms. New, exogenous genes can be introduced, or endogenous genes can be enhanced, altered, or knocked out.

As used herein, the term, "deletion", also called gene deletion, deficiency, or deletion mutation, refers to part of a chromosome or a sequence of DNA being left out during DNA replication. Deletion, or gene deletions can cause any number of nucleotides to be deleted from a single base to an entire piece of chromosome.

A "T cell" refers to a type of lymphocyte that is one of the white blood cells of the immune system. T cells can be distinguished from other lymphocytes by the presence of a T-cell receptor (TCR) on their cell surface. The immune-mediated cell death function of T cells is carried by two major subtypes: $CD8^+$ "killer" T cells and $CD4^+$"helper T cells.

A "chimeric antigen receptor" or "CAR" is an artificial T cell receptor used for immunotherapy. CAR are protein receptors that have been engineered to give T cells an enhanced ability to target a specific protein. CAR receptors are chimeric and include the antigen binding and T cell activating functions in a single receptor.

The terms "immunotherapy" and "immunotherapeutic" refers to the treatment of disease by activating or suppressing the immune system. In cancer treatment, the most effective immunotherapies can be cell-based immunotherapies that utilize lymphocytes, macrophages, dendritic cells, natural killer cells, cytotoxic T lymphocytes, etc. to defend the body against cancer by targeting abnormal antigens expressed on the surface of tumor cells.

The terms "anticancer" refers to a substance, composition, or formula that counteracts the effects or inhibits the development of a cancerous cells and tissues.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% or more decrease so long as the decrease is statistically significant.

By "reduce" or other forms of the word, such as "reducing" or "reduction," is meant lowering of an event or characteristic. It is understood that this is typically in relation to some standard or expected value, in other words it is relative, but that it is not always necessary for the standard or relative value to be referred to.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

The term "antibody fragment" refers to a portion of a full-length antibody, generally the target binding or variable region. Examples of antibody fragments include Fab, Fab', $F(ab')_2$ and Fv fragments. The phrase "functional fragment or analog" of an antibody is a compound having qualitative biological activity in common with a full-length antibody. As used herein, "functional fragment" with respect to antibodies, can include Fv, F(ab) and $F(ab')_2$ fragments. An "Fv" fragment is the minimum antibody fragment which contains a complete target recognition and binding site. This region consists of a dimer of one heavy and one light chain variable domain in a tight, association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The terms "treat," "treating," "treatment," and grammatical variations thereof as used herein, include partially or completely delaying, alleviating, mitigating, or reducing the intensity of one or more attendant symptoms of a disorder or condition and/or alleviating, mitigating, or impeding one or more causes of a disorder or condition. Treatments according to the disclosure may be applied preventively, prophylactically, palliatively or remedially. Treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a vector, polynucleotide, cells, salts, esters, amides, proagents, active metabolites, isomers, fragments, analogs, and the like. When the term "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc.

A "control" is an alternative subject or sample used in an experiment for comparison purpose. A control can be "positive" or "negative." For example, where the purpose of the experiment is to determine a correlation of an altered expression level of a proto-oncogene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

As used herein, by a "subject" is meant an individual. Thus, the "subject" can include domesticated animals (e.g., cats, dogs, etc.), livestock (e.g., cattle, horses, pigs, chickens, ducks, geese, sheep, goats, etc.), laboratory animals (e.g., mouse, rabbit, rat, guinea pig, etc.), and birds. "Subject" can also include a mammal, such as a primate or a human. Thus, the subject can be a human or veterinary patient.

Genetically Modified Cells and Compositions

The present disclosure provides genetically modified cells or compositions for anticancer immunotherapies.

In one aspect, disclosed herein is a genetically modified cell comprising a deletion of the SUSD2 gene or a fragment thereof. In some embodiments, the cell comprises a complete deletion of the SUSD2 gene. In some embodiments, the cell comprises a deletion of amino acids 1-820 of SEQ ID NO: 1. In some embodiments, the cell comprises a deletion of one or more of amino acids 1-820 of SEQ ID NO: 1. In some embodiments, the cell comprises a deletion of one or more of amino acids 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, and 820 of SEQ ID NO: 1.

In some embodiments, the cell comprises a deletion of amino acids 1-822 of SEQ ID NO: 2. In some embodiments, the cell comprises a deletion of one or more amino acids 1-822 of SEQ ID NO: 2. In some embodiments, the cell comprises a deletion of amino acids 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, and 822 of SEQ ID NO: 2.

In some embodiments, the cell is a lymphocyte. In some embodiments, the cell is a T cell. In some embodiments, the T cell is a $CD8^+$ T cell. In some embodiments, the cell is a $CD4^+$ T cell. In some embodiments, the cell is a natural killer cell. In some embodiments, the cell is a macrophage.

In some embodiments, the cell is a αβT cell, γδT cell, a natural killer T (NKT) cell, a B cell, an innate lymphoid cell (ILC), a cytokine induced killer (CIK) cell, a cytotoxic T lymphocyte (CTL), a lymphokine activated killer (LAK) cell, or a regulatory T cell.

In one aspect, disclosed herein is a composition comprising a cell and an anticancer agent. In some embodiments, the composition comprises a lymphocyte. In some embodiments, the composition comprises a T cell. In some embodiments, the composition comprises a $CD8^+$ T cell.

In some embodiments, the composition comprises a $CD4^+$ T cell. In some embodiments, the composition comprises a natural killer cell. In some embodiments, the composition comprises a macrophage. In some embodiments, the composition comprises a chimeric antigen receptor (CAR).

In some embodiments, the composition comprises a αβT cell, γδT cell, a natural killer T (NKT) cell, a B cell, an innate lymphoid cell (ILC), a cytokine induced killer (CIK) cell, a cytotoxic T lymphocyte (CTL), a lymphokine activated killer (LAK) cell, or a regulatory T cell.

In some embodiments, the anticancer agent is an immunotherapeutic agent. In some embodiments, the immunotherapeutic agent is an antibody. In some embodiments, the immunotherapeutic agent is a PD-L1 antibody. In some embodiments, the immunotherapeutic agent is a PD-1 antibody. In some embodiments, the immunotherapeutic agent is a CTLA-4 antibody.

In some embodiments, the anticancer agent is a cytokine. In some embodiments, the cytokine includes, but is not limited to IL-1β, IL-2, IL-4, IL-6, IL-8, IL-10, IL-12, IL-15, IL-18, IL-21, IL-22, IFN-γ, TNF-α, TGF-β, LIF, and/or cytotoxins (including, but not limited to perforin and/or granzyme). In some embodiments, the anticancer agent is a chemokine. In some embodiments, the chemokine includes, but is not limited to CCL2, CCL1, CCL19, CCL22, CXCL12, CCL17, MIP-1α, MCP-1, GRO/KC, and/or CXCR3.

In some embodiments, the anticancer agent includes, but is not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPOX, Carac (Fluorouracil-Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil-Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). The treatment methods can include or further include checkpoint inhibitors including, but are not limited to antibodies that block PD-1 (such as, for example, Nivolumab (BMS-936558 or MDX1106), penbrolizumab, CT-011, MK-3475), PD-L1 (such as, for example, atezoizumab, avelumab, durvalumab, MDX-1105 (BMS-936559), MPDL3280A, or MSB0010718C), PD-L2 (such as, for example, rHIgM12B7), CTLA-4 (such as, for example, Ipilimumab (MDX-010), Tremelimumab (CP-675,206)), IDO, B7-H3 (such as, for example, MGA271, MGD009, omburtamab), B7-H4, B7-H3, T cell immunoreceptor with Ig and ITIM domains (TIGIT)(such as, for example BMS-986207, OMP-313M32, MK-7684, AB-154, ASP-8374, MTIG7192A, or PVSRIPO), CD96, - and T-lymphocyte attenuator (BTLA), V-domain Ig suppressor of T cell activation (VISTA)(such as, for example, JNJ-61610588, CA-170), TIM3 (such as, for example, TSR-022, MBG453, Sym023, INCAGN2390, LY3321367, BMS-986258, SHR-1702, R07121661), LAG-3 (such as, for example, BMS-986016, LAG525, MK-4280, REGN3767, TSR-033, BI754111, Sym022, FS118, MGD013, and Immutep).

Methods of Treating Cancer

The present disclosure also provides methods of treating cancer using the genetically modified cells or compositions.

In one aspect, disclosed herein is a method of treating a cancer compromising administering to a subject a genetically modified cell comprising deletion of the SUSD2 gene or a fragment thereof. In some embodiments, the method comprises a cell comprising a complete deletion of the SUSD2 gene.

In another aspect, disclosed herein is a method of treating a cancer compromising administering to a subject an inhibitor of SUSD2. In one embodiment, the inhibitor of SUSD2 is selected from an antibody, a small molecule, or a nucleic acid. In one embodiment, disclosed herein is a method of treating a cancer compromising administering to a subject an antibody that specifically binds SUSD2.

In some embodiments, the method comprises a cell comprising a deletion of amino acids 1-820 of SEQ ID NO: 1. In some embodiments, the method comprises a cell comprising a deletion of one or more of amino acids of SEQ ID NO: 1.

In some embodiments, the method comprises a cell comprising a deletion of amino acids 1-822 of SEQ ID NO: 2. In some embodiments, the method comprises a cell comprising a deletion of one or more amino acids of SEQ ID NO: 2.

In some embodiments, the method comprises a T cell. In some embodiments, the method comprises a $CD8^+$ T cell. In some embodiments, the method comprises a $CD4^+$ T cell. In some embodiments, the method comprises a natural killer cell. In some embodiments, the method comprises a macrophage.

In some embodiments, the cell is a $\alpha\beta$T cell, $\gamma\delta$T cell, a natural killer T (NKT) cell, a B cell, an innate lymphoid cell (ILC), a cytokine induced killer (CIK) cell, a cytotoxic T lymphocyte (CTL), a lymphokine activated killer (LAK) cell, or a regulatory T cell.

In some embodiments, the method comprises a chimeric antigen receptor (CAR). In some embodiments, the method comprises the cell and an anticancer agent.

In some embodiments, the anticancer agent is an immunotherapeutic agent. In some embodiments, the immunotherapeutic agent is a PD-L1 antibody. In some embodiments, the immunotherapeutic agent is a PD-1 antibody. In some embodiments, the immunotherapeutic agent is a CTLA-4 antibody.

In some embodiments, the anticancer agent is a cytokine. In some embodiments, the cytokine includes, but is not limited to IL-1$\beta$, IL-2, IL-4, IL-6, IL-8, IL-10, IL-12, IL-15, IL-18, IL-21, IL-22, IFN-$\gamma$, TNF-$\alpha$, TGF-$\beta$, LIF, and/or cytotoxins (including, but not limited to perforin and/or granzyme). In some embodiments, the anticancer agent is a chemokine. In some embodiments, the chemokine includes, but is not limited to CCL2, CCL1, CCL19, CCL22, CXCL12, CCL17, MIP-1α, MCP-1. GRO/KC, and/or CXCR3.

In some embodiments, the cancer is a colon adenocarcinoma. In some embodiments, the cancer is a squamous cell carcinoma. In some embodiments, the cancer is an adenosquamous carcinoma. In some embodiments, the cancer is a lymphoma. In some embodiments, the lymphoma is a non-Hodgkin lymphoma. In some embodiments, the lymphoma is a Hodgkin lymphoma. In some embodiments, the lymphoma is a multiple myeloma. In some embodiments, the cancer is a leukemia.

In some embodiments, the cancer includes, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic adenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Administration of Genetically Modified Cells and Compositions

The cells or compositions may be administered in such amounts, time, and route deemed necessary in order to achieve the desired result. The exact amount of the cells or compositions will vary from subject to subject, depending on the species, age, and general condition of the subject, the severity of the infection, the particular composition, its mode of administration, its mode of activity, and the like. The cells or compositions are preferably formulated in dosage unit form for ease of administration and uniformity of dosage. It will be understood, however, that the total daily usage of the cells or compositions will be decided by the attending physician within the scope of sound medical judgment. The specific therapeutically effective dose level for any particular subject will depend upon a variety of factors including the disorder being treated and the severity of the disorder; the activity of the cells or compositions employed; the specific cells or compositions employed; the age, body weight, general health, sex and diet of the patient; the time of administration, route of administration, and rate of excretion of the specific cells or compositions employed; the duration of the treatment; drugs used in combination or coincidental with the specific cells or compositions employed; and like factors well known in the medical arts.

The cells or compositions may be administered by any route. In some embodiments, the composition is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the cells or compositions (e.g., its stability in the environment of the gastrointestinal tract), the condition of the subject (e.g., whether the subject is able to tolerate oral administration), etc.

The exact amount of a cell or composition required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Introduction

Cytokine signaling has been established as an essential mediator promoting CD8$^+$ T cell differentiation and effector functions. For instance, IL-2 was first identified as a growth factor capable of driving the expansion of activated human T cells. IL-2 also regulates the effector and memory responses of CD8$^+$ T cells. Signal transducer and activator of transcription 5 (STAT5) is an essential transcription factor that mediates the production of effector molecules downstream of IL-2 signaling in CD8$^+$ T cells. Deletion of IL-2 or IL-2Rα leads to the loss of expansion of effector and memory CD8$^+$ T cells. However, the therapeutic potential of IL-2 on CD8$^+$ T cell-mediated immunotherapy has been complicated by the essential role of IL-2 on the differentiation of regulatory CD4$^+$ T (Treg) cells, a well-known cell type in immunosuppressive TME. Therefore, enhancement of IL-2 signaling selectively on CD8$^+$ T cells, but not Treg cells, facilitate antitumor response of CD8$^+$ T cells.

The high-affinity IL-2R is a heterotrimeric complex composed of IL-2Rα, IL-2Rβ and common γ chain (encoded by IL2RA, IL2RB and IL2RG gene, respectively). Assembly of IL-2R complex is initiated by the interaction of IL-2 with IL-2Rα, followed by sequential recruitment of IL-2Rβ and γ chain. IL-2Rα contains two sushi domains, which are required for IL-2 binding with IL-2Rα. Previous studies have established an essential role of IL-2Rα in the expansion and functions of effector and memory CD8$^+$ T cells, but not in the priming of naïve CD8$^+$ T cells.

SUSD2 is a single-pass type 1 membrane protein and contains several well-characterized domain structures including a sushi domain at its carboxyl-terminus. Sushi domains are based on a β-sandwich structure, and they have been reported to mediate protein-protein interaction. It has also been shown that the expression of SUSD2 in cancer cells either positively or negatively correlates with tumor growth, depending on the types of cancer. However, the role of SUSD2 in antitumor immune response remains completely unknown.

Example 2. SUSD2 and Targeted Immunotherapy

Figure 1B:
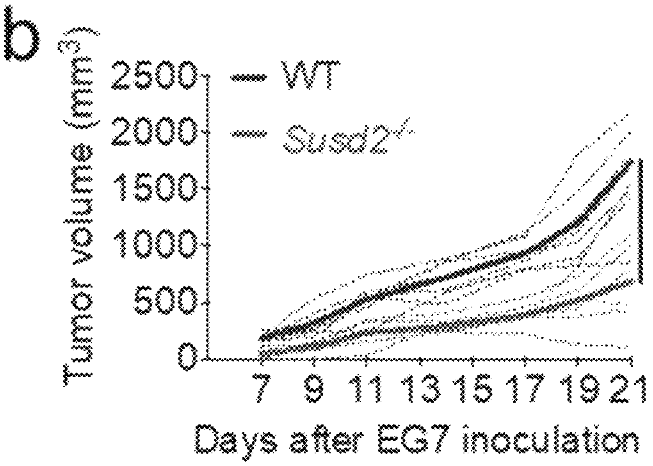
Figure 1C:
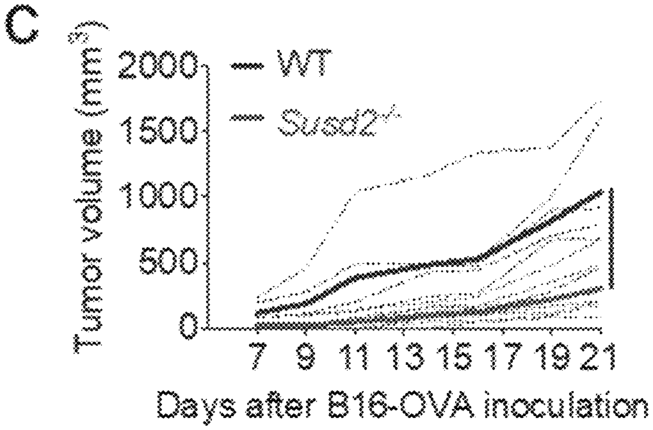
Figure 8A:
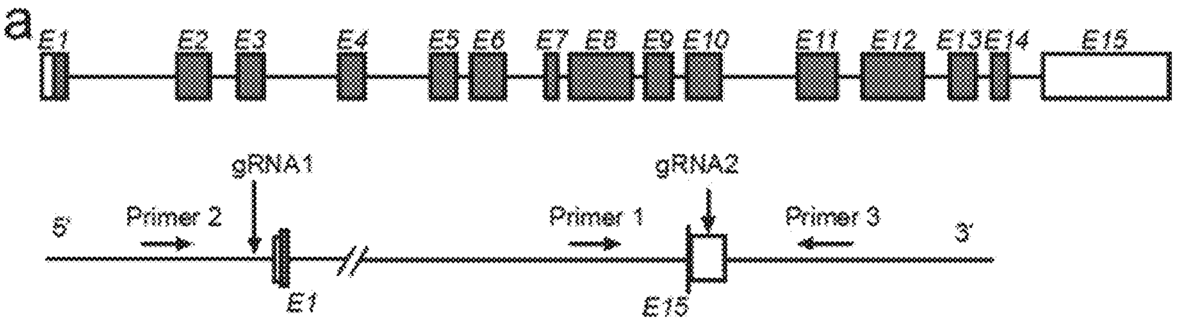
FIGS. 8A-8G show that $Susd2^{-/-}$ mice show no change in global immune cell populations at steady state.
Figure 8B:
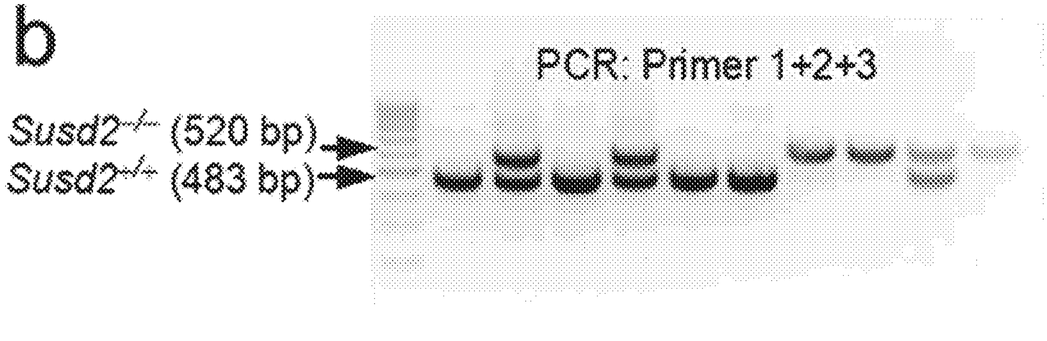
Figure 8C:
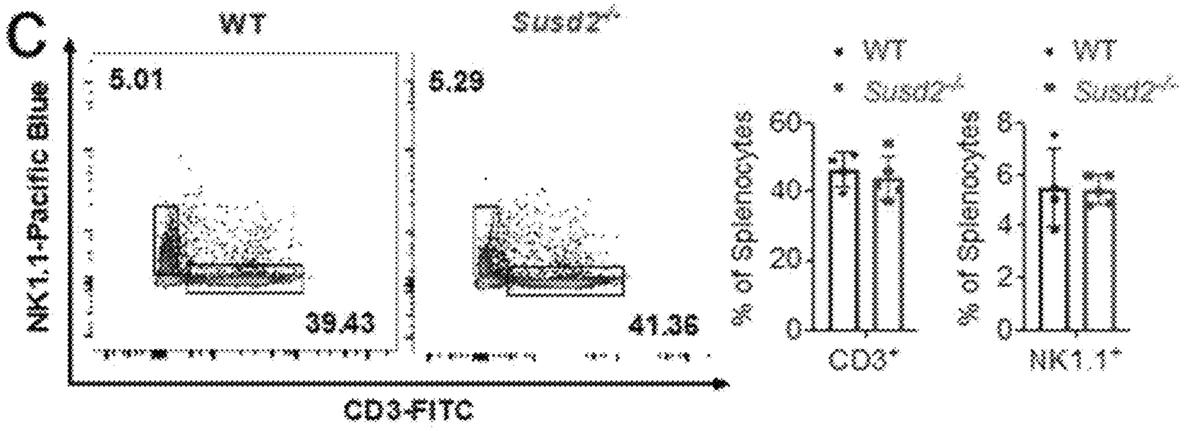
Figure 8D:
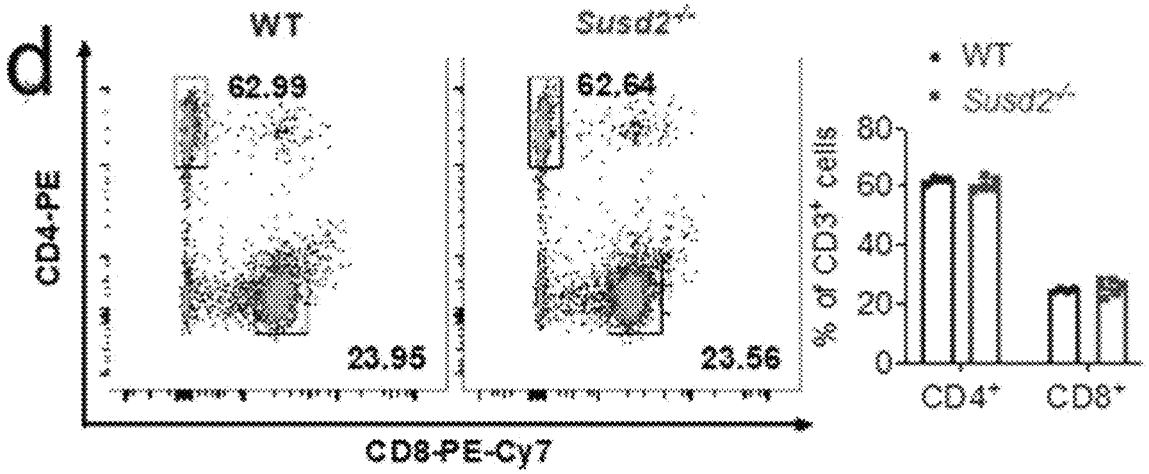
Figure 8E:
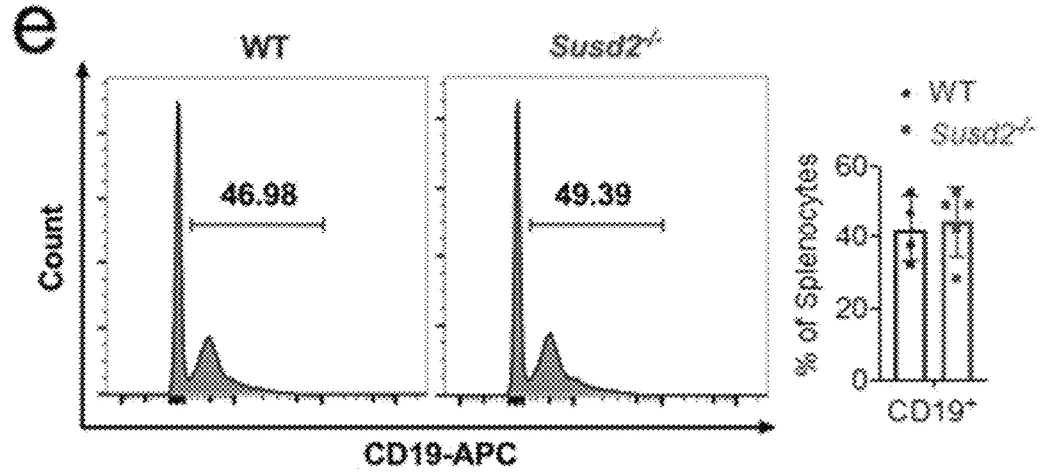
Figure 8F:
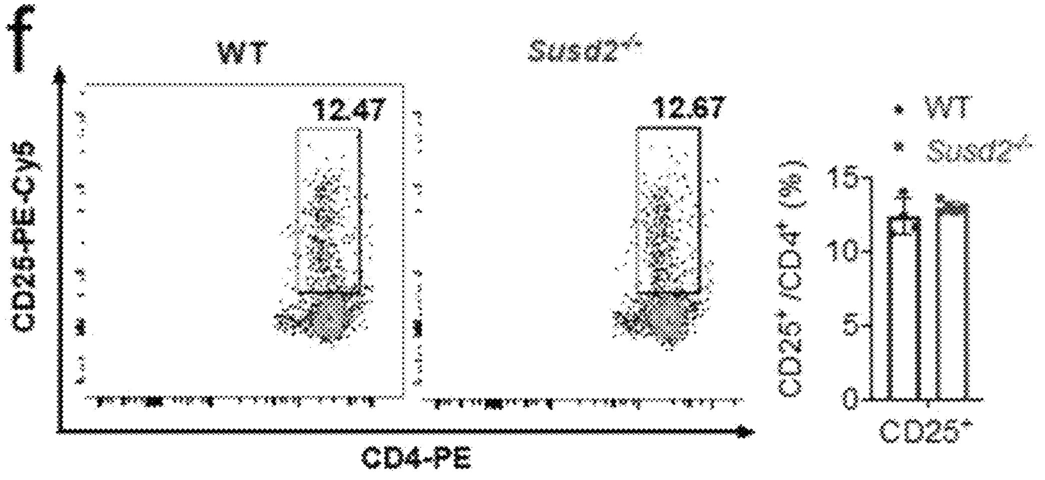
Figure 8G:
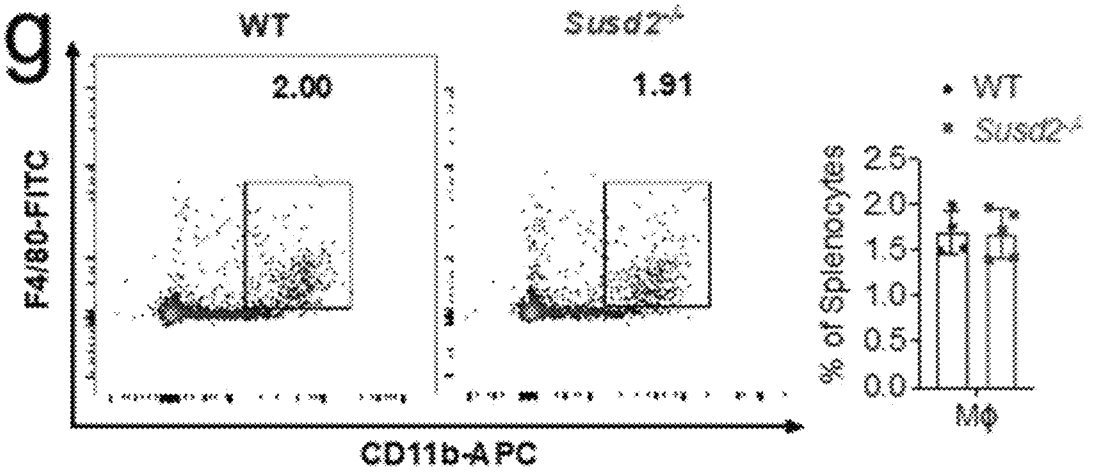
Figure 8H:
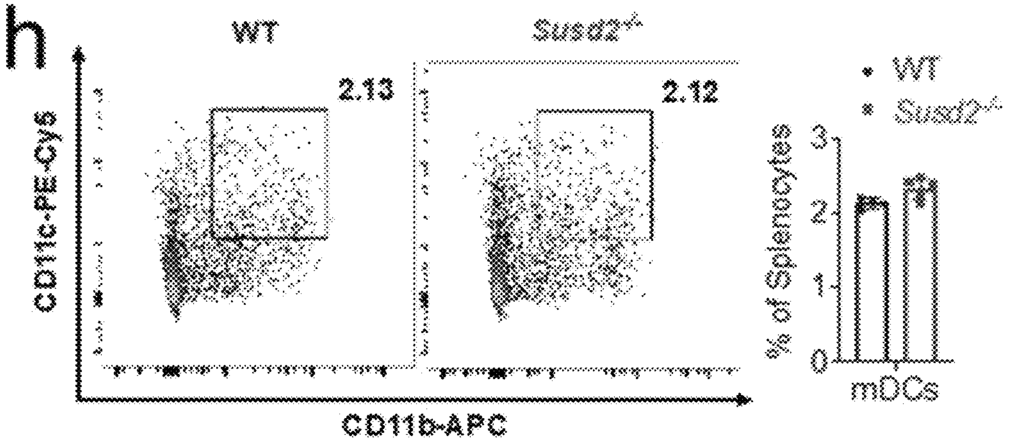
Figure 8I:
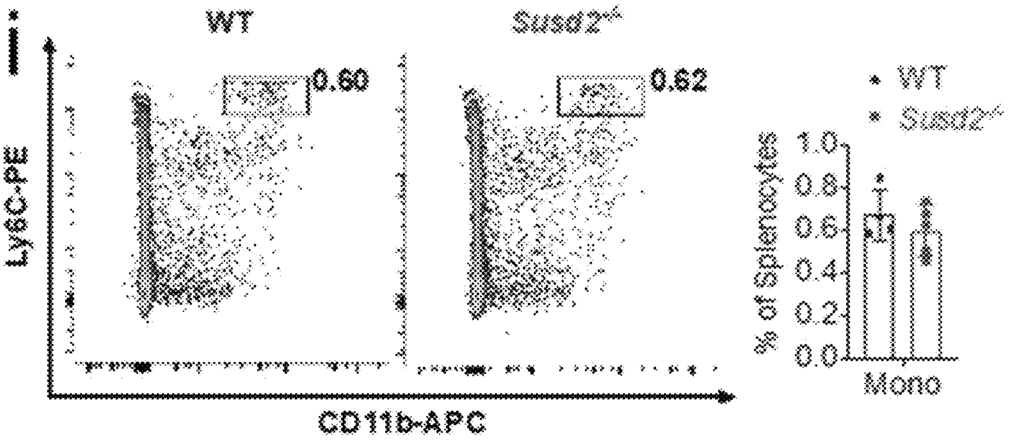
Figure 8J:
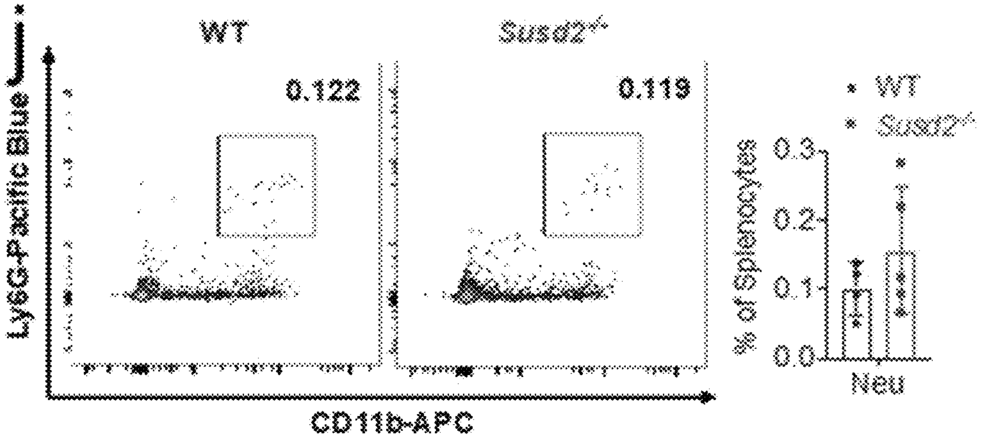

Gene profiling assays found that high expression of SUSD2 correlated with tumor growth in an experimental colitis-associated colorectal cancer model. Susd2$^{-/-}$ mice generated on a C57BL/6 genetic background by deleting all 15 exons of the Susd2 gene (FIG. 8A-8B) had no apparent defects in growth and development, including fertility, breeding, body weight or behavior. Analyses of the adaptive and innate immune system found no alteration in the number of NK1.1$^+$ NK cells, CD3$^+$ CD4$^+$ and CD3$^+$ CD8$^+$ T cells, CD19$^+$ B cells, CD4$^+$CD25$^+$ Treg cells, CD11b$^+$F4/80$^+$ macrophages, CD11b$^+$CD11c$^+$ conventional dendritic cells (DCs), CD11b$^+$Ly6C$^+$monocytes or CD11b$^+$Ly6G$^+$ neutrophils in the spleens of naïve Susd2$^{-/-}$ mice (FIG. 8C-8J), showing no change in global immune cell populations at steady state. In multiple syngeneic mouse tumor models, including allografts of MC38 colorectal cancer (FIG. 1A), EG7 thymoma (FIG. 1B) and ovalbumin-expressing B16 (B16-OVA) melanoma (FIG. 1C) in the right flanks, tumor growth was significantly blunted in Susd2$^{-/-}$ mice compared to wild-type C57BL/6 mice. These observations show that loss of SUSD2 inhibited syngeneic tumor growth.

Figure 1D:
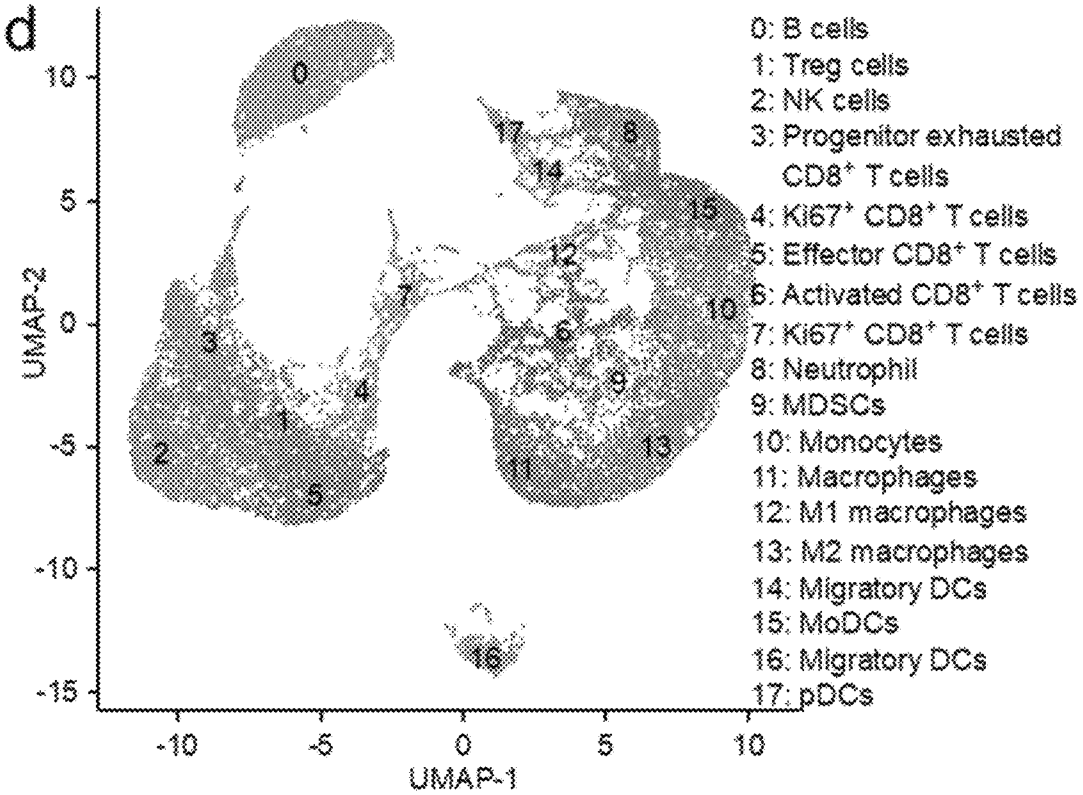
Figure 1E:
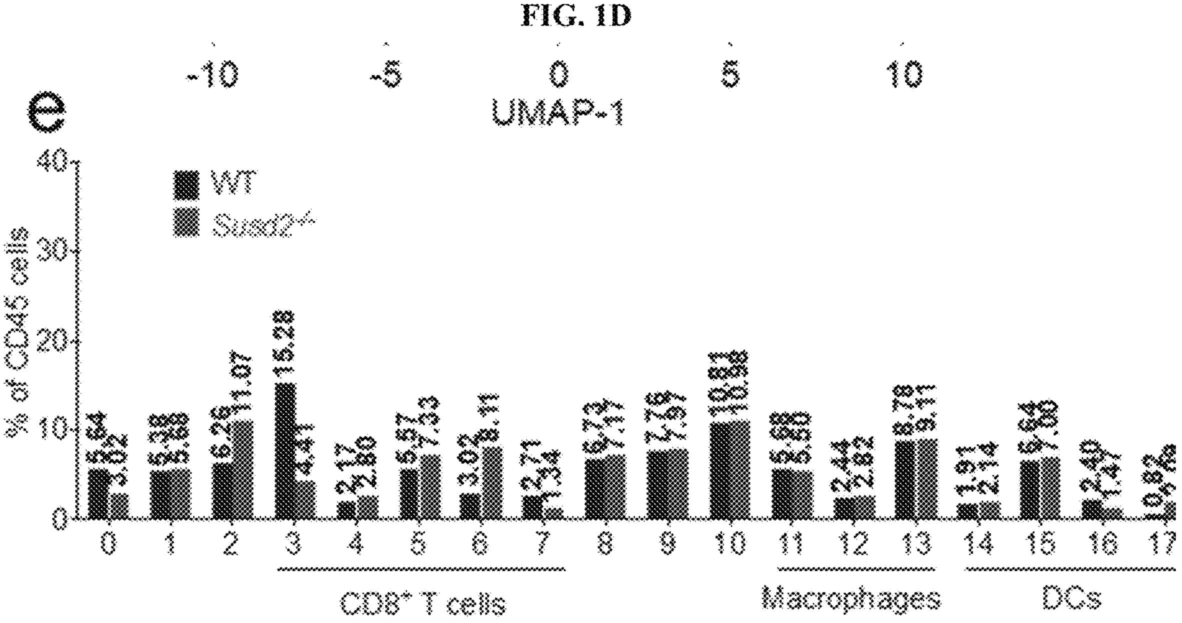
Figure 1F:
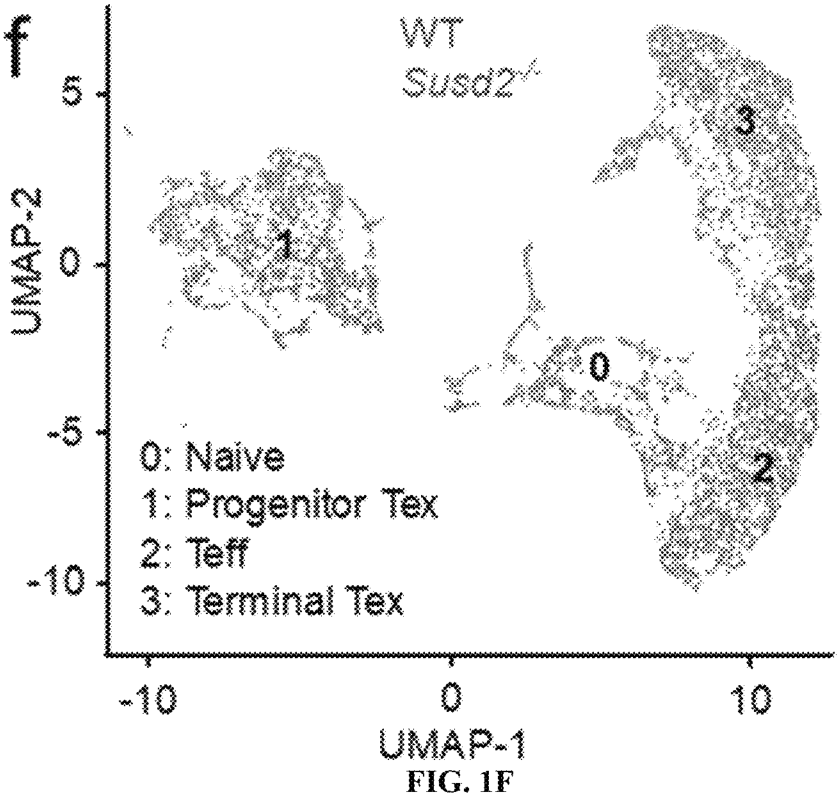
Figure 1G:
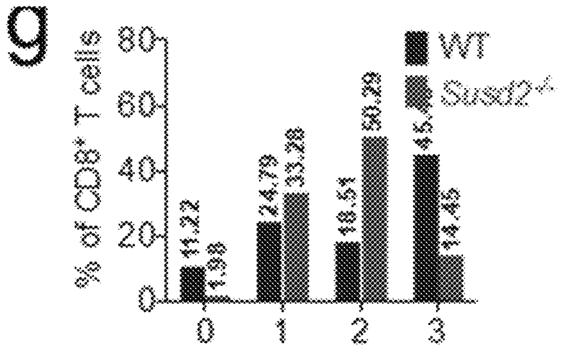
Figure 1H:
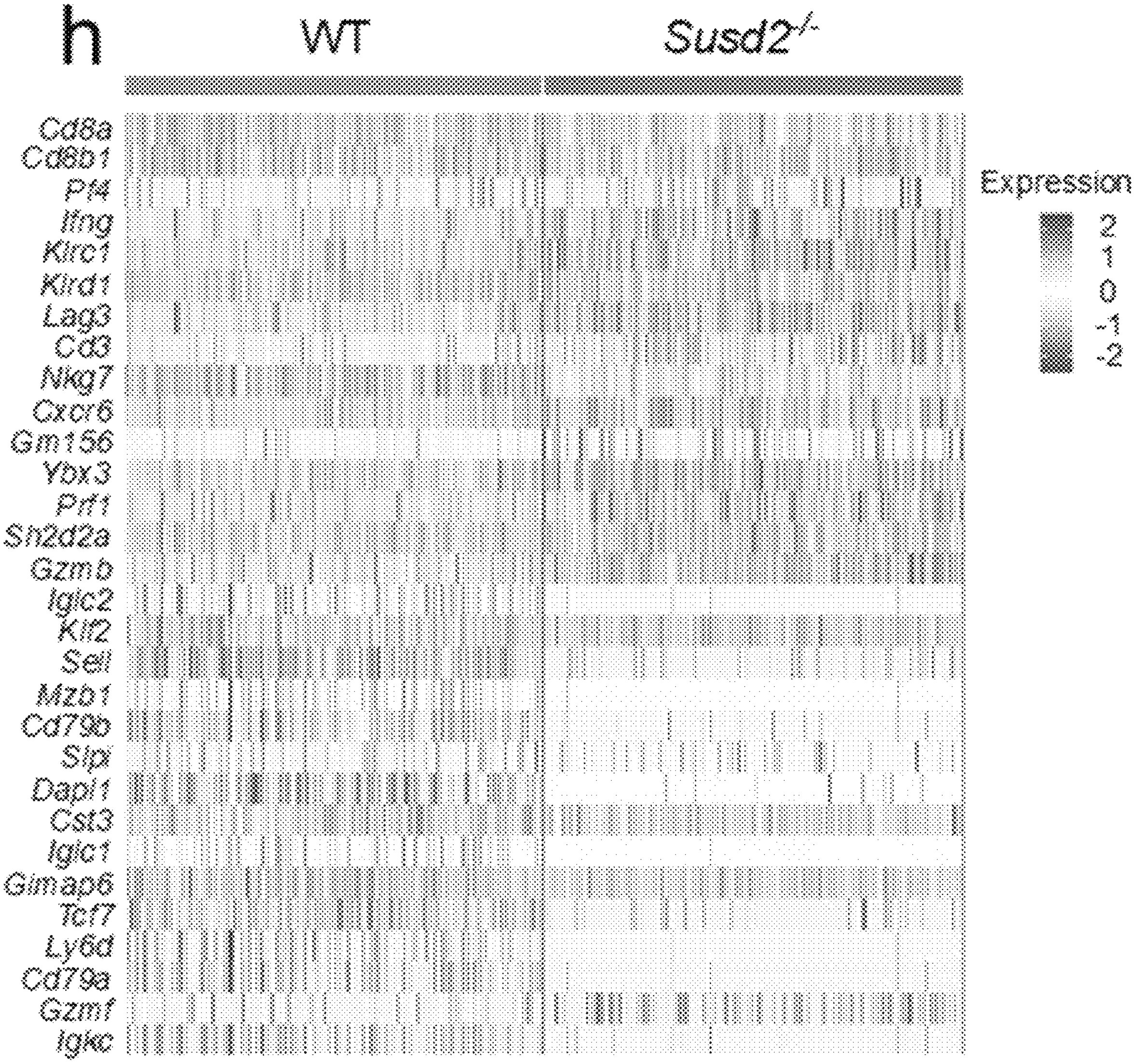
Figure 1I:
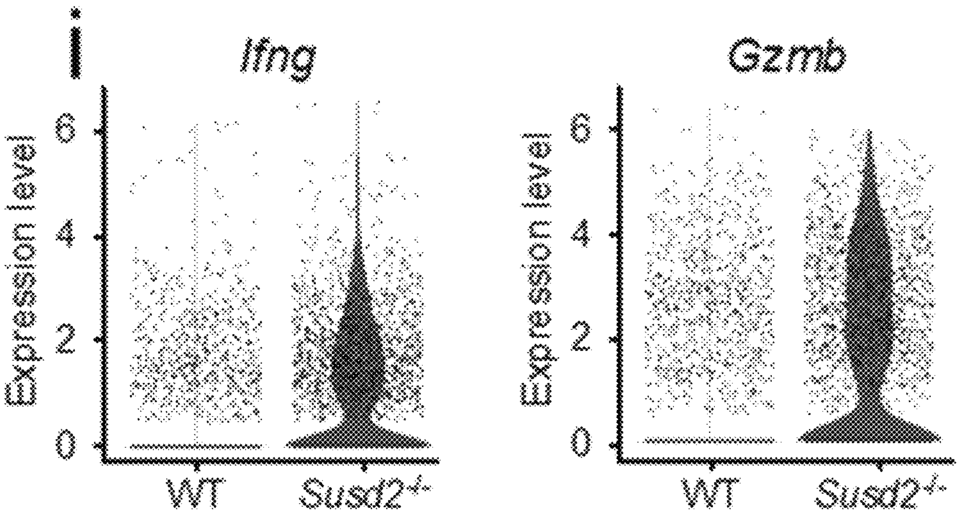
Figure 1J:
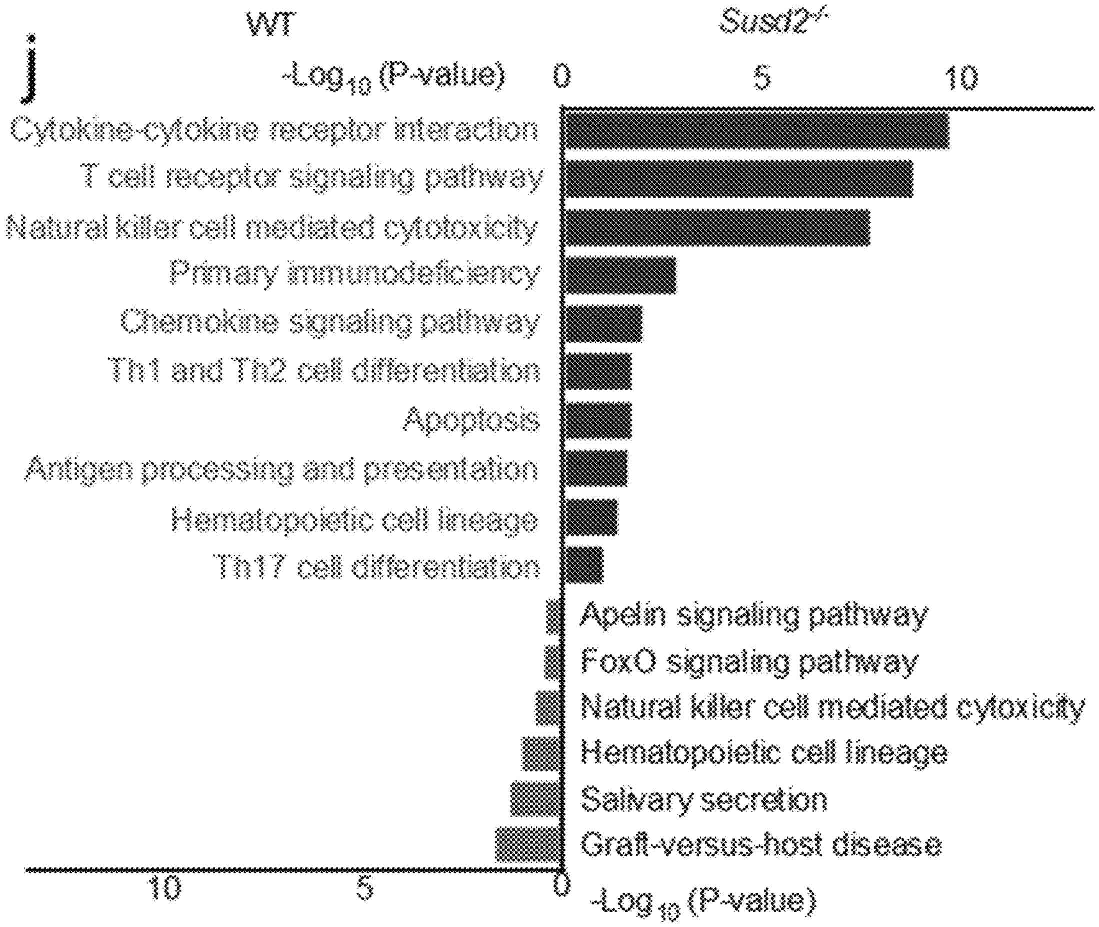
Figure 2A:
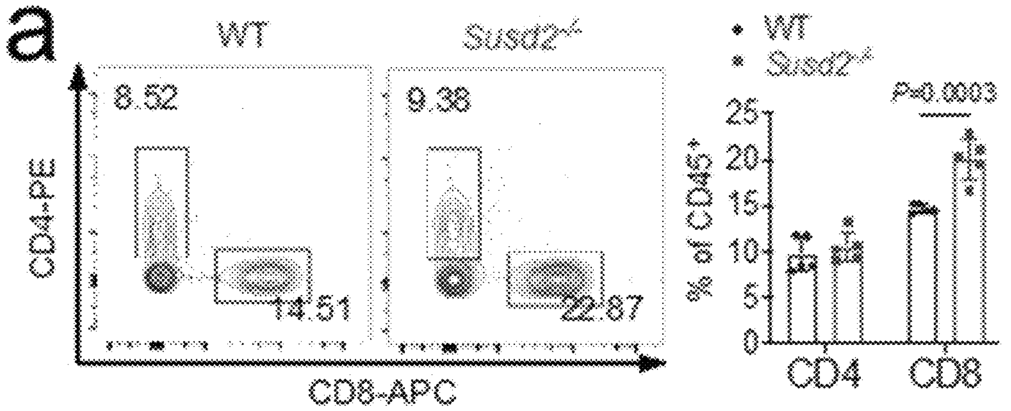
FIGS. 2A-2Q show the enhanced antitumor response in Susd2$^{-/-}$ mice depends on CD8$^+$ cells.
Figure 2B:
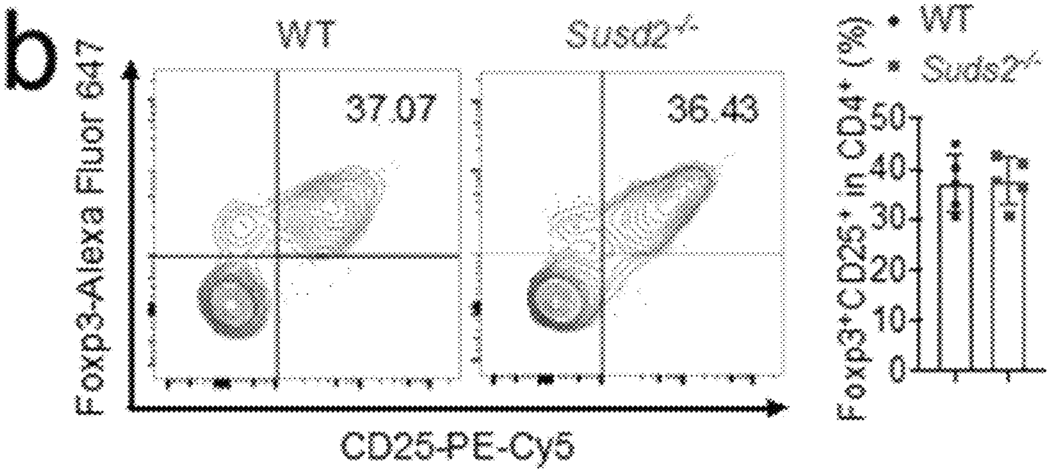
Figure 2C:
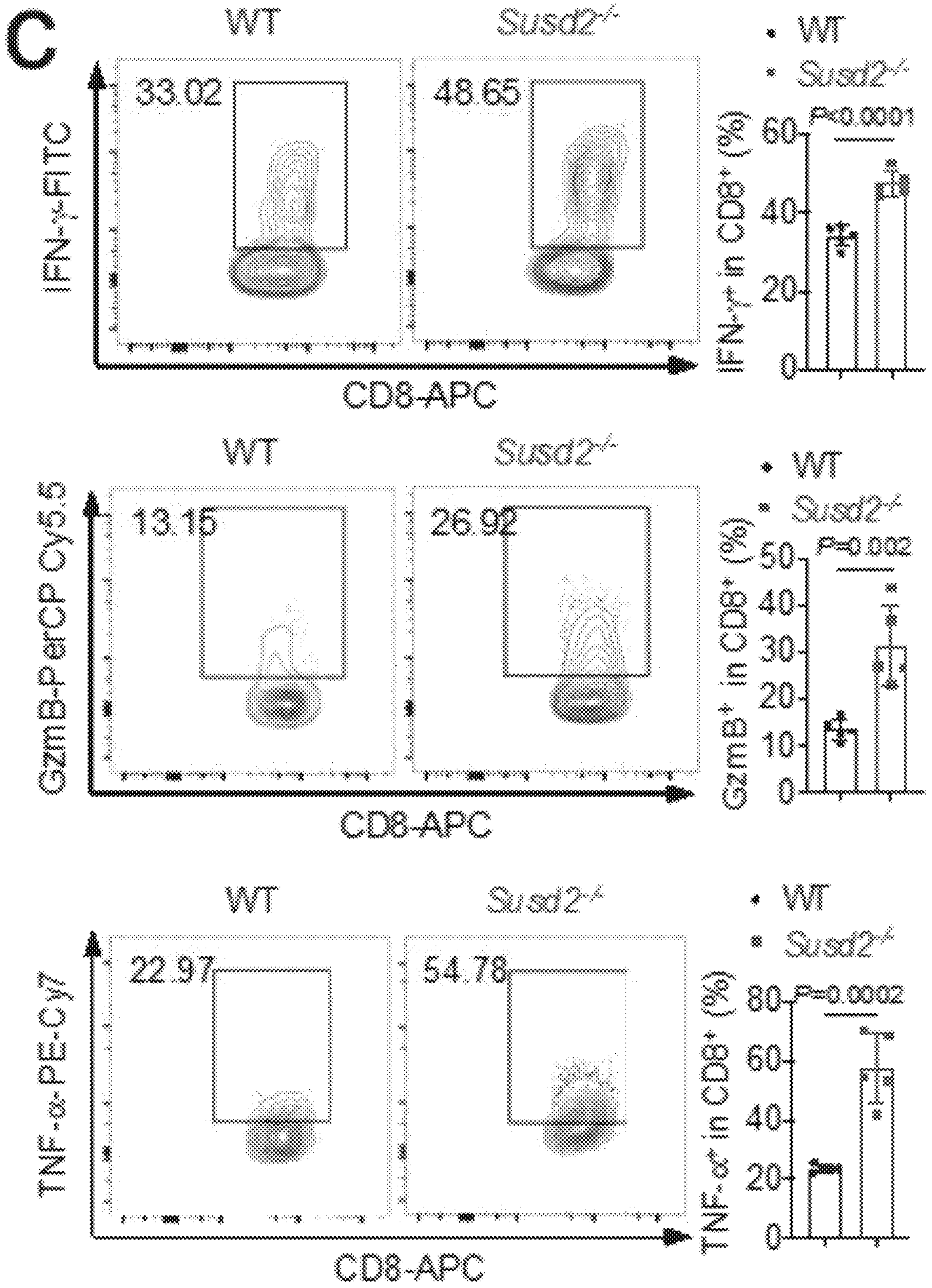
FIGS. 2C-2E show the flow cytometry analysis showing intracellular accumulation of IFN-γ, GzmB, and TNF-expressing intratumoral CD8$^+$ T cells in MC38, EG7, or B16-OVA tumors isolated from WT or Susd2$^{-/-}$ mice at day 18 post-tumor inoculation.
Figure 2D:
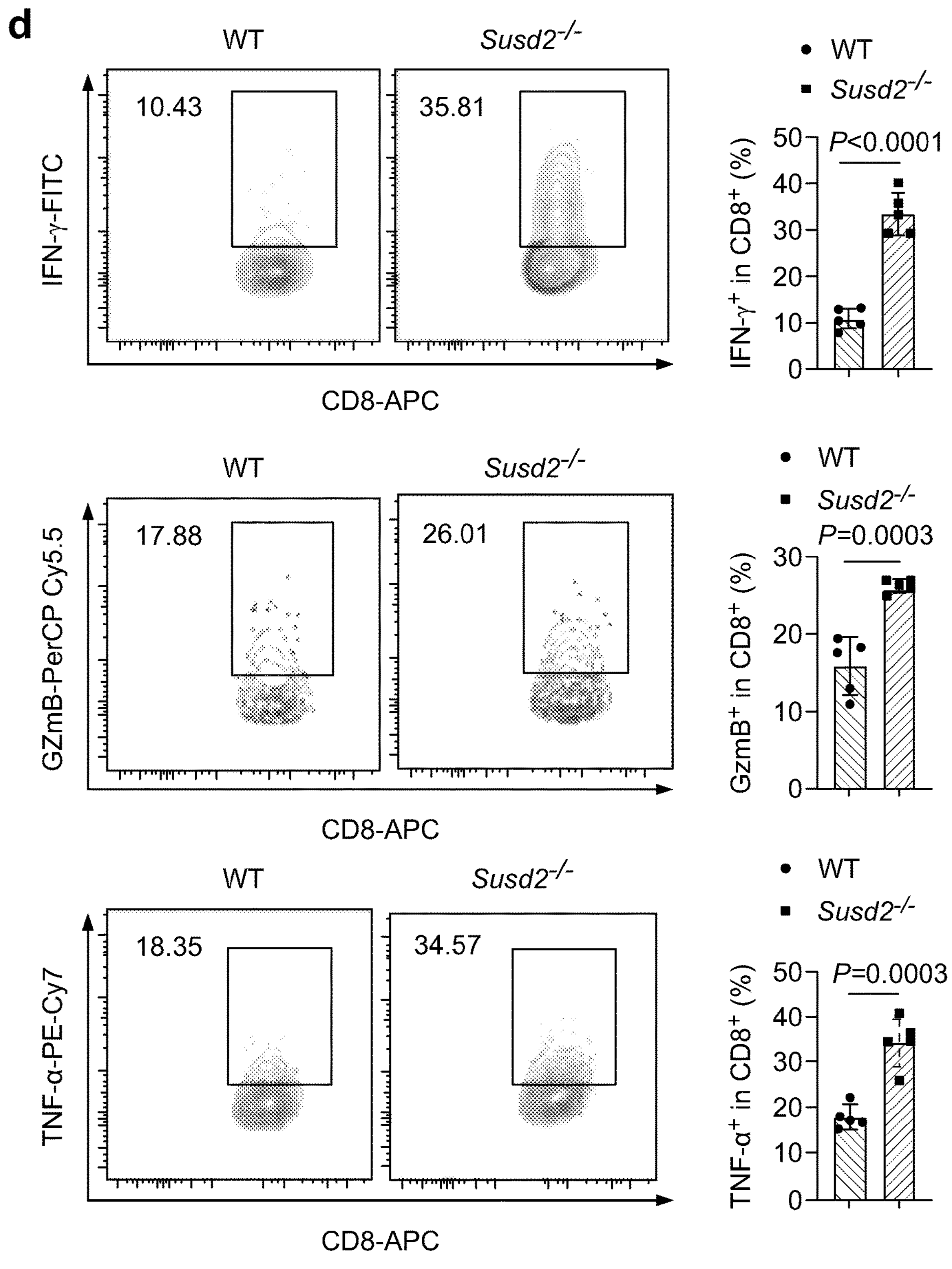
Figure 2E:
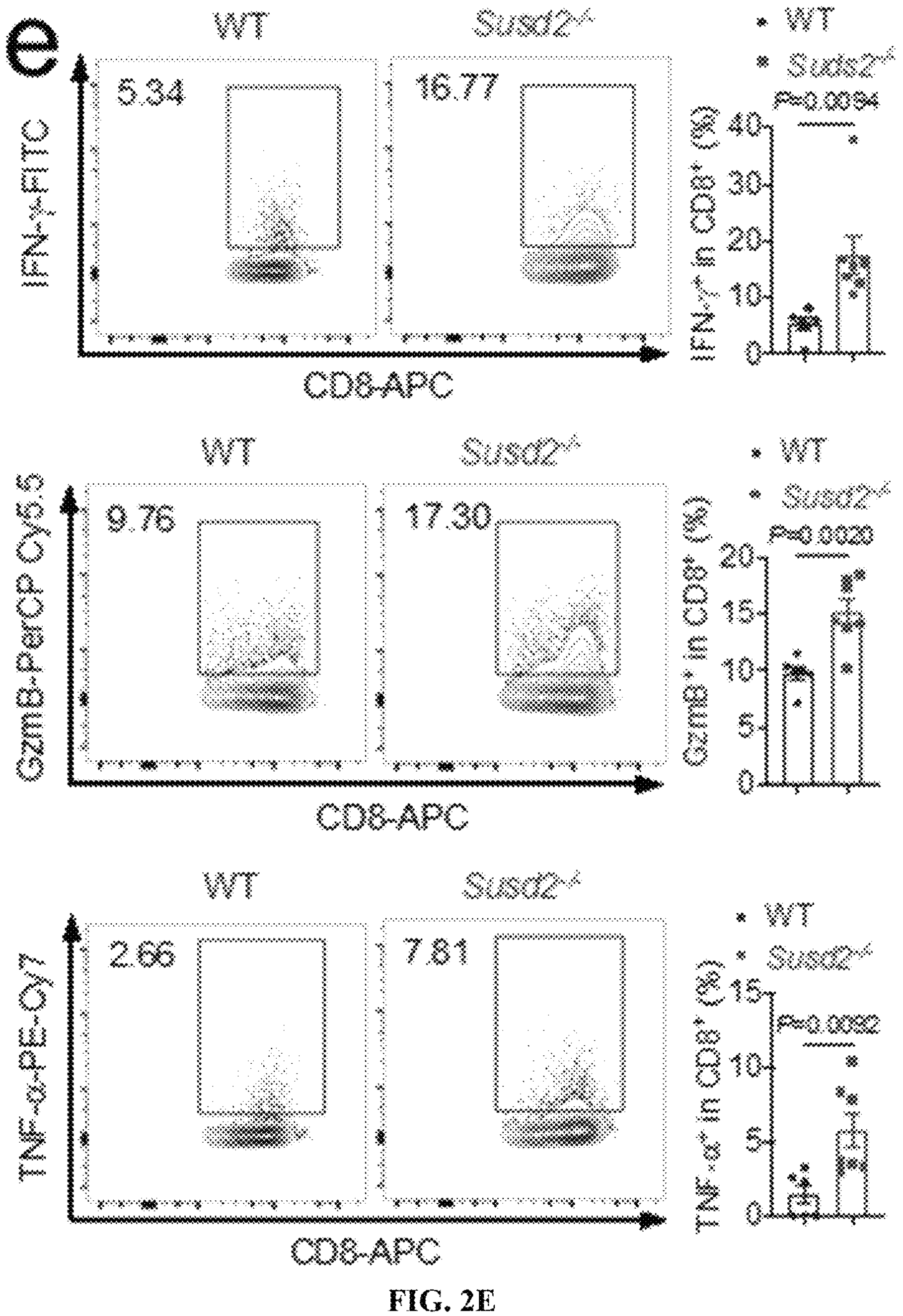
Figure 2F:
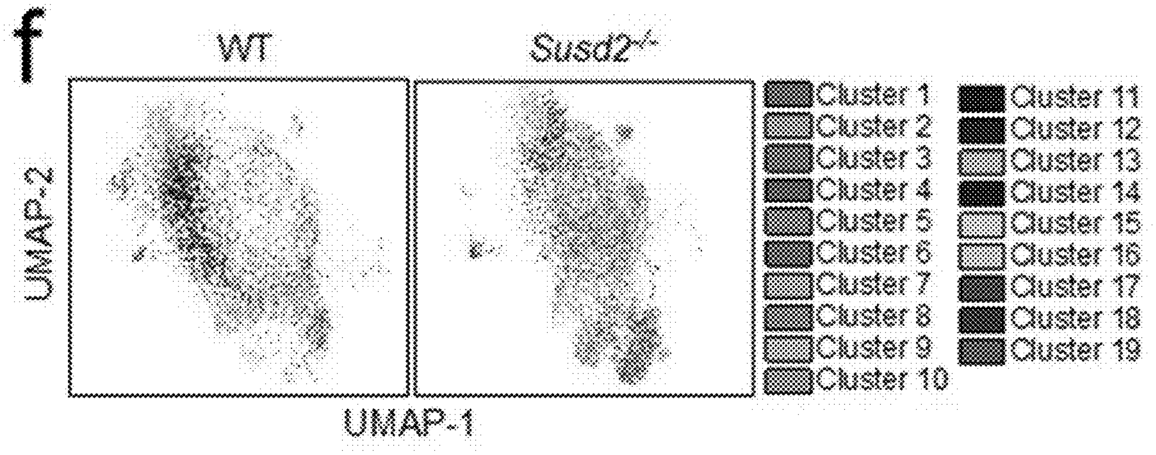
FIGS. 2F-2H shows the UMAP analysis, Volcano plot illustrating differential abundance clusters and cluster-by-marker heatmap characterizing the expression patterns of individual clusters of intratumoral CD8$^+$ T cells from WT and Susd2$^{-/-}$ mice at day 18 post inoculation with MC38.
Figure 2G:
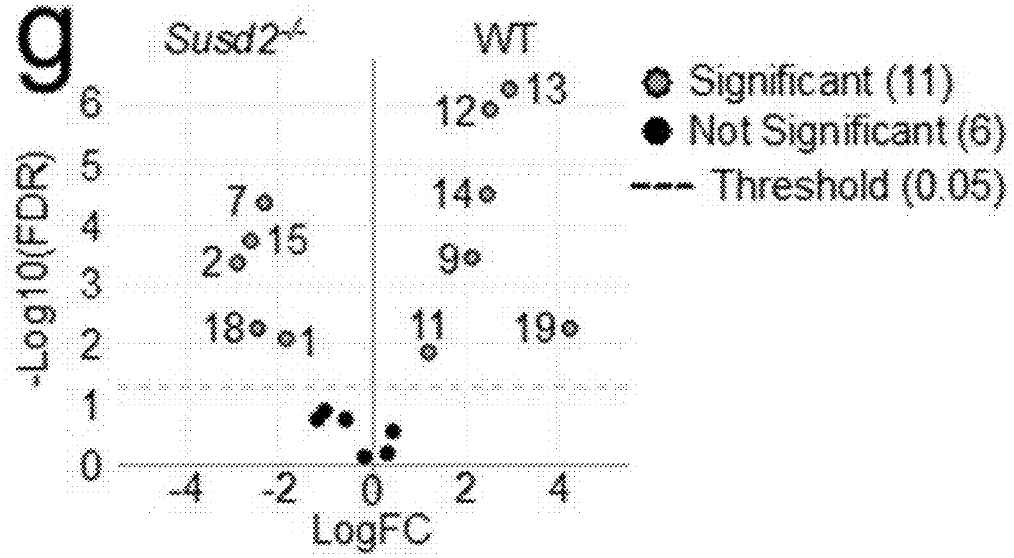
Figure 2H:
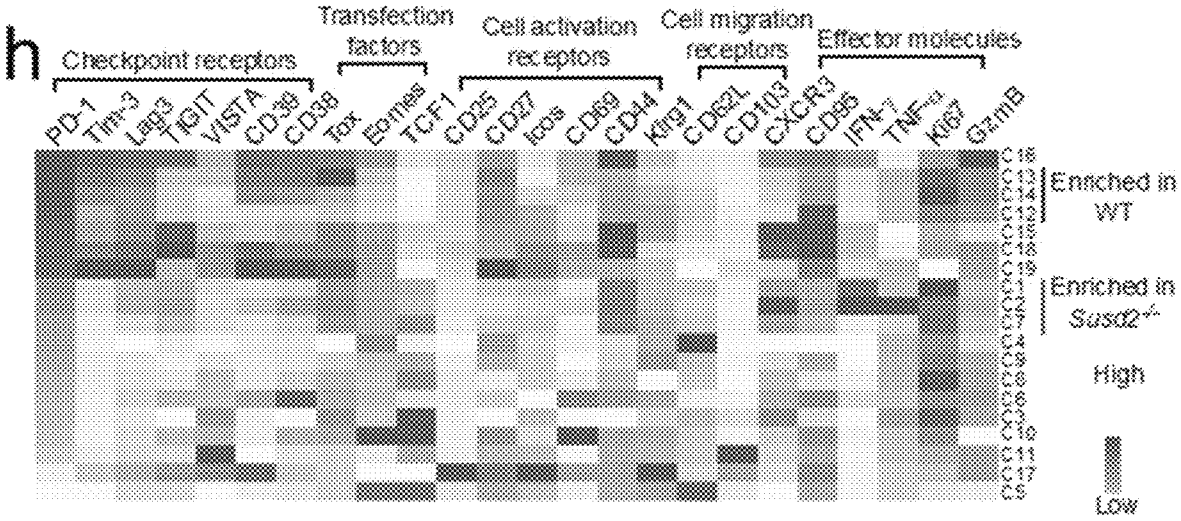
Figure 2I:
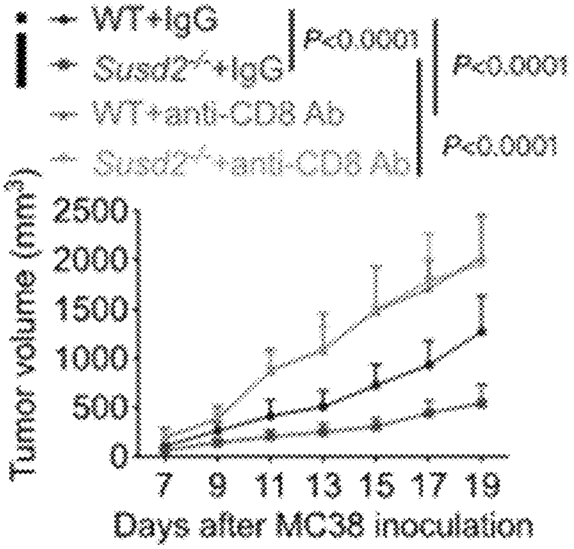
FIG. 2I shows the tumor growth in MC38-tumor bearing WT or Susd2$^{-/-}$ mice injected with either control IgG or CD8 Ab at day 0, 7 and 14 post tumor inoculation.
Figure 9A:
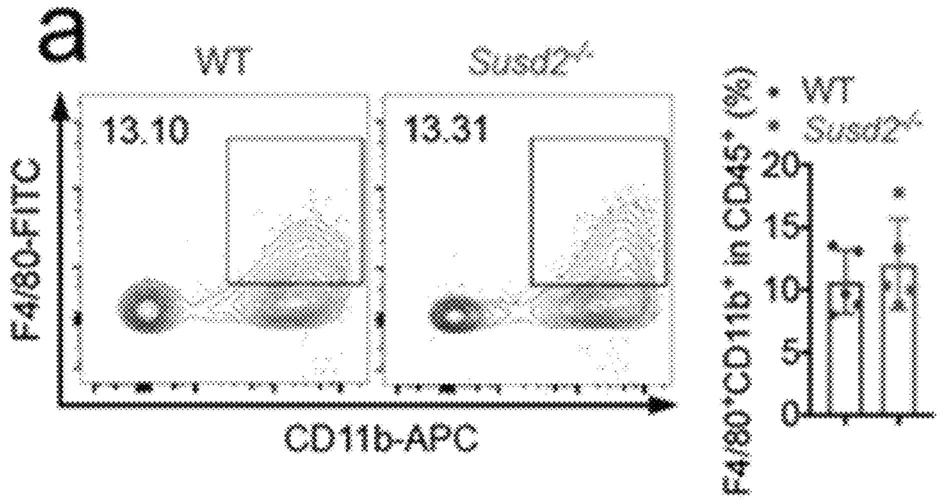
FIGS. 9A-9L show that Susd2 deficiency does not affect intratumoral myeloid cells, NK cells and $CD4^+$ T cells.
Figure 9B:
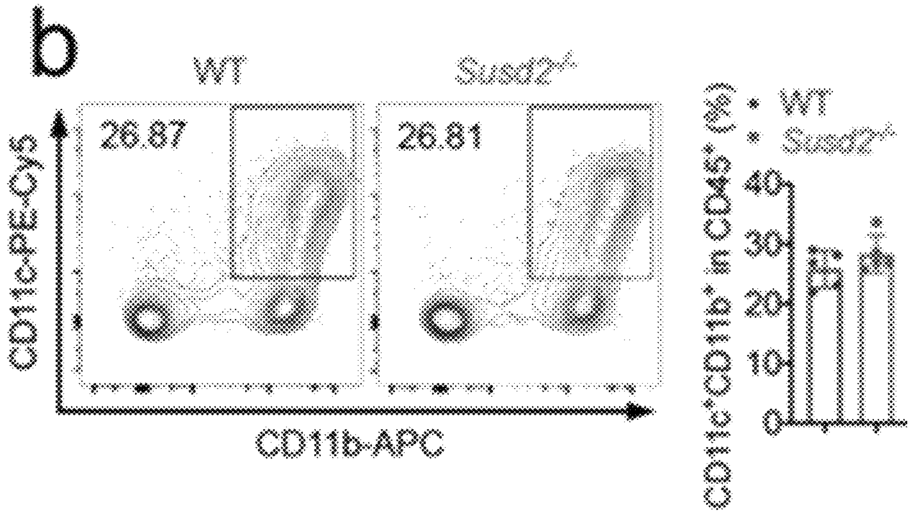
Figure 9C:
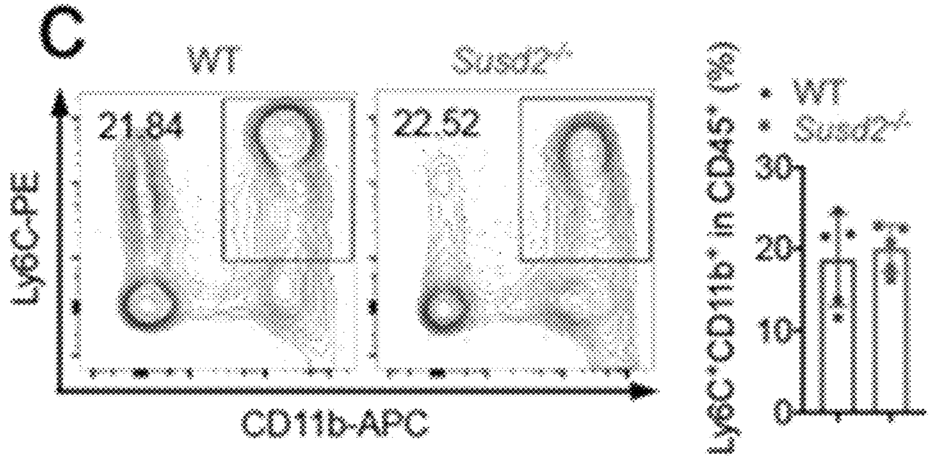
Figure 9D:
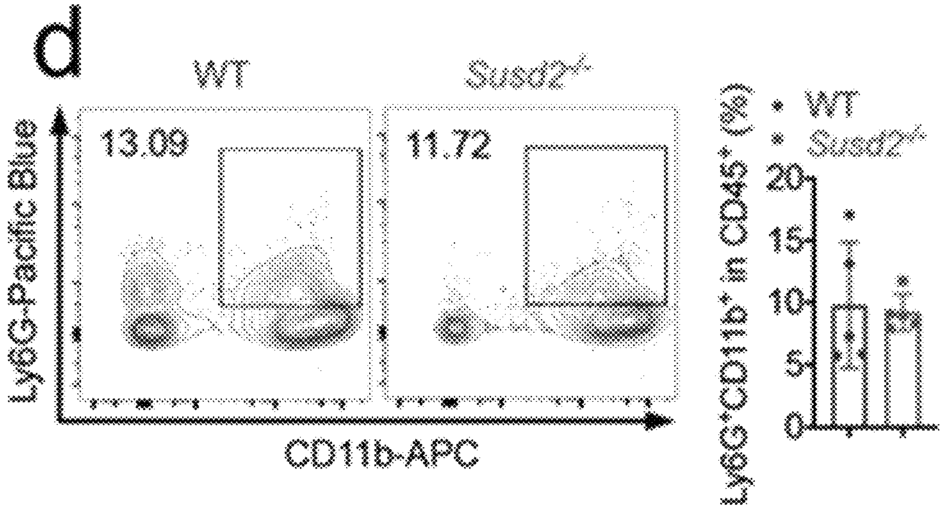
Figure 9E:
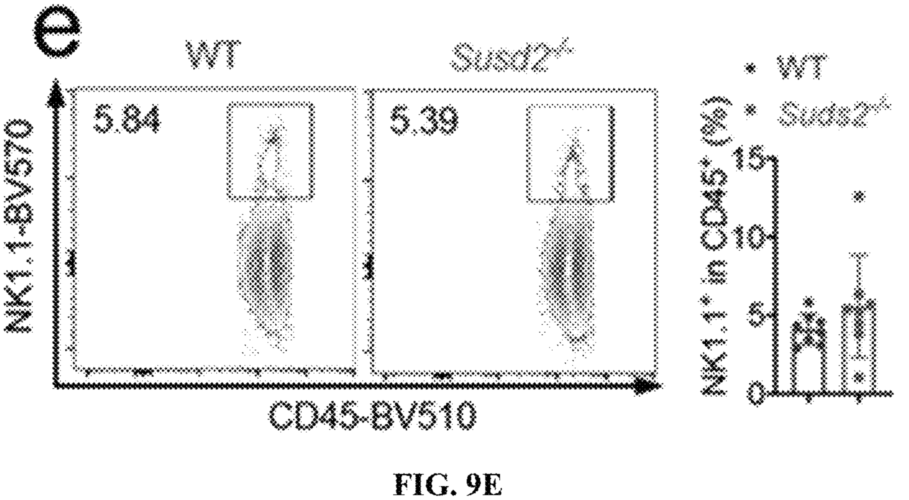
Figure 9F:
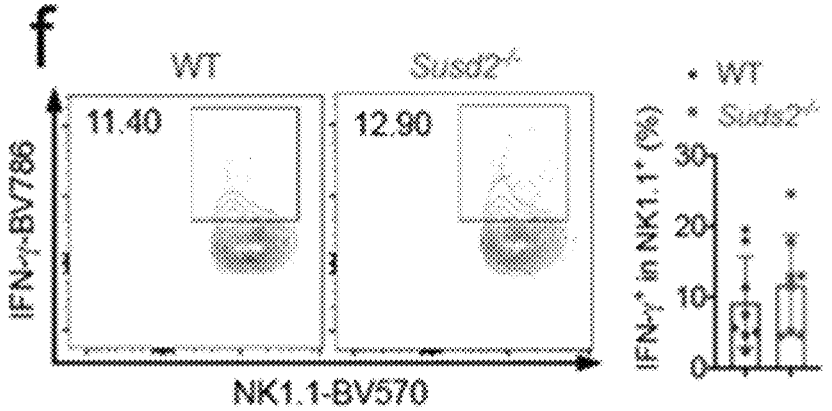
Figure 9G:
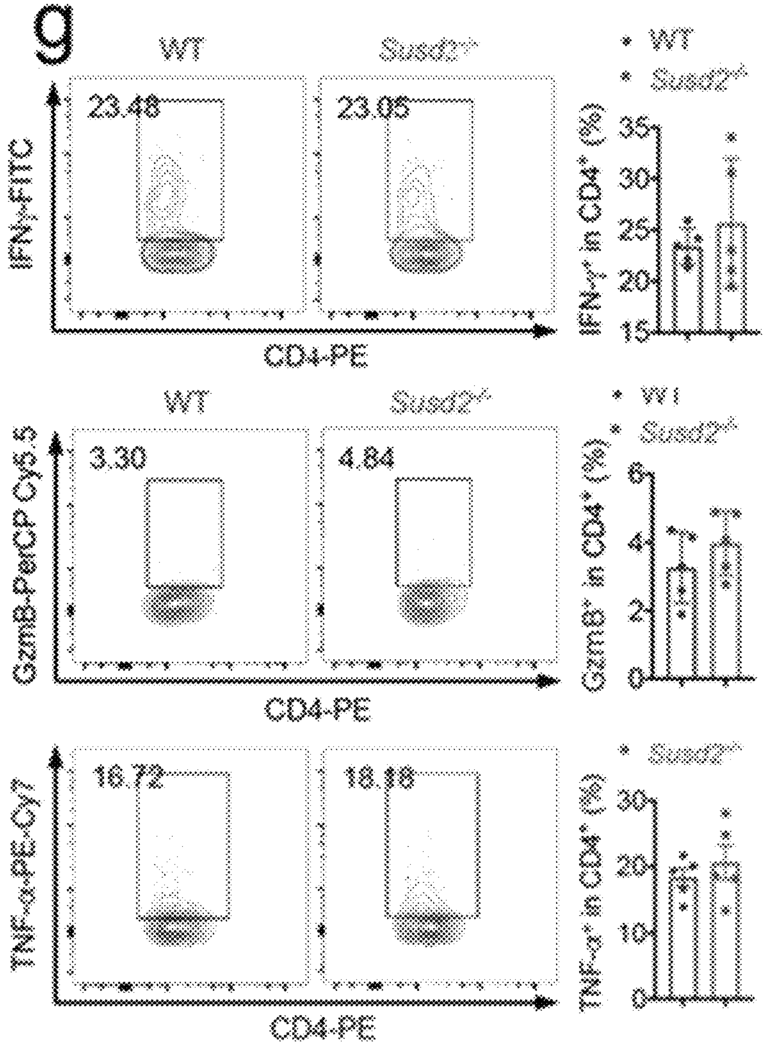
Figure 9H:
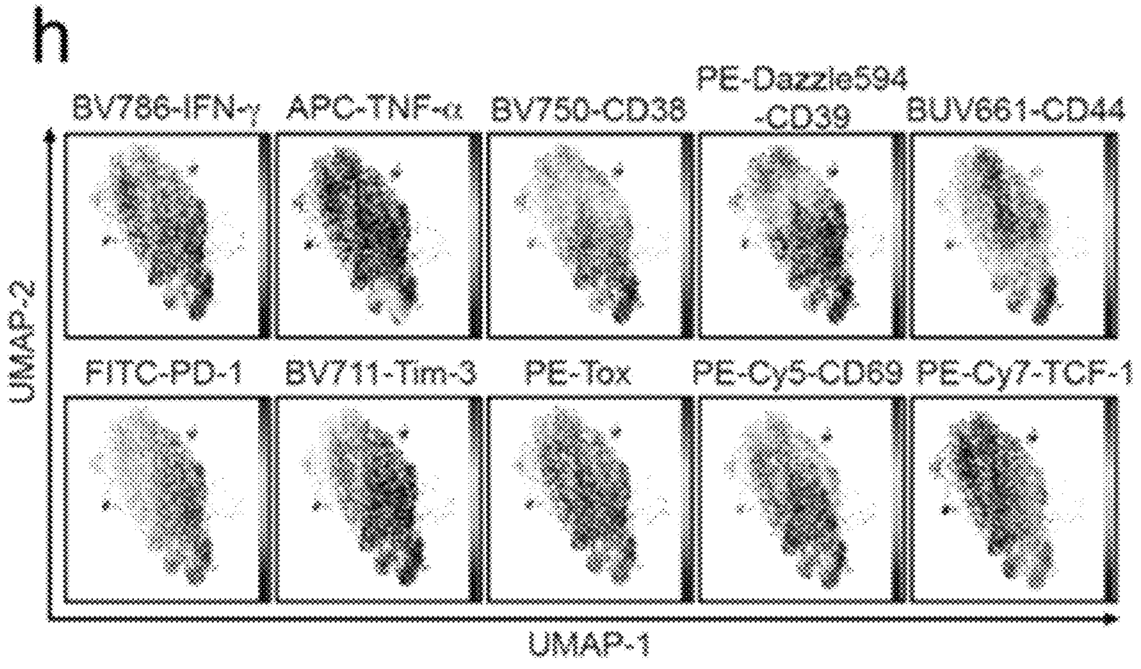
Figure 9I:
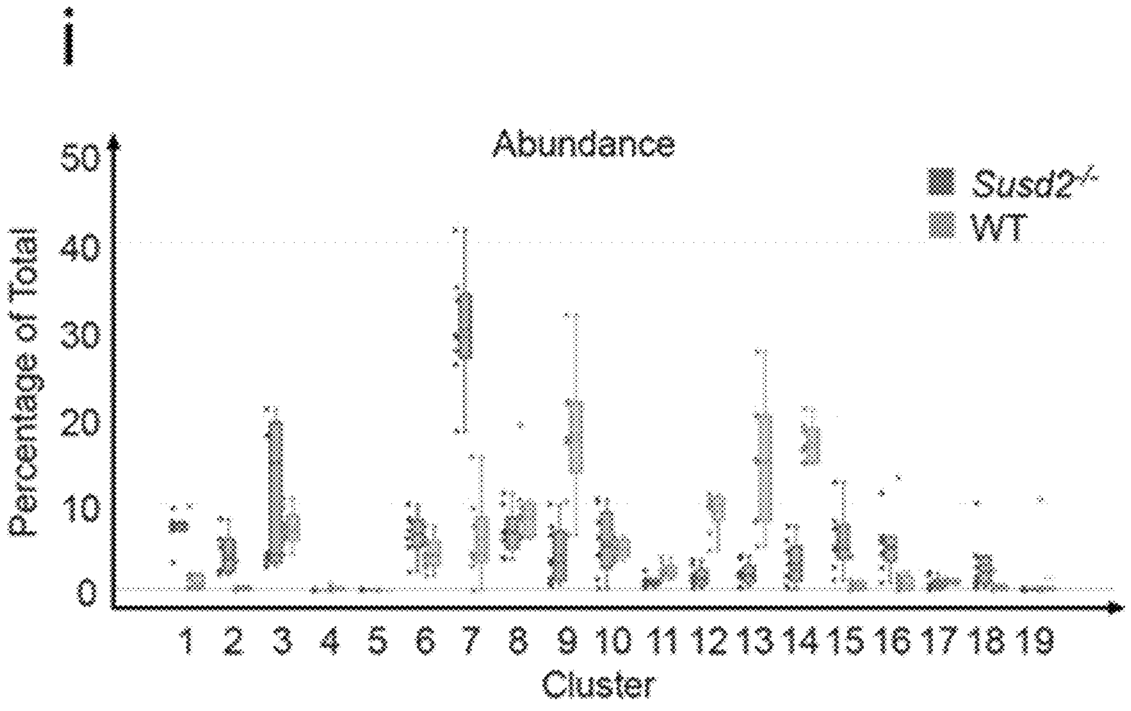

To compare the immune profiles in the TME, single-cell RNA sequencing (scRNA-seq) was performed in CD45$^+$ immune cells isolated from MC38 tumors in wild-type and Susd2$^{-/-}$ mice at day 18 post-inoculation. Unsupervised clustering identified 18 distinctive clusters that represented various immune cell populations, including macrophages, DCs, neutrophils, NK cells, T cells and B cells (FIG. 1D). Among the five clusters representing CD8$^+$ cells (clusters 3-γ), opposite changes were observed between cluster 3 and cluster 6 in Susd2$^{-/-}$ mice compared to wild-type mice (FIG. 1E), showing that SUSD2 might affect the differentiation of intratumoral CD8$^+$ T cell subsets. Sub clustering of CD8$^+$ T cells indicated a substantial increase in Ifng$^+$Gzmb$^+$Cx3cr1$^+$ effector-like T cells (CD8$^+$ TEFF cells, cluster 2) and a decrease in Tcf7$^-$Pdcd1$^+$Havcr2$^+$ Lag3$^+$ terminally exhausted T cells (CD8$^+$ TExT cells, cluster 3) in tumors from Susd2$^{-/-}$ mice compared to those from wild-type mice (FIG. 1F-1G). Decreased Tcf7$^+$Pdcd1-Havcr2$^-$ naïve T cells (CD8$^+$ TN cells, cluster 0) and slightly increased Tcf7$^+$ Pdcd1$^+$Havcr2-Lag3$^-$ progenitor exhausted T cells (CD8$^+$ TExP cells, cluster 1) were detected in tumors from Susd2$^{-/-}$ mice compared to those from wild-type mice (FIG. 1F-1G). Further examination of gene signature in CD8$^+$ cells showed increased expression of various genes encoding T cell effector molecules, such as Gzmb and Ifng in Susd2$^{-/-}$ CD8$^+$ cells compared to wild-type CD8$^+$ cells (FIG. 1H-1I). Pathway enrichment analysis discovered higher expression of genes involved in multiple antitumor immunity-related pathways, such as cytokine-cytokine receptor interaction, in Susd2$^{-/-}$ CD8$^+$ cells compared to wild-type CD8$^+$ T cells (FIG. 1J). These findings showed that SUSD2 deficiency led to an enhanced differentiation of CD8$^+$ TEFF cells and reduced transition to CD8$^+$ TExT cells in the TME, which correlate with an improved control of tumor growth. Flow cytometry analysis of MC38 tumors at day 18 post-inoculation indicated the frequencies of immune cells, including CD11b$^+$ F4/80$^+$macrophages CD11b$^+$CD11c$^+$ DCs, CD11b$^+$Ly6C$^+$ monocytes, CD11b$^+$Ly6G$^+$ neutrophils and NK1.1$^+$ NK cells, among the CD45$^+$ tumor-infiltrating leukocytes were similar between wild-type and Susd2$^{-/-}$ mice (FIG. 9A-9E). In contrast, a significantly increased percentage of CD8$^+$ T cells (20% versus 14% of CD45$^+$ cells), but not CD4$^+$ T cells or Foxp3$^+$ Treg cells, were detected in M38 tumors in Susd2$^{-/-}$ compared to wild-type C57BL/6 mice (FIG. 2A-2B). The production of IFN-γ, GzmB and TNF was significantly enhanced in intratumoral CD8$^+$ T cells from Susd2$^{-/-}$ mice compared to wild-type mice (FIG. 2C), while intratumoral NK cells generated similar amounts of IFN-7 and CD4$^+$ T cells generated similar amounts of IFN-γ, GzmB and TNF in Susd2$^{-/-}$ mice and wild-type mice (FIGS. 9F and 9G), showing an elevated antitumor immune response uniquely in Susd2$^{-/-}$ CD8$^+$ T cells. Enhanced production of IFN-γ, GzmB and TNF in intratumoral Susd2$^{-/-}$ CD8$^+$ T cells compared to wild-type CD8$^+$ T cells was also observed in mice challenged with EG7 or B16-OVA cells (FIG. 2D-2E). Multi-dimensional flow cytometry assay with a panel of 32 lineage- and T-cell state specific markers showed that Susd2$^{-/-}$ CD8$^+$ T cells localized substantially more in subcluster 1 and subcluster 2, which were defined as CD8$^+$ TEFF cells based on the enriched expression of IFN-γ, TNF, CXCR3 and KLRG1, and less in subclusters 12, 13, 14 and 19, which were defined as CD8$^+$ TExT cells, based on the high expression of Tim-3, TOX, Lag3, CD38 and CD39, compared to wild-type CD8$^+$ T cells (FIGS. 9H and 9I). Susd2$^{-/-}$ CD8$^+$ T cells were also significantly increased in subcluster 7, which was defined as TCF1$^{hi}$PD-1$^+$ Tim-3$^-$ CD8$^+$ TExP cells (FIG. 2G-2H). Depletion of CD8$^+$ T cells completely abolished the improved control of MC38 tumor growth in Susd2$^{-/-}$ mice compared to wild-type mice (FIG. 2I), showing that enhanced CD8$^+$ TEFF cell function was a key contributor to the control of tumor growth in Susd2$^{-/-}$ mice.

Figure 2J:
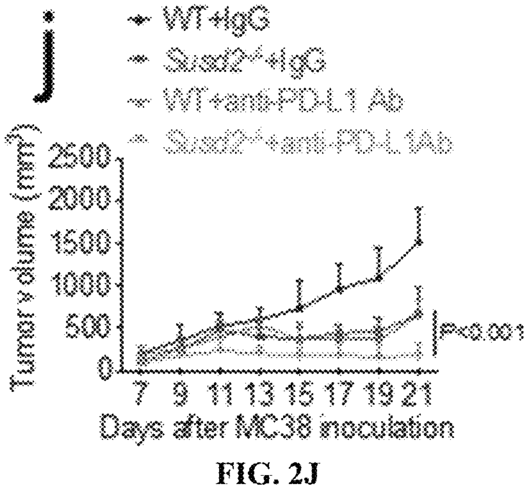
FIG. 2J-2L shows the tumor growth and survival in WT and Susd2$^{-/-}$ mice bearing either MC38, EG7, or B16-F10 tumor cells injected with either control IgG or PD-L1 Ab at day 7, 10 and 13 after tumor inoculation.
Figure 2K:
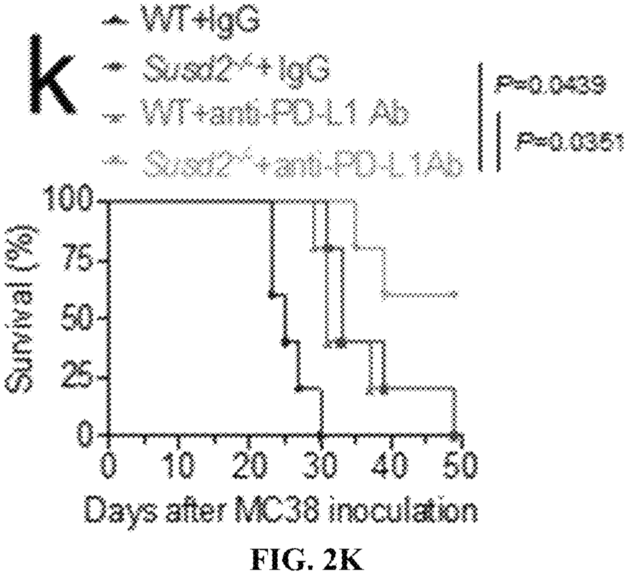
Figure 2L:
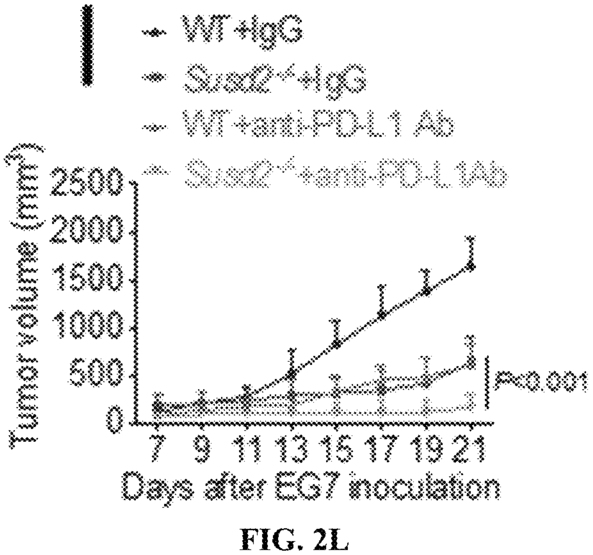
Figure 2M:
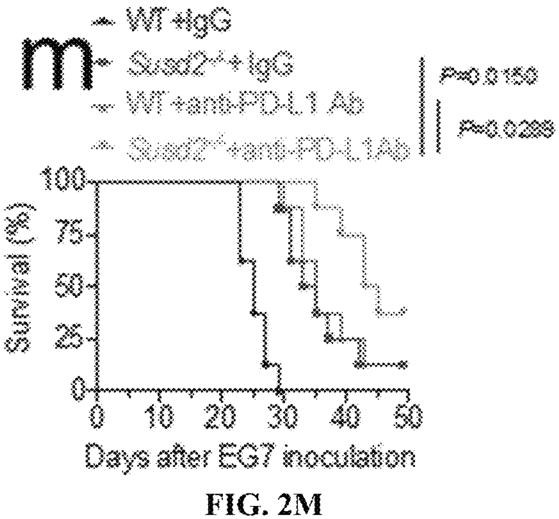
Figure 2N:
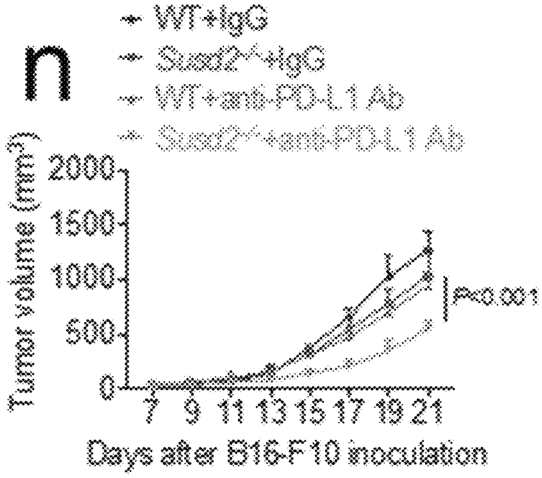
Figure 2O:
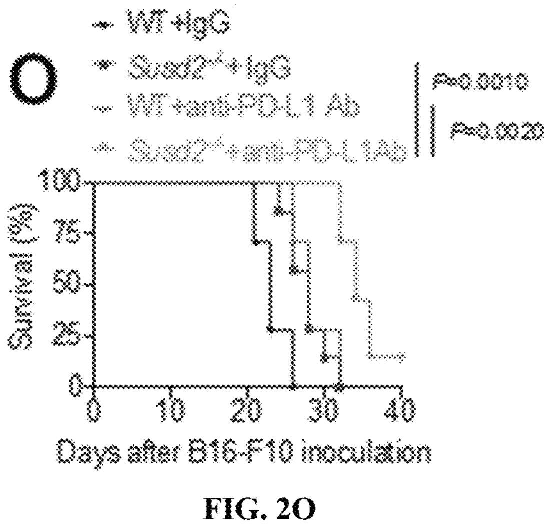
Figure 2P:
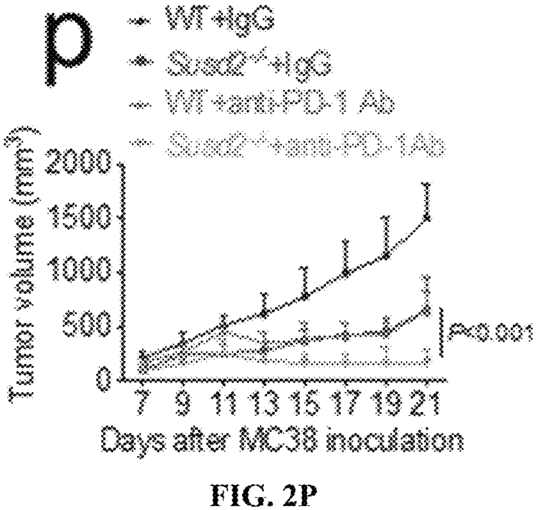
Figure 2Q:
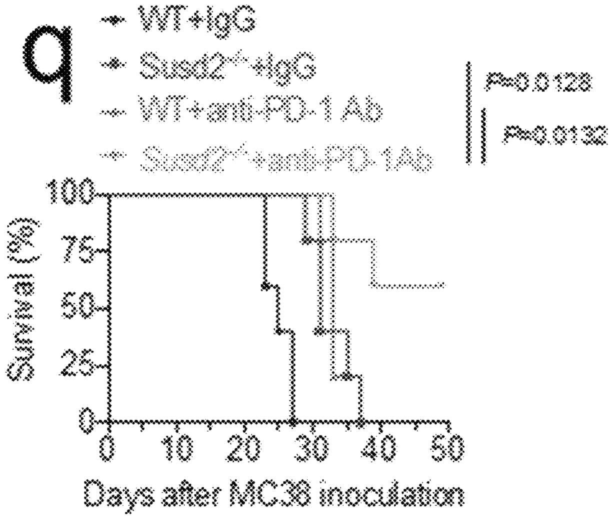
Figure 9J:
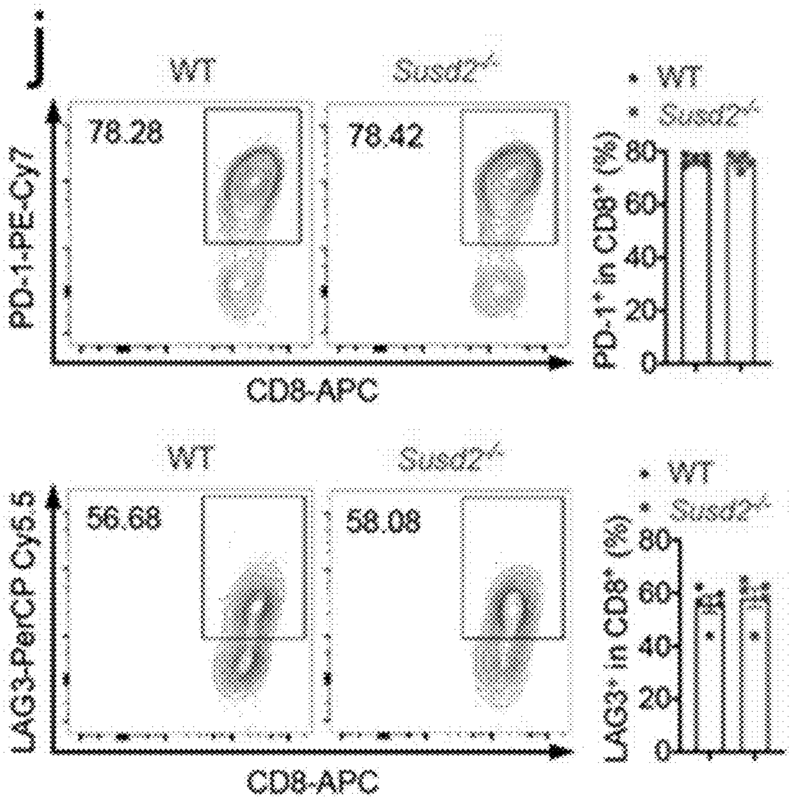
Figure 9K:
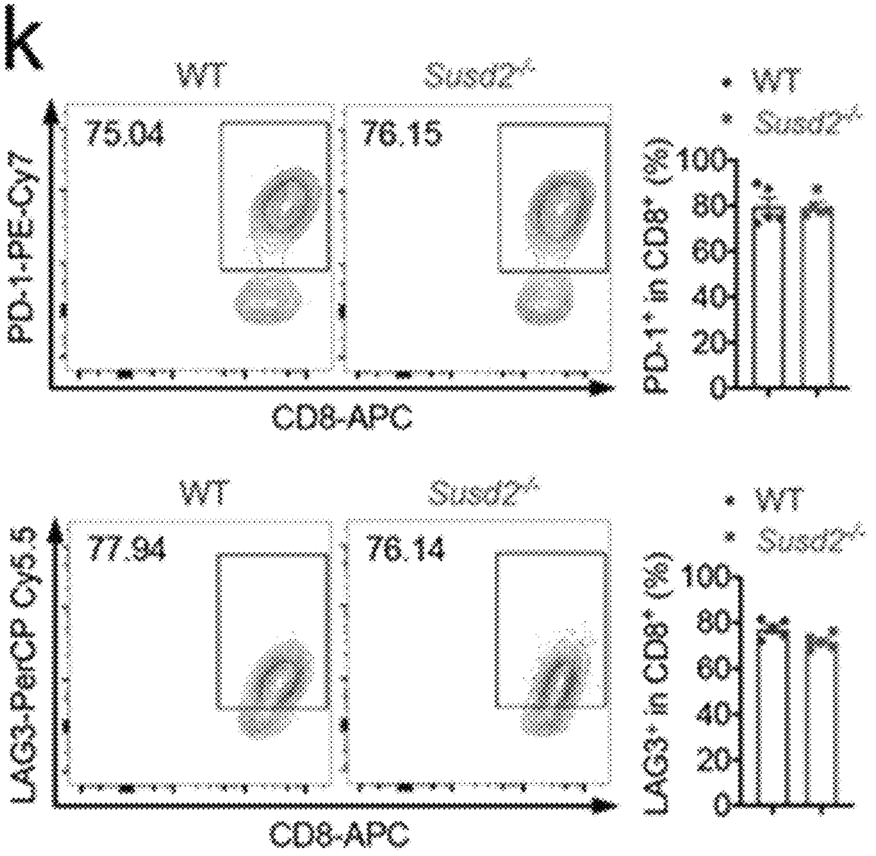
Figure 9L:
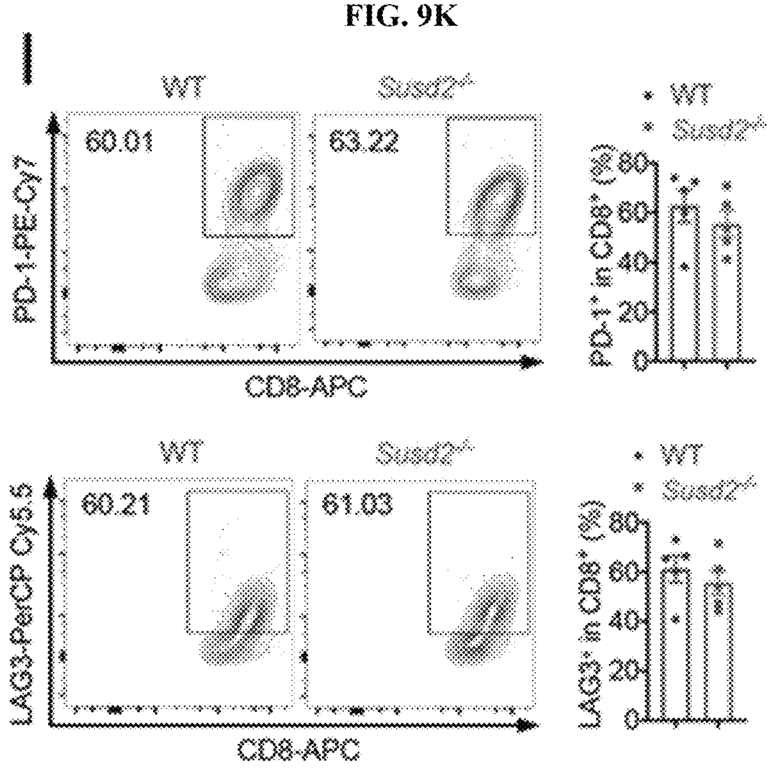

Next, Susd2$^{-/-}$ CD8$^+$ T cells were examined to exhibit altered expression of immune checkpoint molecules. Expression of PD-1 and LAG-3 was similar in intratumoral wild-type and Susd2$^{-/-}$ CD8$^+$ T cells in mice challenged with MC38, EG7 or B16-OVA cells (FIG. 9J-9L). MC38 tumor growth was significantly delayed in Susd2$^{-/-}$ mice treated with PD-L1 Ab compared to similarly treated wild-type mice (FIG. 2J), which translated into extended survival (FIG. 2J). Despite tumor growth showing minimal response to PD-L1 Ab treatment in wild-type mice, tumor growth was significantly attenuated, and survival was improved in PD-L1 Ab-treated Susd2$^{-/-}$ mice challenged with either EG7 (FIG. 2K) or B16-F10 (FIG. 2L) cells. Moreover, MC38 tumors exhibited a significantly delayed growth, alongside increased survival in Susd2$^{-/-}$ mice compared to wild-type mice treated with PD-1 Ab (FIG. 2M). In sum, deletion of Susd2 synergized with PD-1 and PD-L1 blockade treatments to improve antitumor immunity.

Susd2$^{-/-}$ CD8$^+$ T Cells Show Enhanced Antitumor Function

Figure 3A:
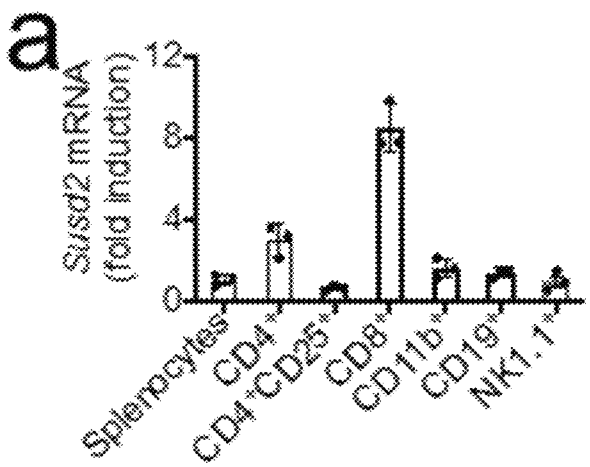
FIGS. 3A-3T show Susd2$^{-/-}$ CD8$^+$ cells exhibit increased antitumor effector function and survival.
Figure 3B:
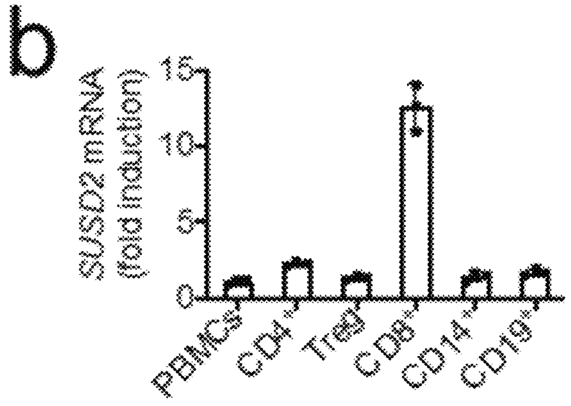
Figure 3C:
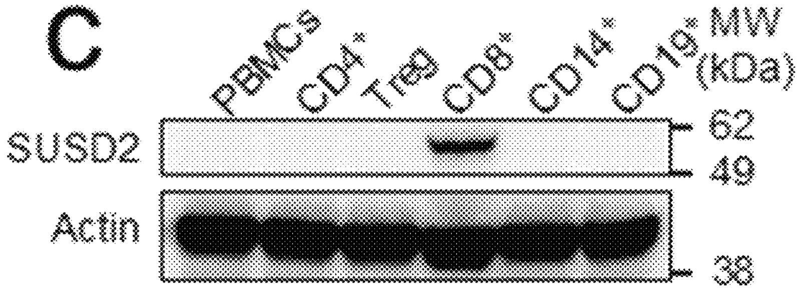
Figure 3D:
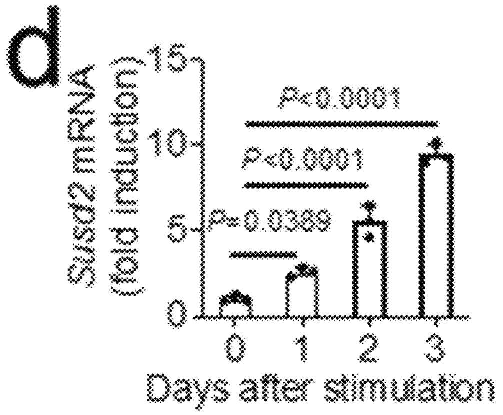
FIGS. 3D-3G shows the transcript and protein of SUSD2 in sorted mouse CD8$^+$ T cells, mouse CD4$^+$ T cells and human CD8$^+$ T cells that have been left untreated or stimulated with CD3-CD28 Abs.
Figure 3E:
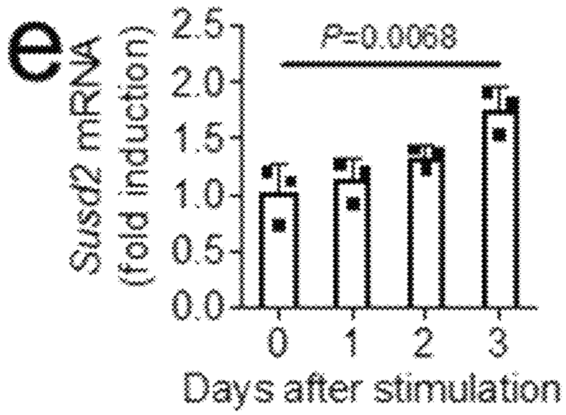
Figure 3F:
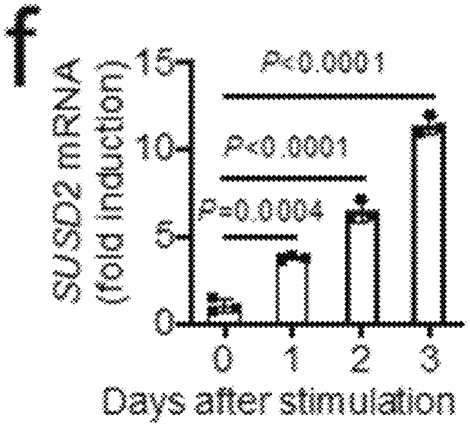
Figure 3G:
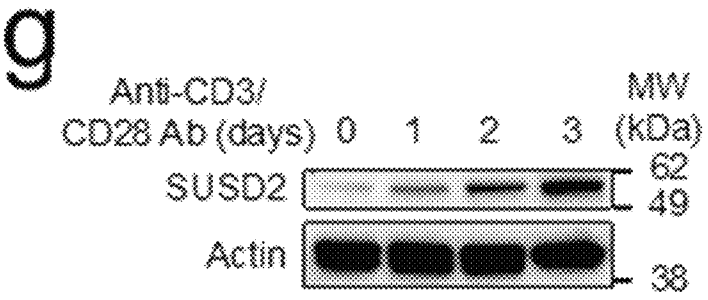
Figure 3H:
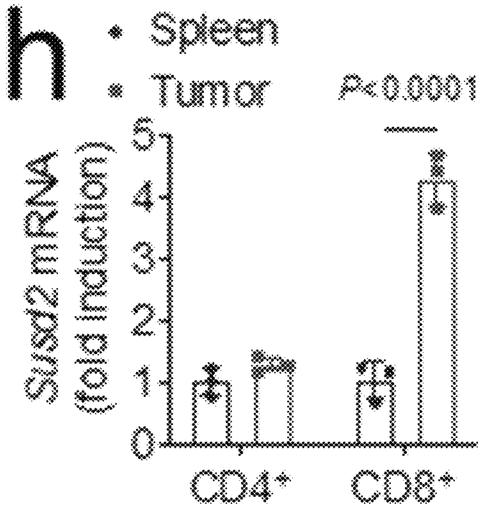
FIG. 3H shows the expression of Susd2 transcript in CD4$^+$ and CD8$^+$ T cells isolated from either spleen or tumor tissue in mice bearing MC38 tumor.
Figure 3I:
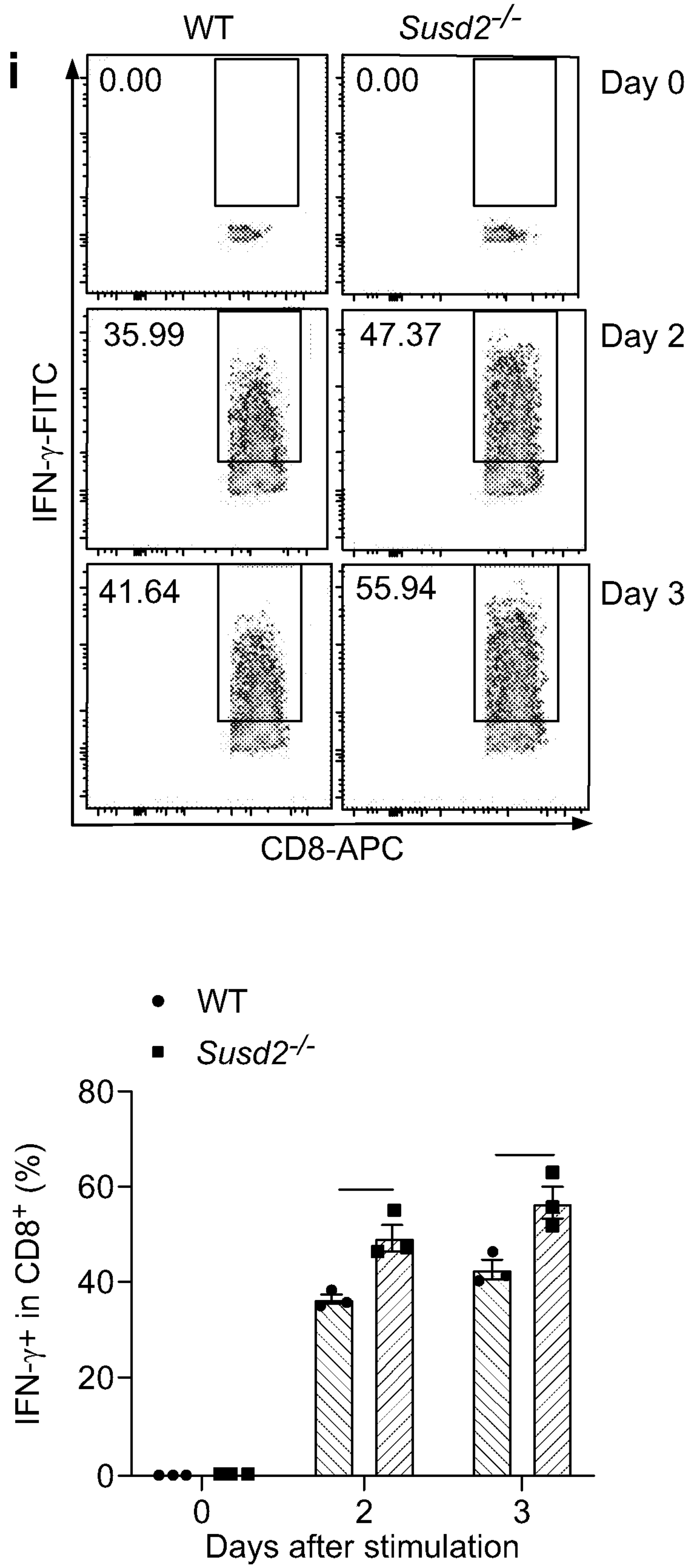
FIGS. 3I-3K shows the representative flow cytometry analysis showing IFN-γ$^+$CD8$^+$ T cells, GzmB$^+$CD8$^+$ T cells and TNF$^+$CD8$^+$ T cells in OVA257-264 stimulated splenocytes isolated from WT or Susd2$^{-/-}$ OT-I mice at day 0, 2 and 3.
Figure 3J:
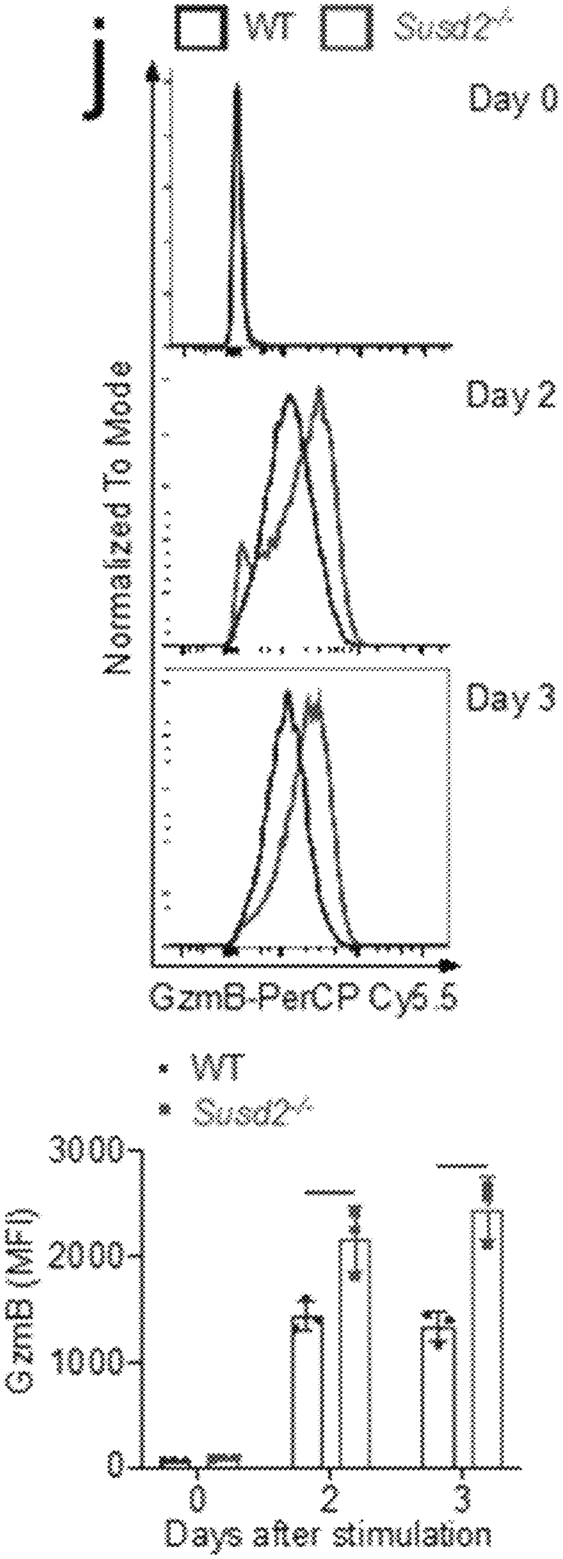
Figure 3K:
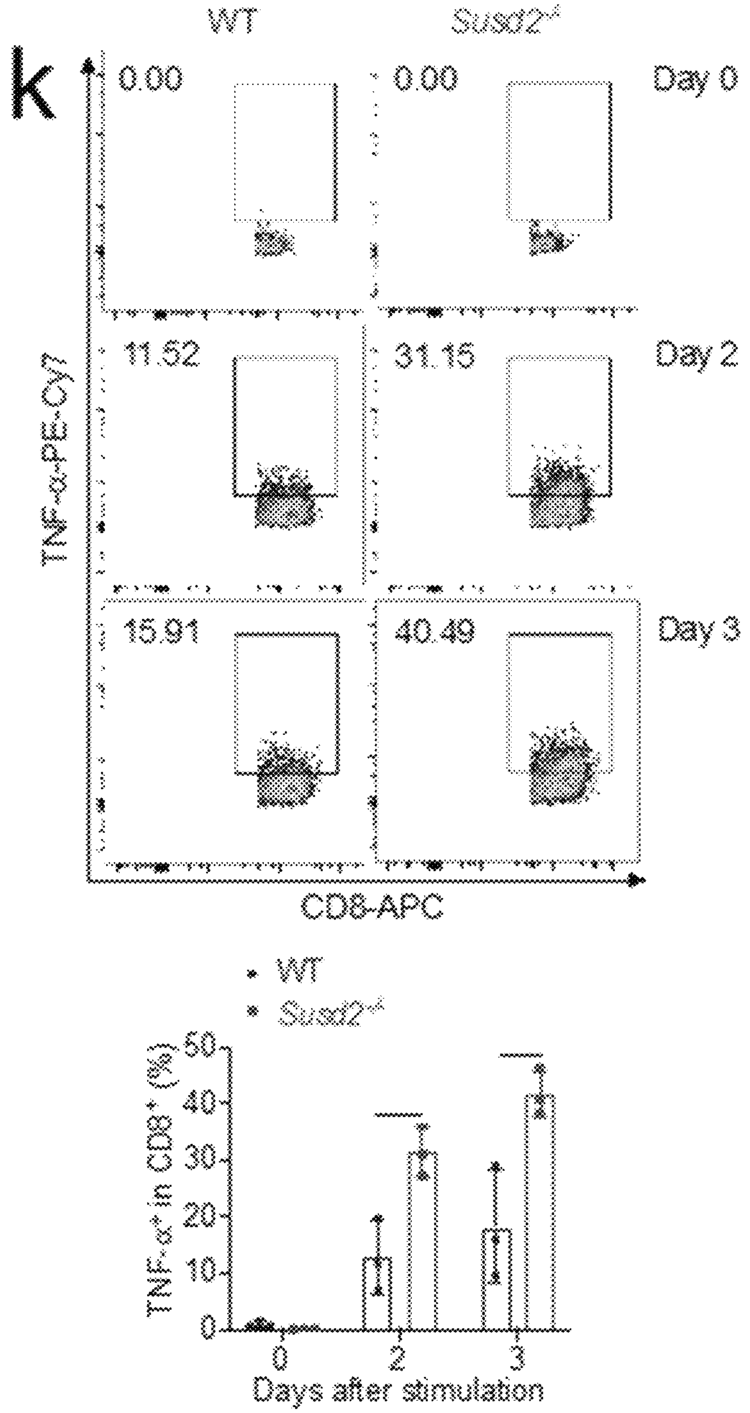

Next, SUSD2 was examined for direct modulation of CD8$^+$ T cell function. In various immune cell populations sorted from the spleen of naïve C57BL/6 mice, CD8$^+$ T cells had the highest amount of Susd2 transcript (FIG. 3A). Highest amounts of SUSD2 mRNA and protein were also detected in human CD8$^+$ T cells isolated from peripheral blood mononuclear cells (PBMCs) (FIG. 3B-3C). Stimulation with CD3-CD28 Abs induced a marked increase in the amount of Susd2 transcript in sorted mouse CD8$^+$ T cells, whereas mouse CD4$^+$ T cells exhibited a moderate increase at day 3 post-stimulation (FIG. 3D-3E). SUSD2 mRNA and protein were also augmented in human CD8$^+$ T cells by stimulation with CD3-CD28 Abs (FIG. 3F-3G). Increased Susd2 mRNA expression was detected in CD8$^+$ T cells, but not CD4$^+$ T cells, infiltrating the MC38 tumors compared to splenic CD8$^+$ T cells (FIG. 3H). Therefore, SUSD2 was highly expressed in mouse and human CD8$^+$ T cells and its expression was further upregulated by TCR activation.

Figure 3L:
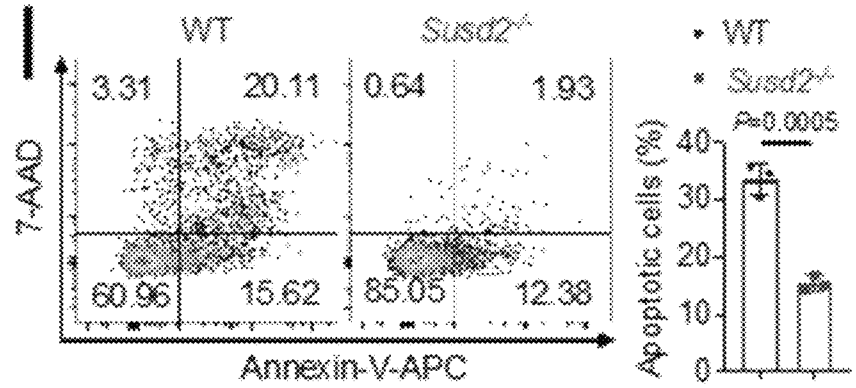
FIG. 3L shows the flow cytometry analysis showing annexin V$^+$7-AAD$^+$CD8$^+$ T cells in OVA257-264 stimulated splenocytes isolated from WT or Susd2$^{-/-}$ OT-I mice at day 3.
Figure 10A:
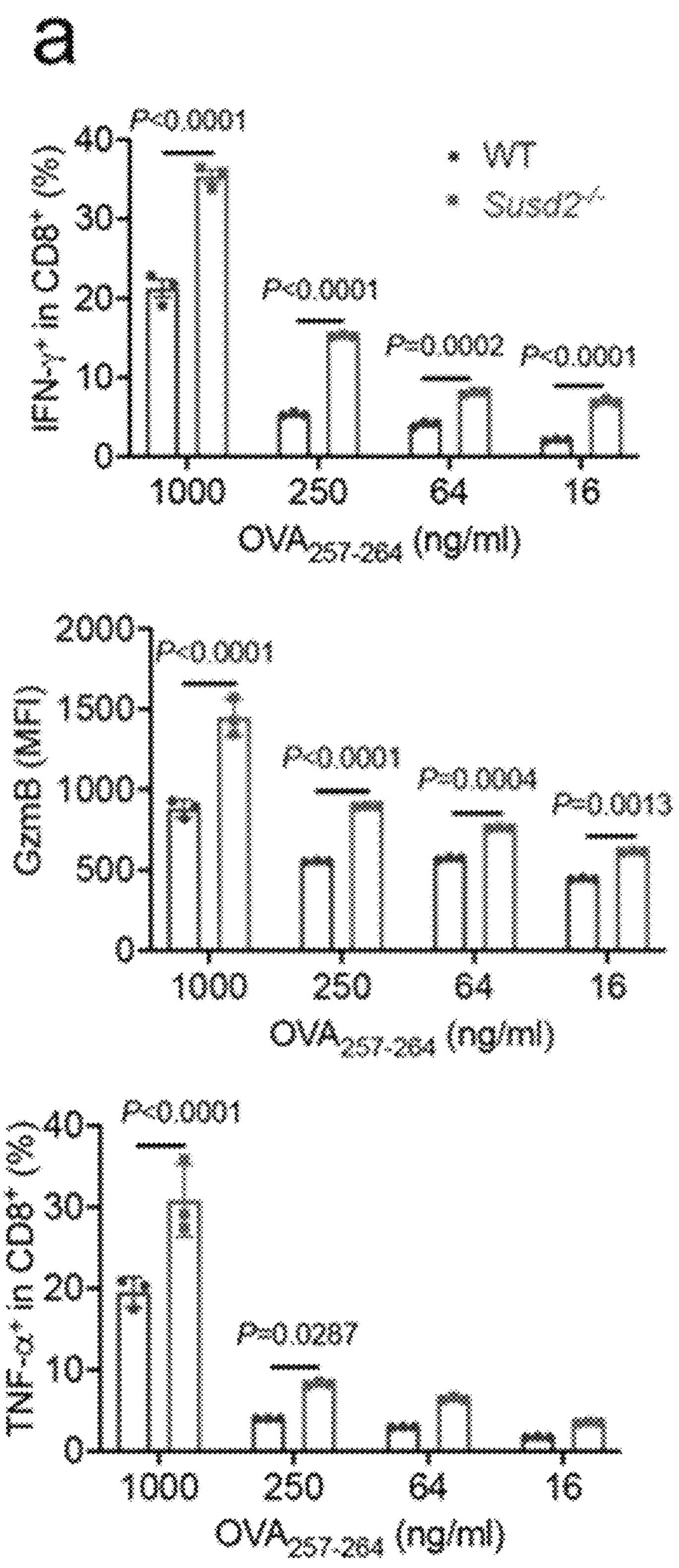
FIGS. 10A-10F shows that $Susd2^{-/-}$ $CD8^+$ cells exhibit increased antitumor effector function.
Figure 10B:
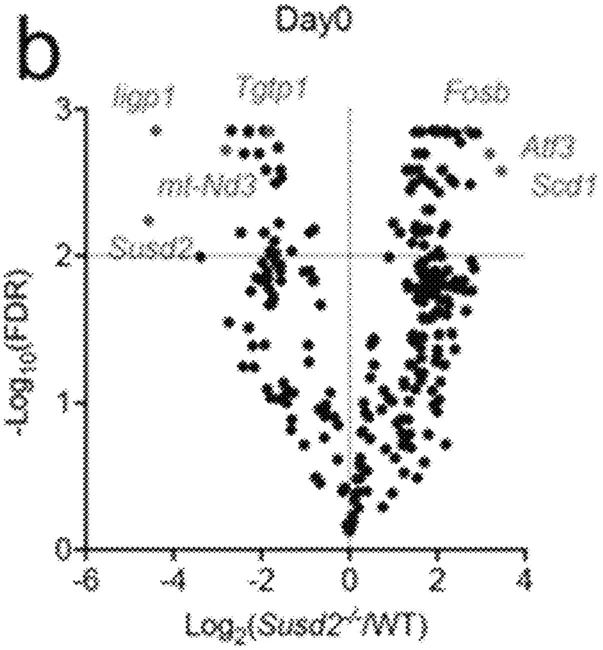
Figure 10C:
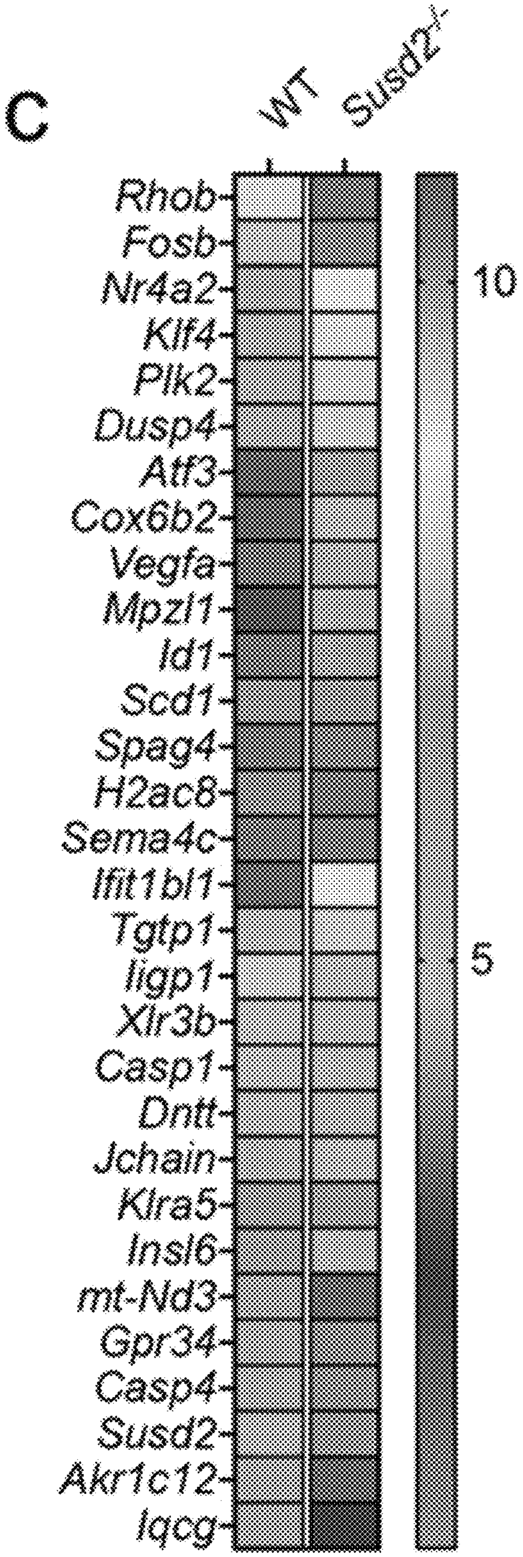
Figure 10D:
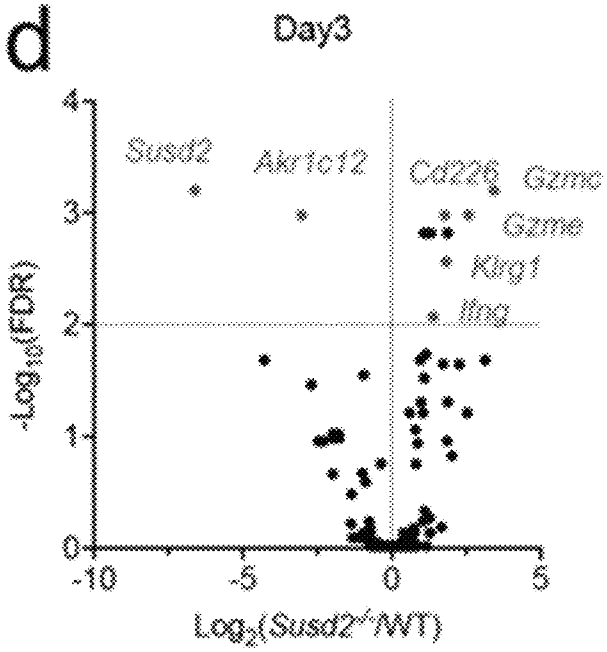
Figure 10E:
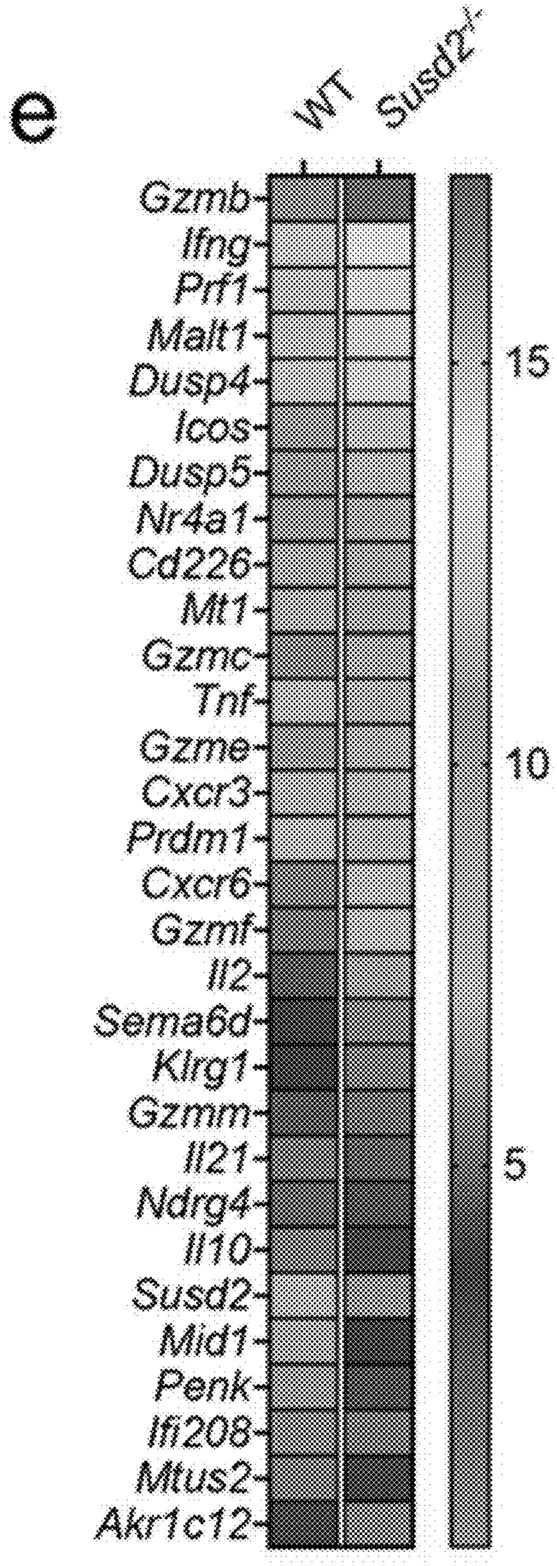
Figure 10F:
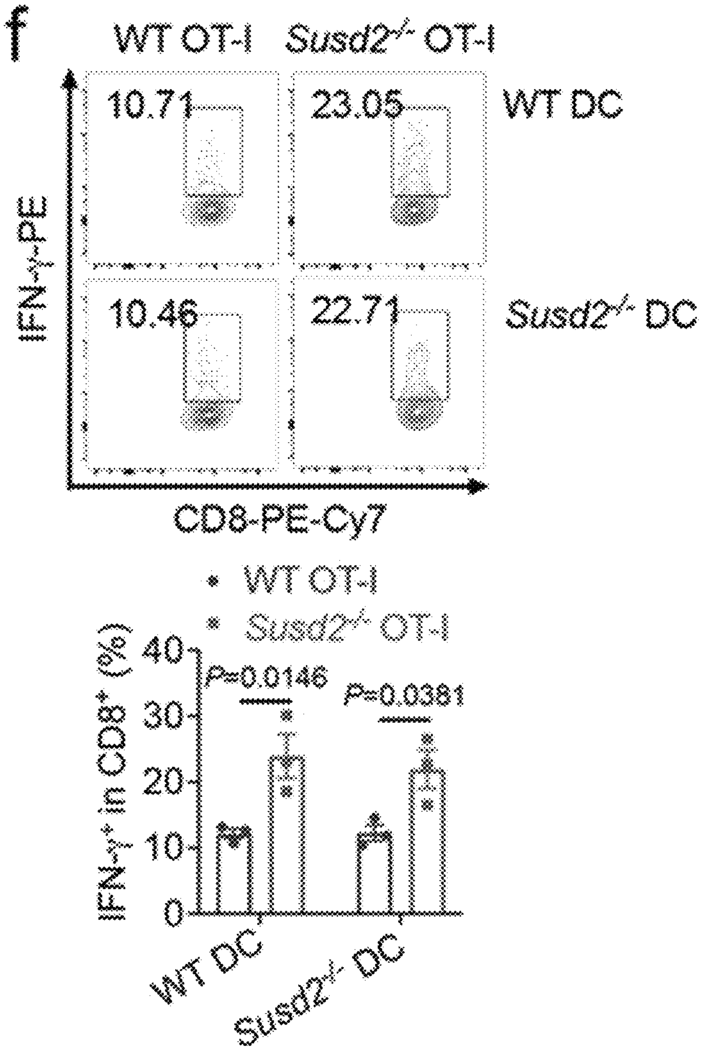
Figure 11A:
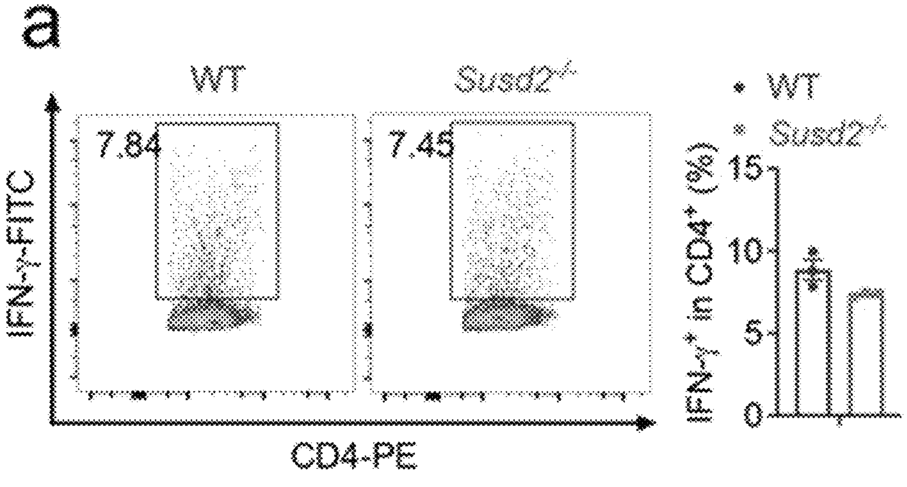
FIGS. 11A-11C show that Susd2 deficiency does not affect effector function of $CD4^+$ T cells or inhibitory function of Treg cells.
Figure 11A:
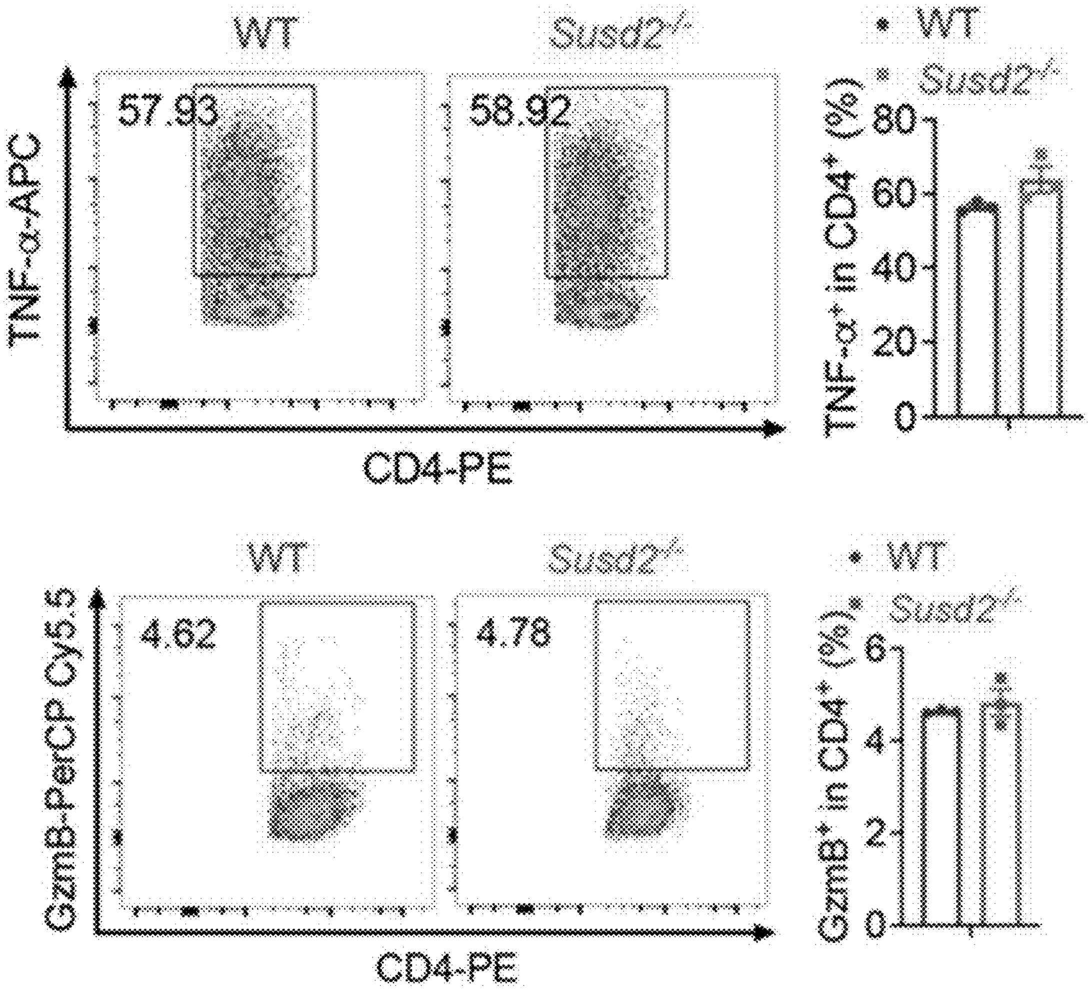
Figure 11B:
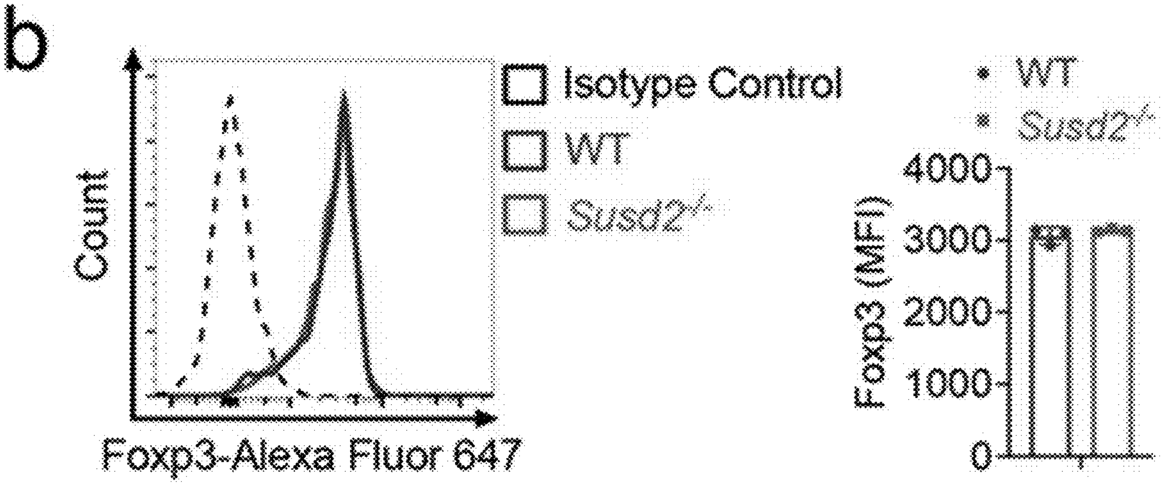
Figure 11C:
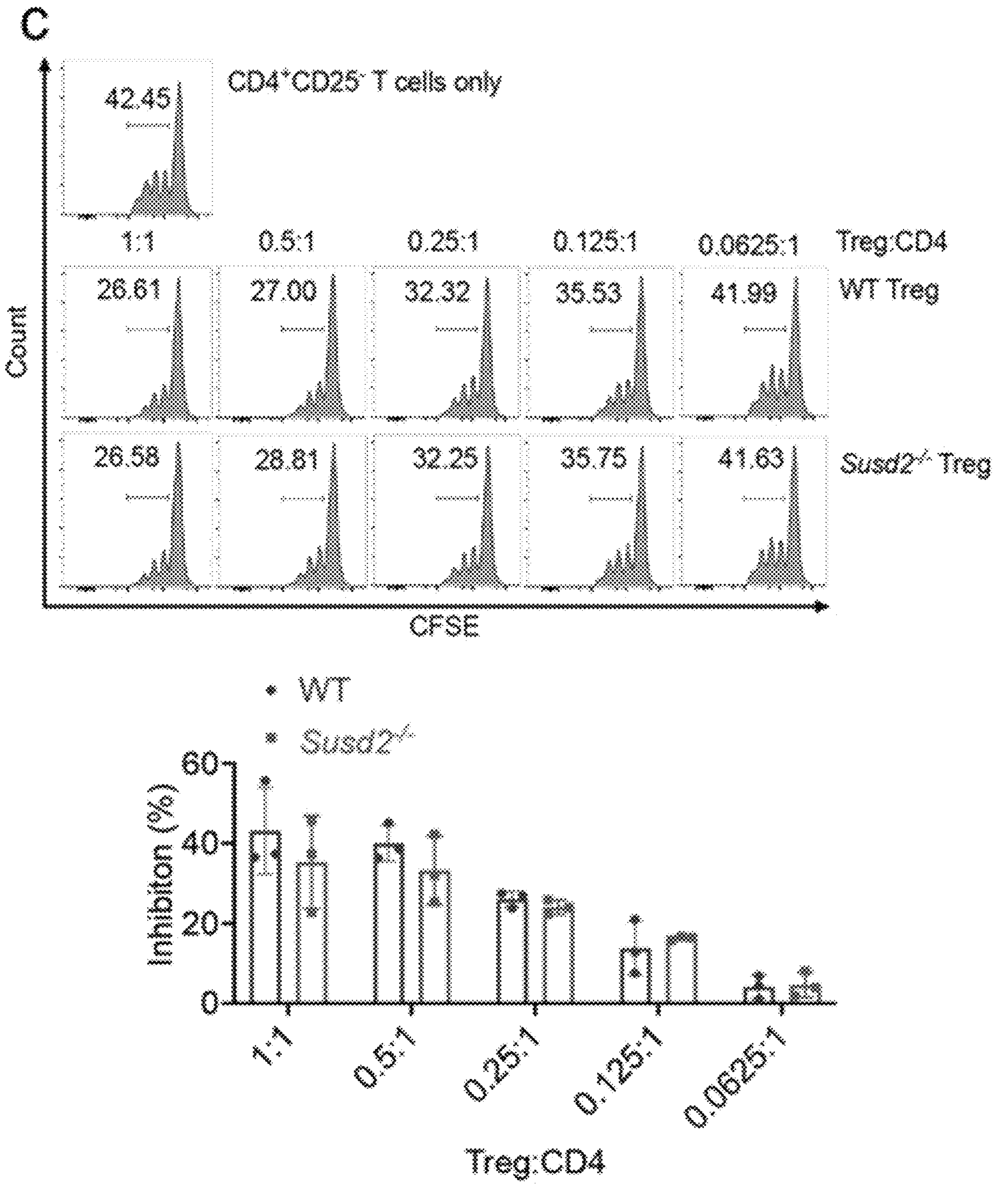

Next, total splenocytes from Susd2$^{-/-}$ OT-I mice were challenged with the cognate antigen peptide OVA257-264. Susd2$^{-/-}$ CD8$^+$ OT-I T cells generated significantly higher amounts of IFN-γ, GzmB and TNF (FIG. 3I-3K and FIG. 10A), as well as significantly attenuated cell apoptosis, as assayed by staining with 7-AAD and annexin V, after antigen stimulation for 3 days (FIG. 3L), compared to wild-type CD8$^+$ OT-I T cells. RNA-seq in splenic CD8$^+$ T cells isolated from wild-type or Susd2$^{-/-}$ OT-I mice stimulated or not with OVA257-264 for 3 days (FIG. 10B-10E) detected elevated expression of genes encoding T cell effector molecules, including Ifng, Prf1, Tnfa, Gzmc, in OVA257-264-activated Susd2$^{-/-}$ compared to wild-type CD8$^+$ OT-I T cells (FIGS. 10D and 10E). Susd2$^{-/-}$ CD8$^+$ OT-I T cells also exhibited enhanced cytotoxicity towards OVA peptide-pulsed MC38, EG7 or B16-OVA cells compared to wild-type CD8$^+$ OT-I T cells (FIG. 3M). In antigen-presenting assay, wild-type or Susd2$^{-/-}$ bone marrow-derived dendritic cells (BMDCs) pulsed with OVA257-264 were cultured with CD8$^+$ T cells isolated from wild-type or Susd2$^{-/-}$ OT-I mice. Susd2$^{-/-}$ CD8$^+$ T cells generated significantly higher amounts of IFN-γ, regardless of the BMDC genotypes, compared with wild-type CD8$^+$ T cells (FIG. 10F), showing the inhibitory effect of SUSD2 was intrinsic to the CD8$^+$ T cells. Production of IFN-γ, GzmB or TNF was similar in CD4$^+$ T cells isolated from wild-type or Susd2$^{-/-}$ OT-II mice when total splenocytes were challenged with the cognate antigen OVA323-339 (FIG. 11A), while Susd2$^{-/-}$ Treg cells expressed similar amounts of Foxp3 protein (FIG. 11B) and had a comparable capacity to block the proliferation of naïve CD4$^+$ T cells (FIG. 11C) compared to wild-type Treg cells, showing that loss of SUSD2 did not affect the function of CD4$^+$ T cells or Treg cells.

Figure 3N:
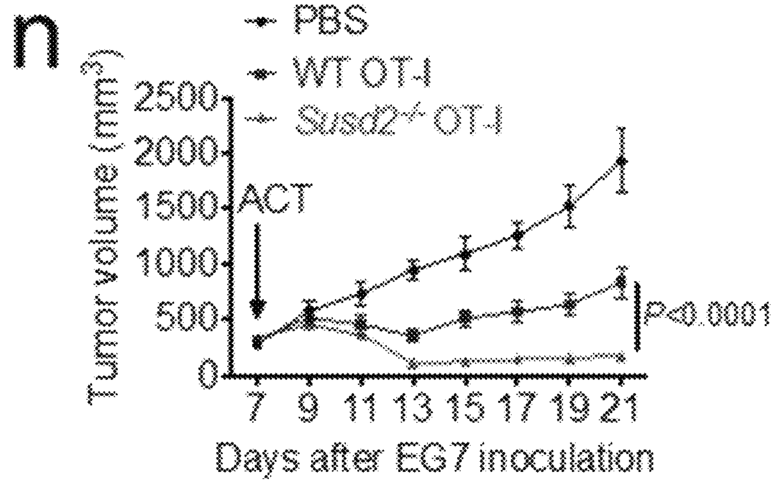
FIG. 3N shows the tumor growth in EG7 bearing mice post transferred with PBS, OVA257-264 primed WT or Susd2$^{-/-}$ OT-I T cells.
Figure 3O:
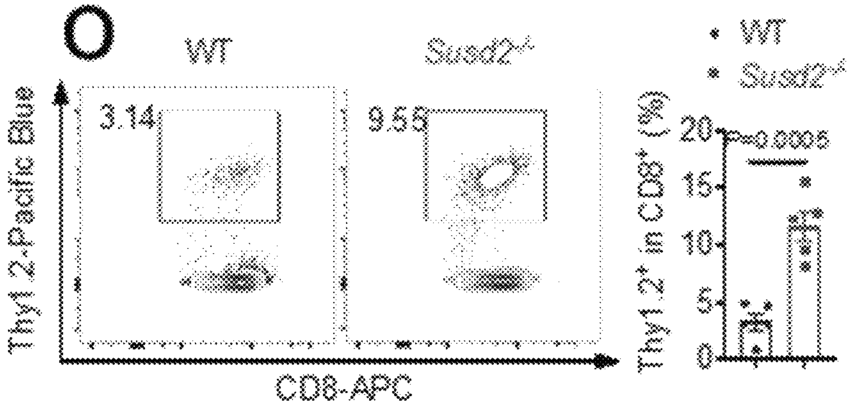
Figure 3P:
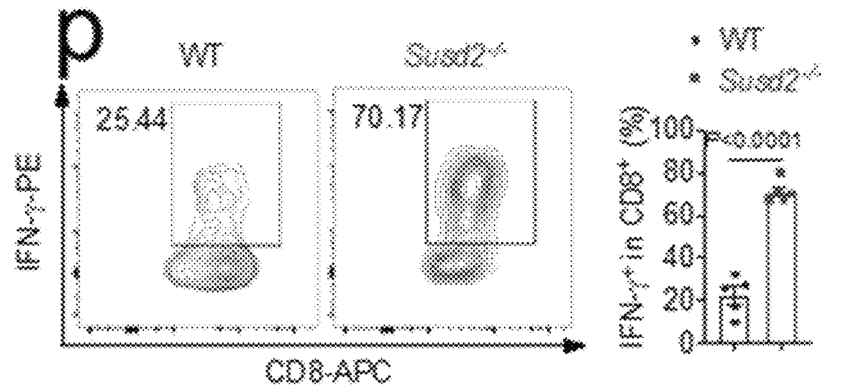
Figure 3Q:
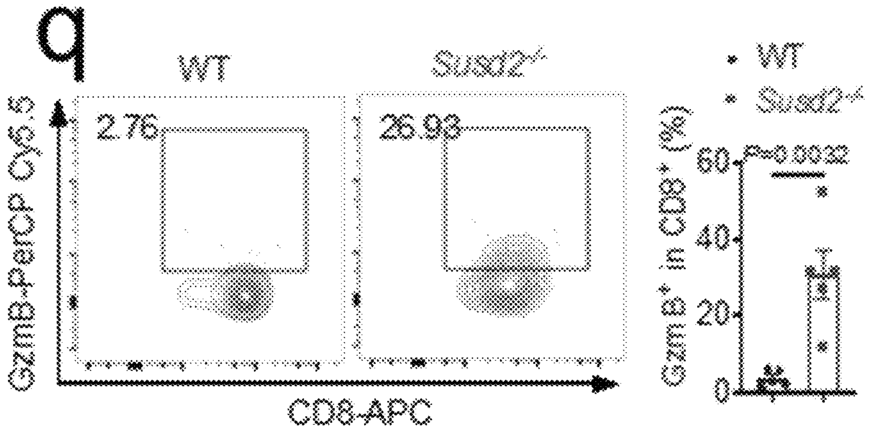
Figure 3R:
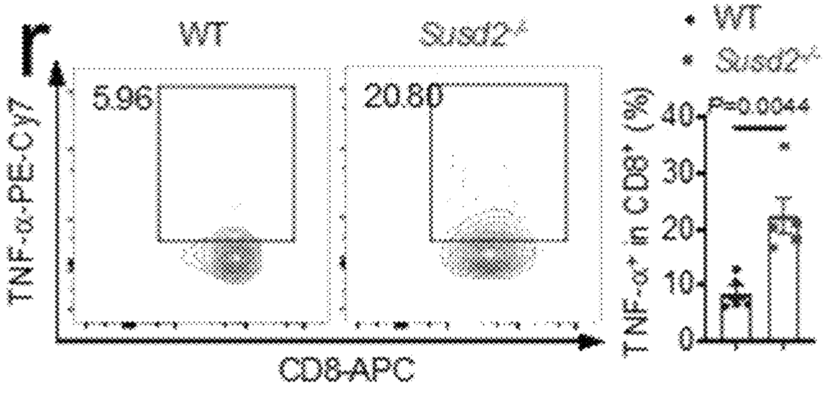
Figure 3S:
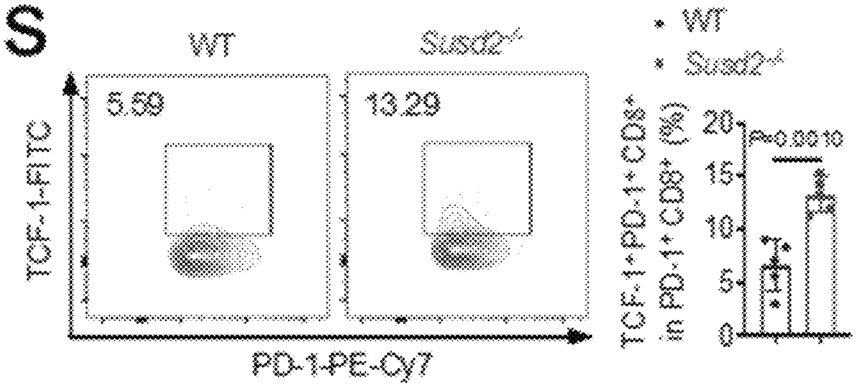
Figure 3T:
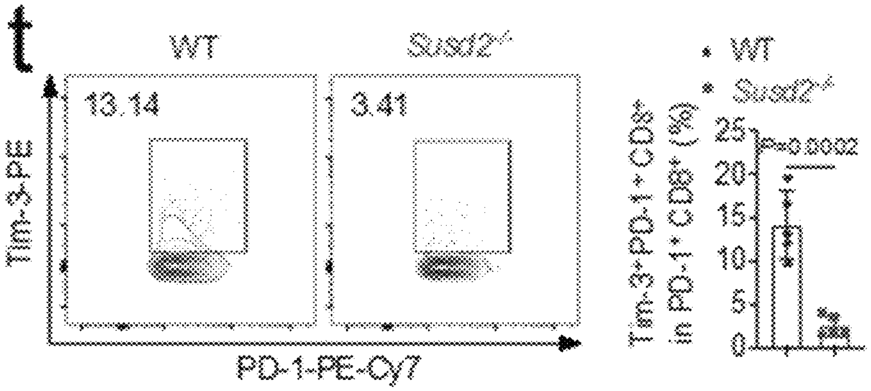

To evaluate the antitumor function of Susd2$^{-/-}$ CD8$^+$ T cells in vivo, Thy1.2$^+$ wild-type or Susd2$^{-/-}$ OT-I T cells were primed with OVA257-264 for 3 days and intravenously transferred them into Thy1.1$^+$ congenic wild-type mice challenged with EG7 tumor cells 7 days before cell transfer. While transfer of wild-type OT-I T cells resulted in reduced tumor growth compared to mice injected with PBS as control, transfer of Susd2$^{-/-}$ OT-I T cells led to complete eradication of EG7 tumor growth in all mice examined (FIG. 3N), showing a superior antitumor response by Susd2$^{-/-}$ compared to wild-type OT-I T cells. Transferred Susd2$^{-/-}$ OT-I T cells showed higher tumor infiltration and elevated production of IFN-γ, GzmB and TNF compared to wild-type OT-I T cells (FIG. 3O). Moreover, more intratumoral Susd2$^{-/-}$ OT-I T cells had a TCF1$^+$PD-1$^+$ TExP cell phenotype and a markedly decreased TCF1-PD-1$^+$ Tim-3$^+$ TExT cell phenotype compared to wild-type OT-I T cells (FIG. 3P-3Q), showing an attenuated transition of Susd2$^{-/-}$ T cells to terminal exhaustion. Collectively, these results showed that Susd2$^{-/-}$ CD8$^+$ T cells provided a superior antitumor effect, presumably through enhanced production of cytotoxic factors.

SUSD2-IL-2Rα Interaction Requires SD

Figure 4A:
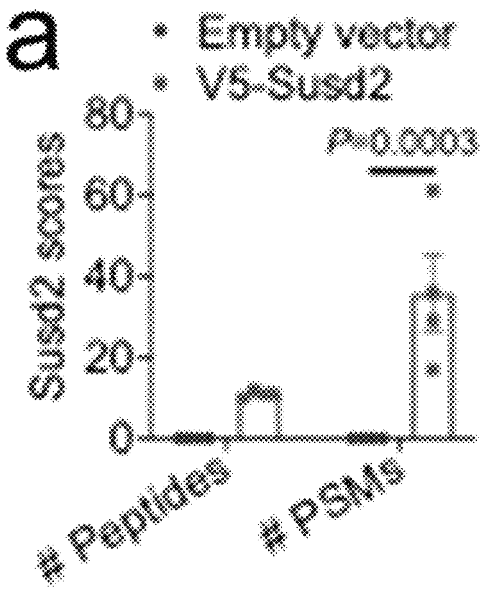
FIGS. 4A-4K show SUSD2 interacts with IL-2Rα via its sushi domain.
Figure 4B:
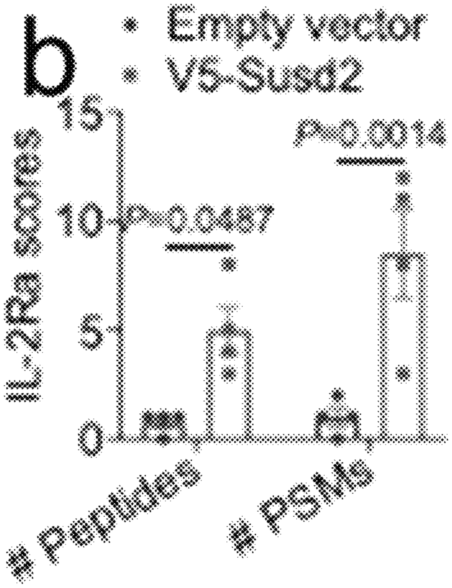
Figure 4C:
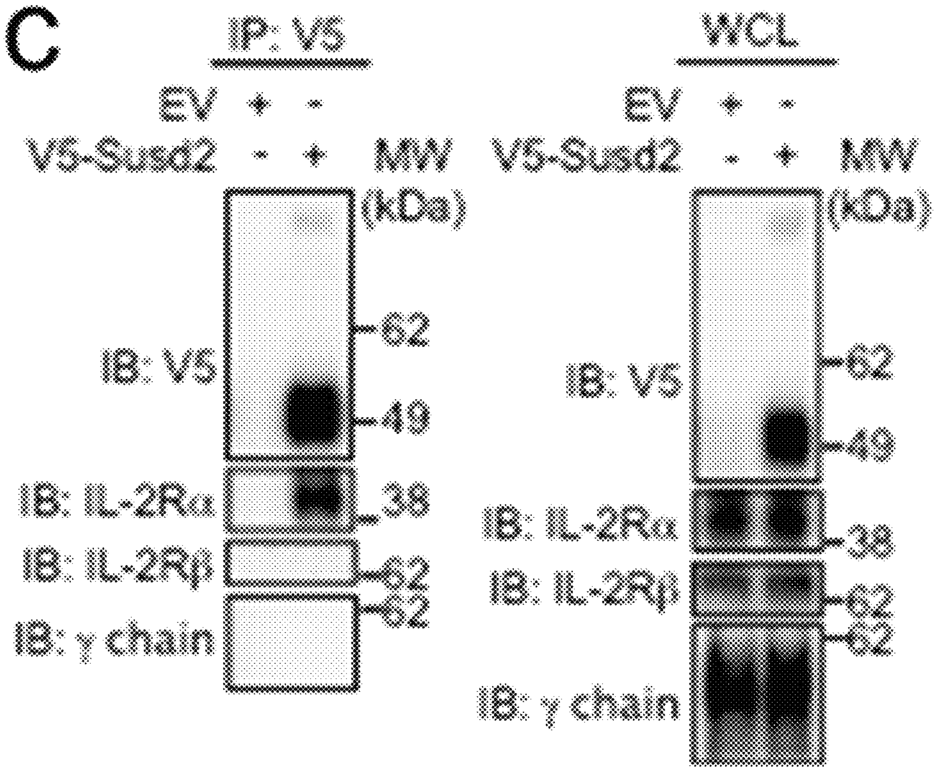
Figure 4D:
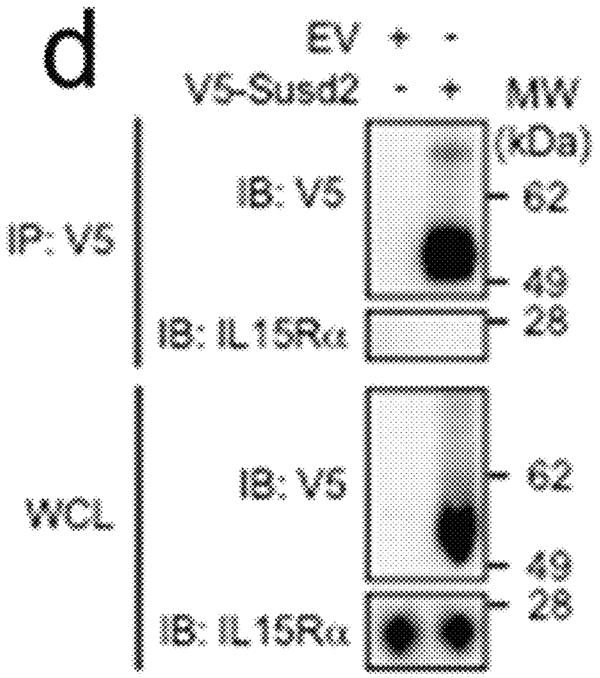
Figure 4E:
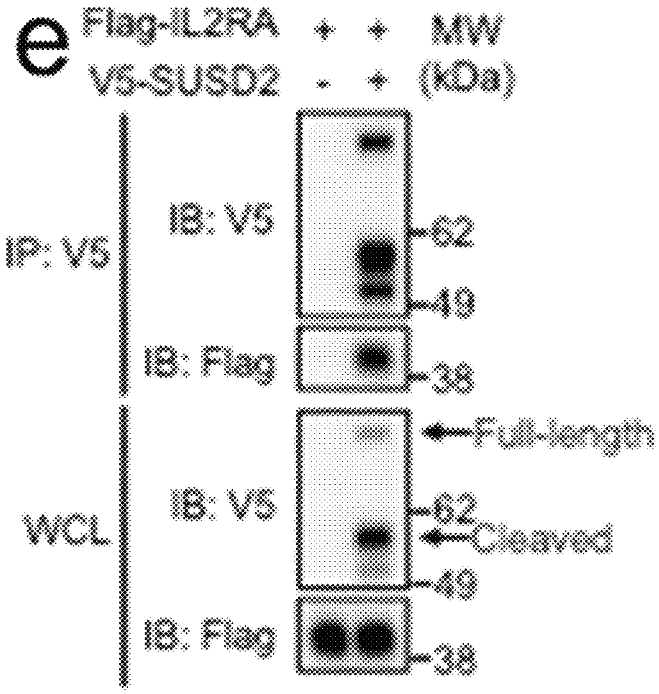
Figure 4F:
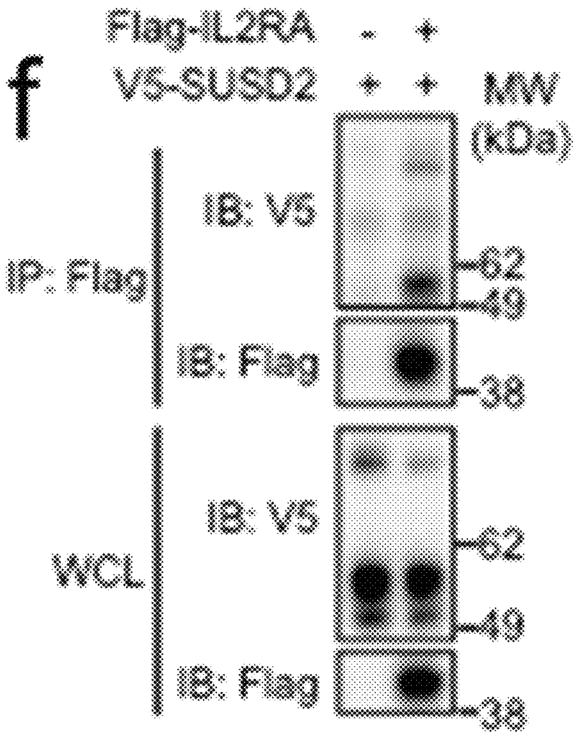
Figure 4G:
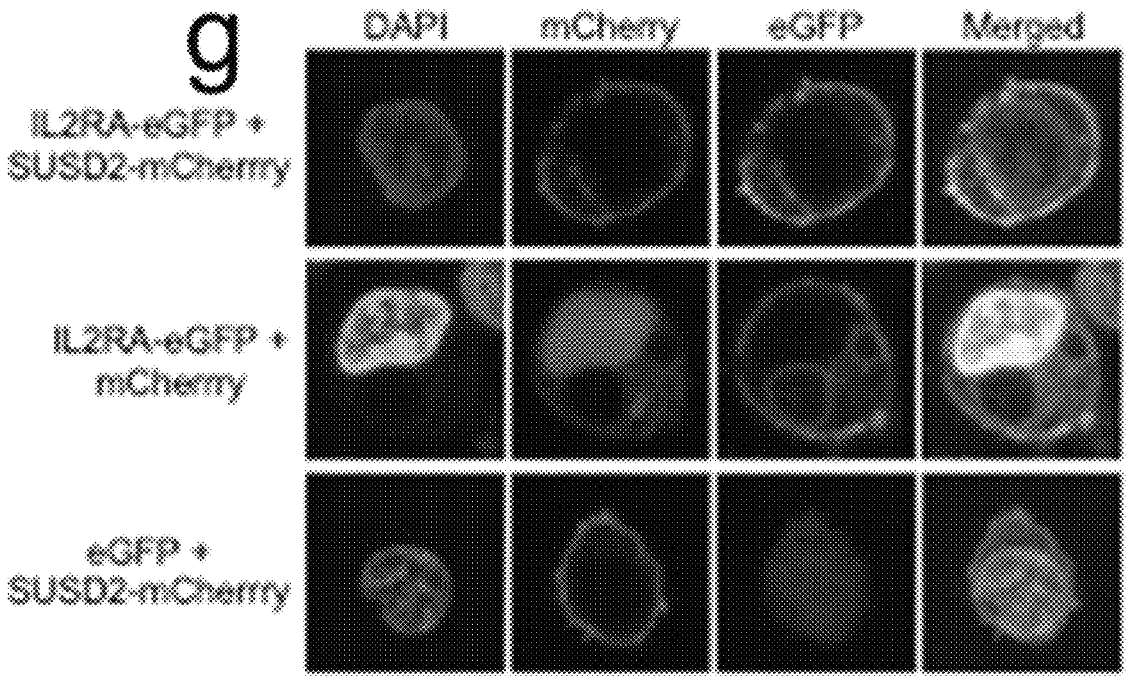
Figure 4H:
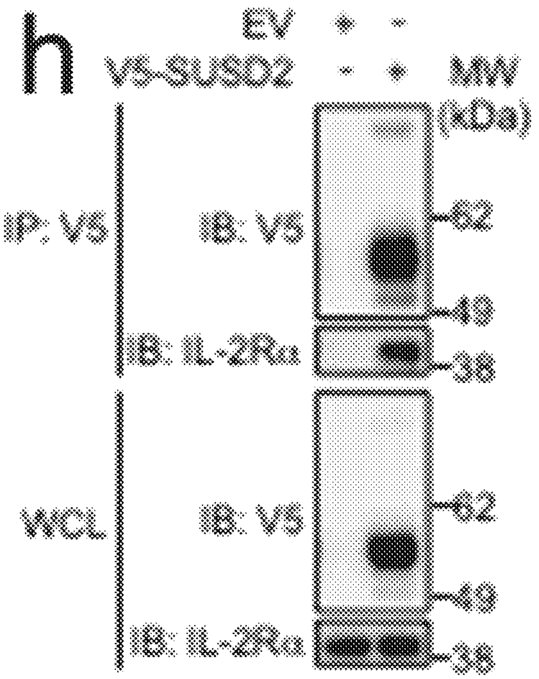
Figure 4I:
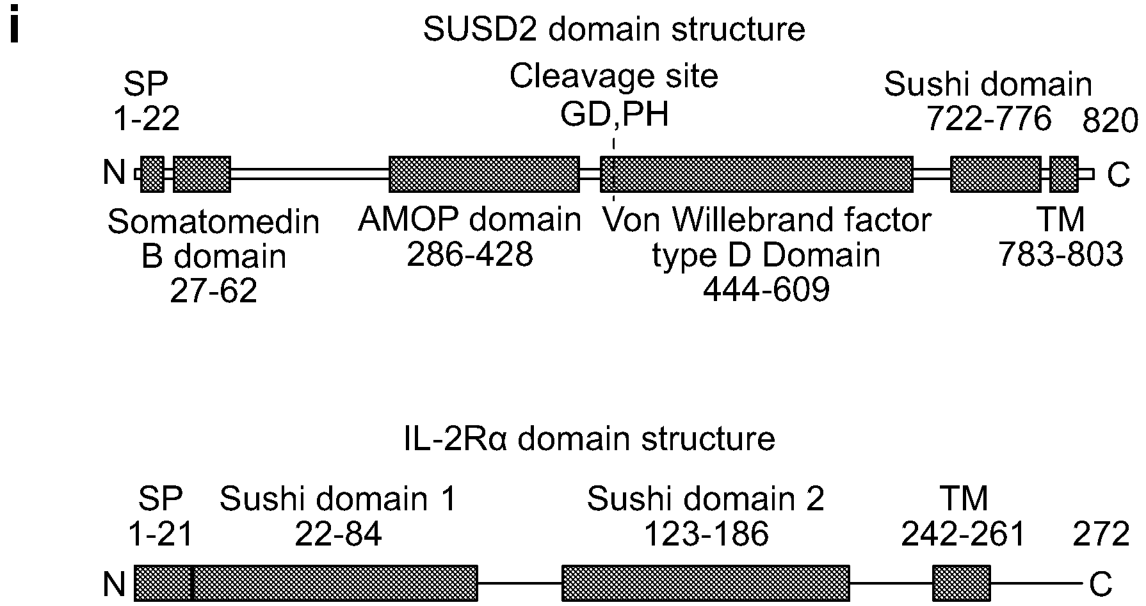
Figure 4J:
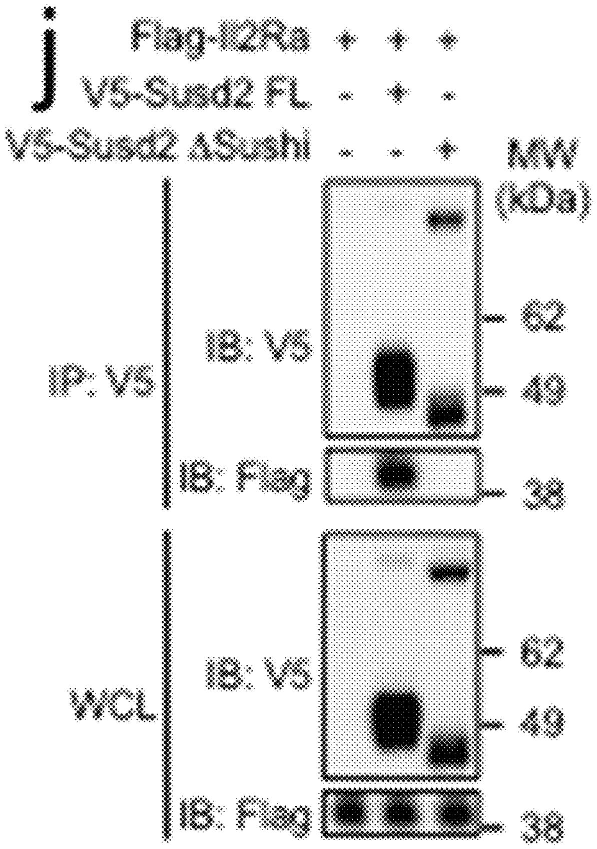
Figure 4K:
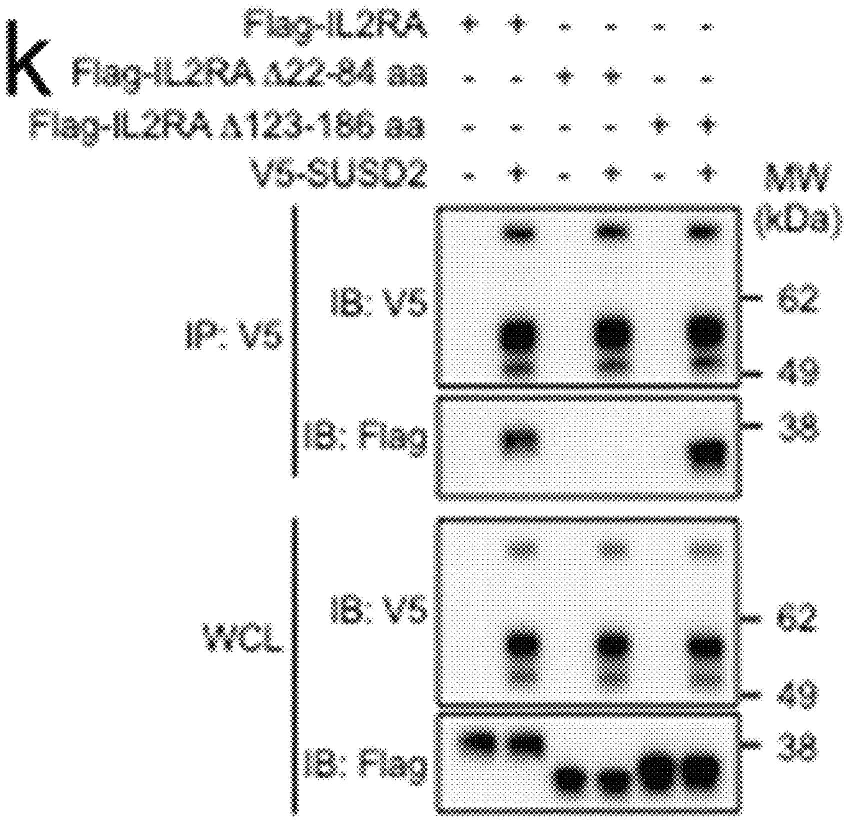
Figure 12B:
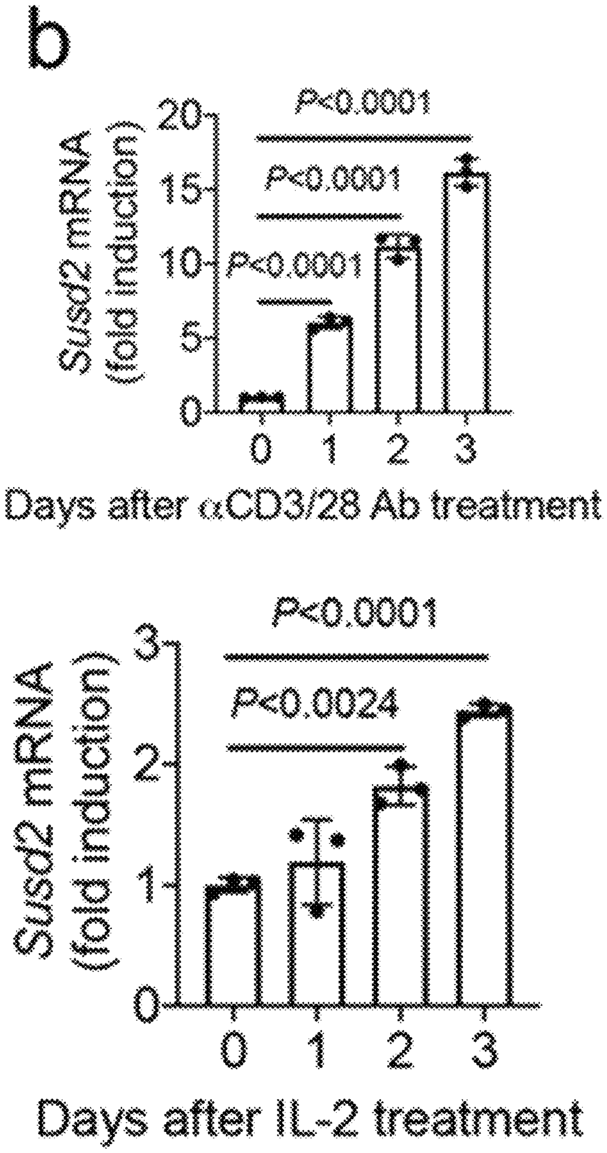
Figure 12B:
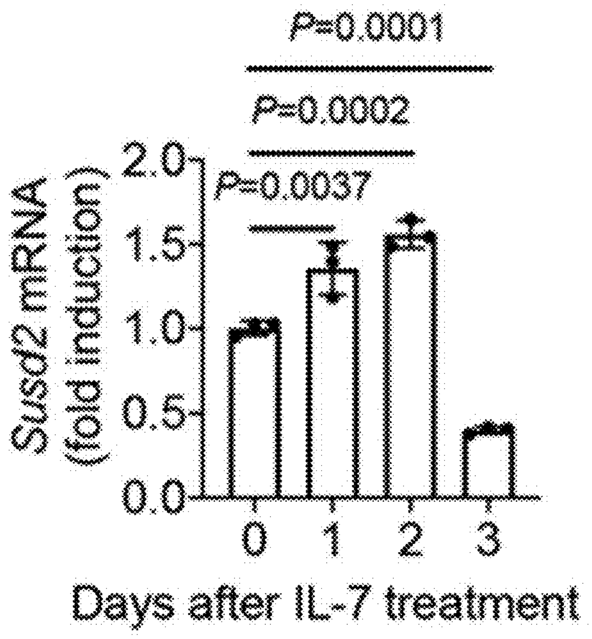
Figure 12B:
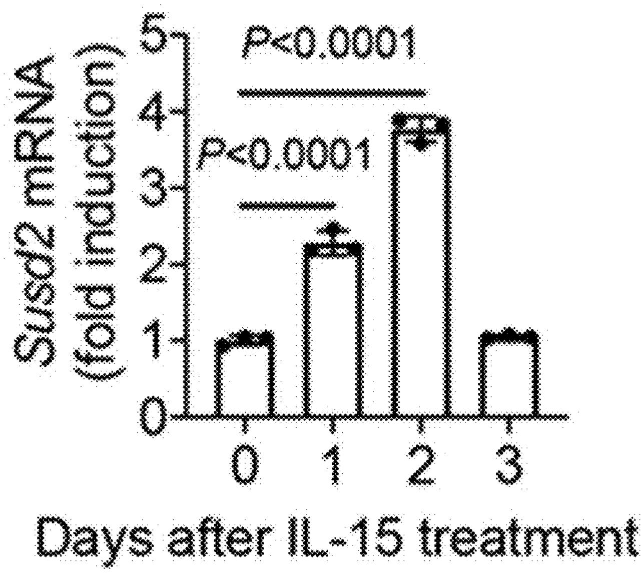

Because SUSD2 contains a short (16 amino acids) undefined cytoplasmic tail, showing that SUSD2 may not initiate intracellular signaling directly, SUSD2 was investigated for modulation of CD8$^+$ T cell effector function through its interaction with cell surface protein(s). To determine the interactome of SUSD2 in $CD8^+$ T cells, $Susd2^{-/-}$ OT-1 T cells were retrovirally transduced with a V5-tagged mouse Susd2 or empty vector as control, followed by V5 agarose immunoprecipitation and liquid chromatography coupled to tandem MS (LC-MS/MS). Susd2 was detected only in the precipitates from Susd2-reconstituted $Susd2^{-/-}$ OT-I T cells (FIG. 4A-4B). IL-2Rα was highly enriched in the precipitates from Susd2-reconstituted $Susd2^{-/-}$ OT-1 cells compared to those from $Susd2^{-/-}$ OT-I cells reconstituted with empty vector, based on the number of peptides (indicating the identification confidence) and the number of peptide-spectrum matches (PSMs, indicating the abundance) (FIG. 4A). Susd2 and IL-2Rα coimmunoprecipitated from Susd2-reconstituted cells activated by OVA257-264 for 3 days (FIG. 4C), while Susd2 did not pulldown IL-2Rβ, common 7 chain or IL-15Rα (FIG. 4C-4D), showing a specific interaction between Susd2 and IL-2Rα. The authenticity of the IL-2Rα band was verified by immunoblotting of 293T cells expressing Flag-tagged IL2RA (Flag-IL2RA) (FIG. 12A) using both human IL-2Rα (sc-365511) and Flag Abs (FIG. 12B). In 293T cells co-transfected with plasmids expressing V5-SUSD2 and Flag-IL2RA, SUSD2 co-immunoprecipitated with IL-2Rα (FIG. 4E-4F) and colocalized with IL-2Rα on the cell surface (FIG. 4G). Overexpressed V5-SUSD2 also pulled down endogenous IL-2Rα in human Jurkat T cells (FIG. 4H), showing that IL-2Rα interacted with SUSD2 in mouse and human cells. Because both SUSD2 and IL-2Rα contain a SD (FIG. 4B), which is known to mediate protein-protein interaction, the interaction between SUSD2 and IL-2Rα was mediated by the SD. In 293T cells co-expressing a SUSD2 mutant protein lacking the SD ($SUSD2^{\Delta SD}$) and IL-2Rα, an interaction between $SUSD2^{\Delta SD}$ and IL-2Rα could not be detected (FIG. 4I). Deletion of SD1 in IL-2Rα resulted in the loss of SUSD2-IL-2Rα interaction, while deletion of SD2 in IL2-Ra had no effect in 293T cells co-expressing the mutant IL-2Rα proteins and $SUSD2^{WT}$ (FIG. 4J). These observations showed that SUSD2 interacted with IL-2Rα, and the interactions was mediated by the SD in both proteins.

SUSD2 Negatively Regulates IL-2R Signaling

Figure 5A:
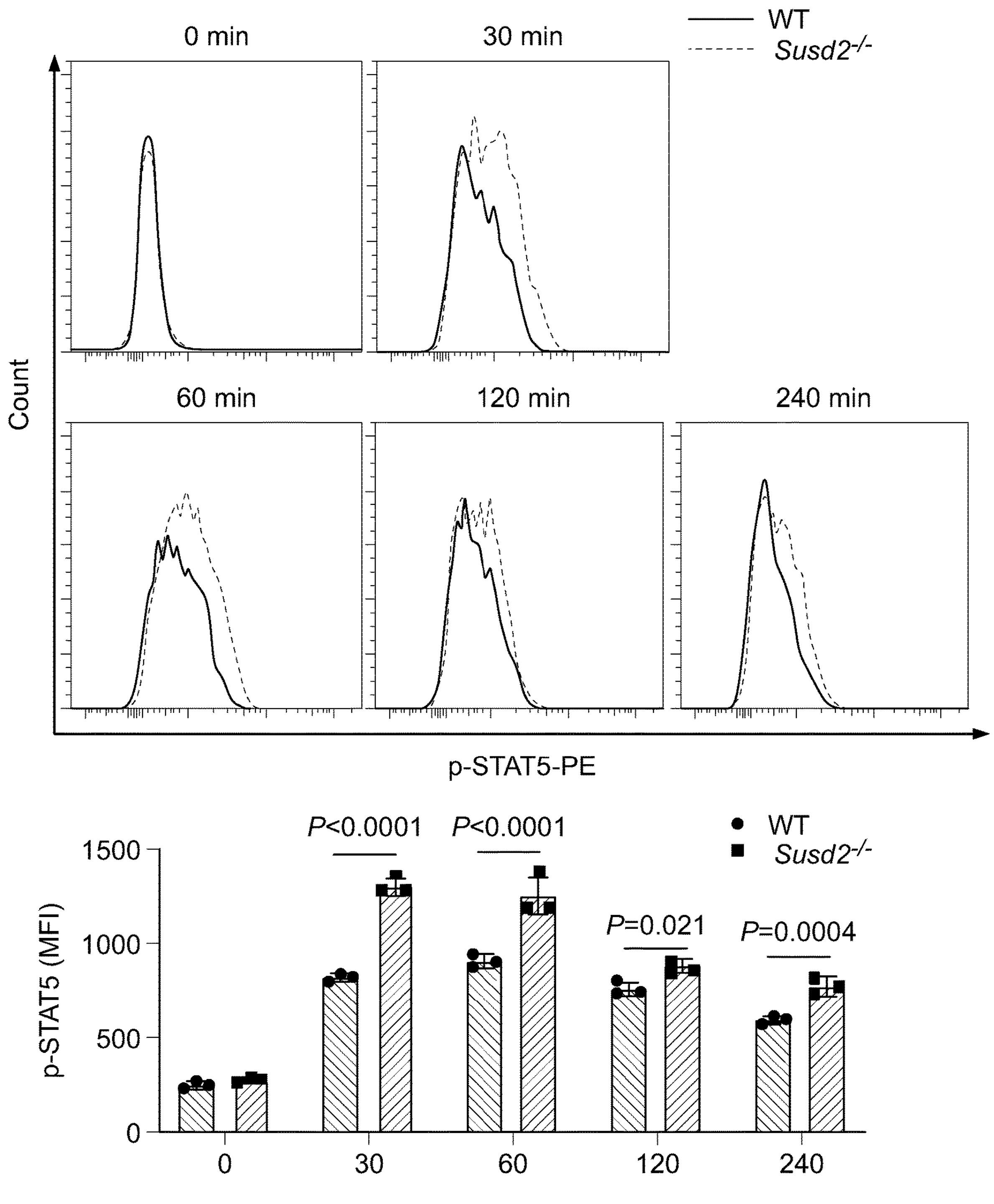
FIGS. 5A-5J show SUSD2 impairs CD8$^+$ cell effector function by attenuating IL-2Rα signaling.
Figure 5B:
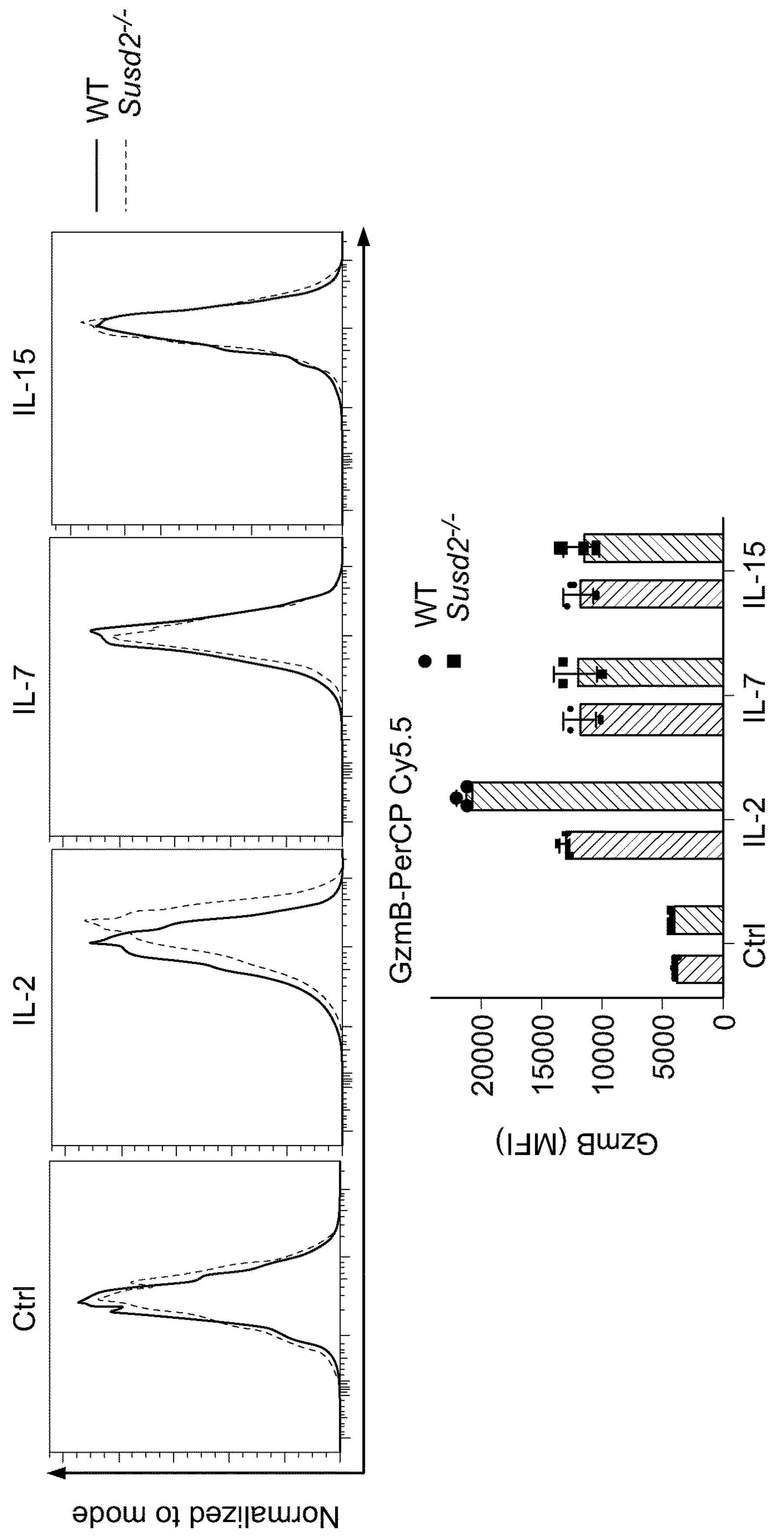
Figure 5C:
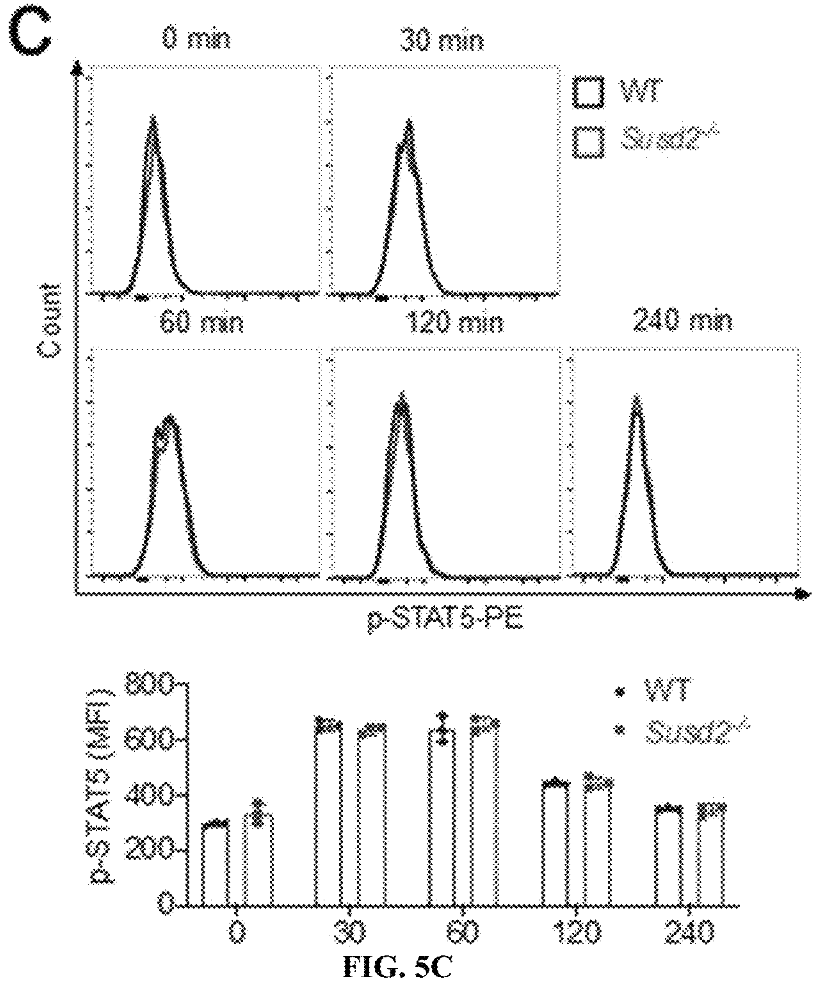
Figure 5D:
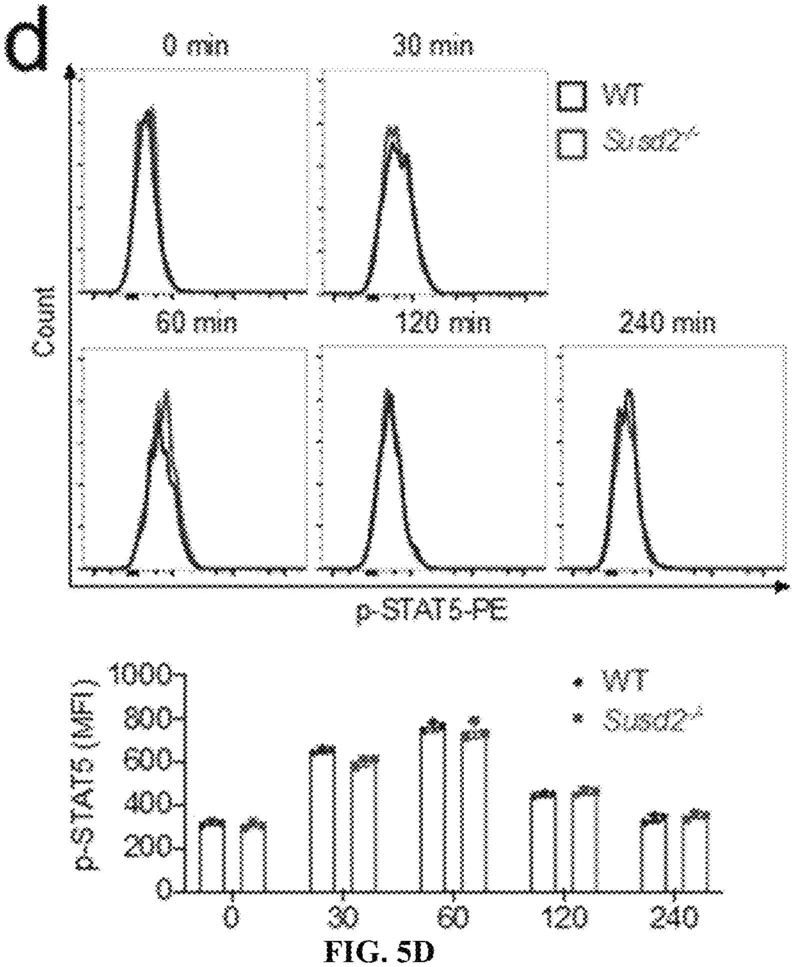
Figure 5E:
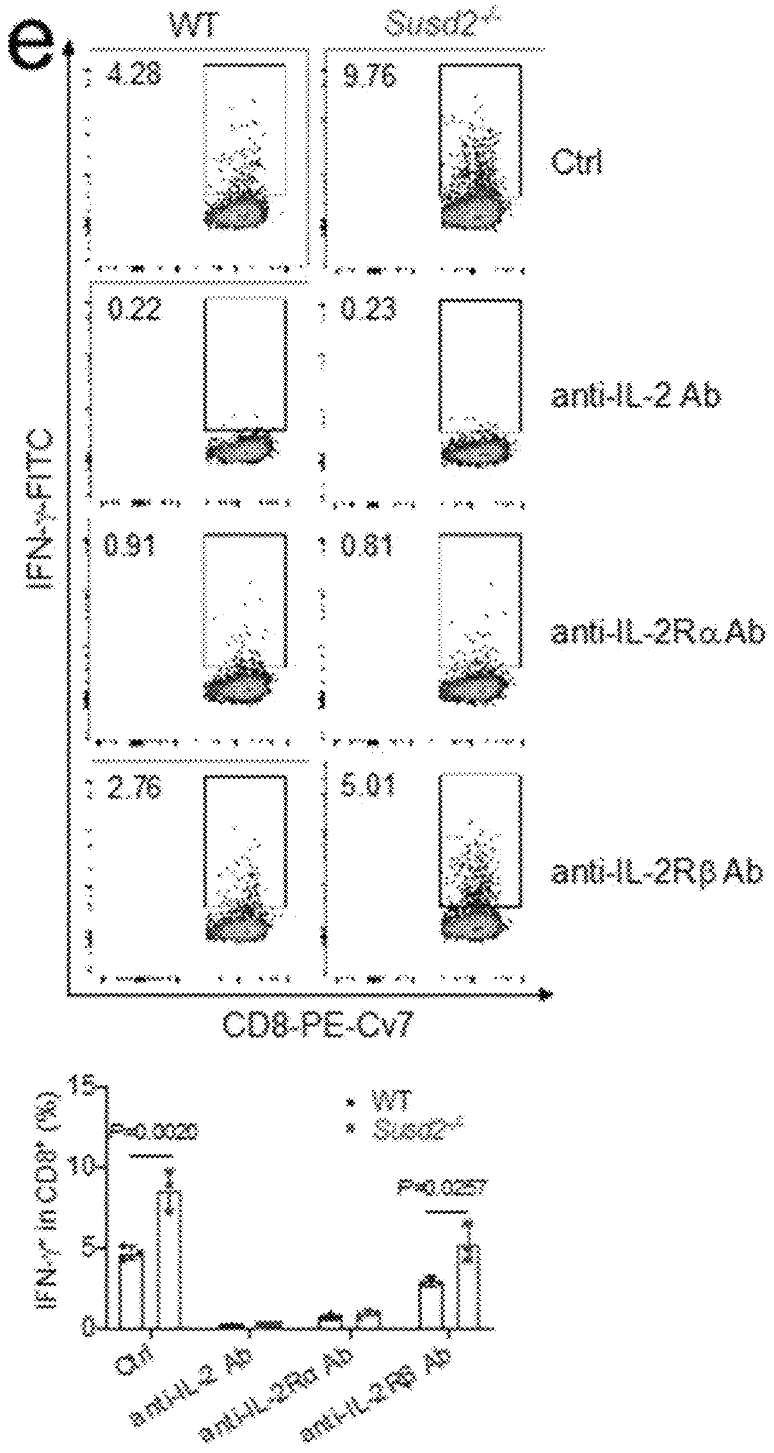
Figure 5F:
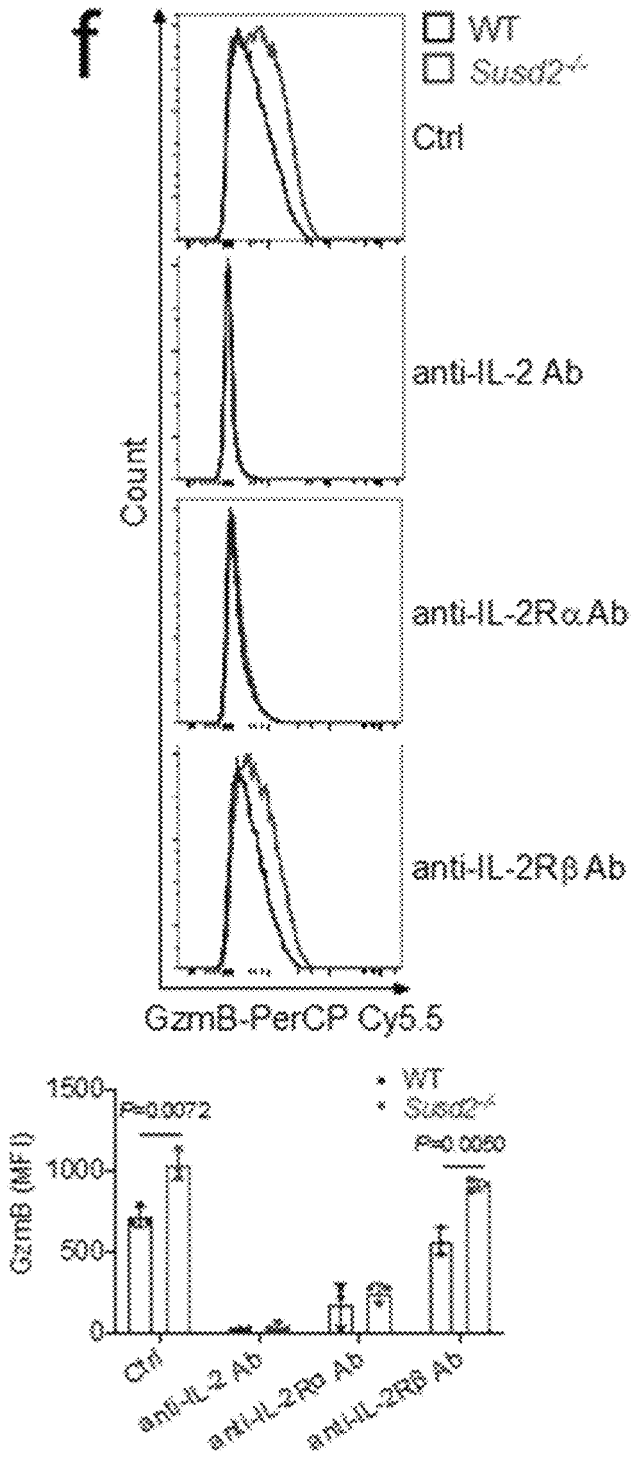
Figure 13A:
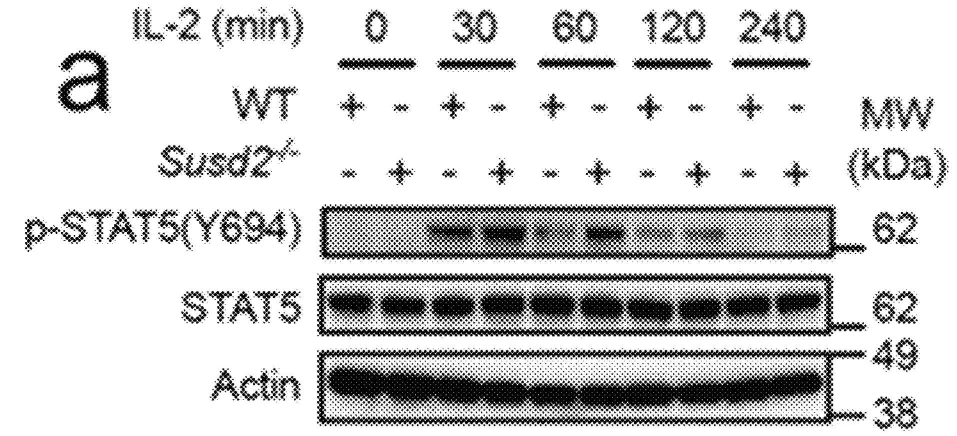
FIGS. 13A-13I show the efficient control of tumor growth by IL-2/$mAb_{CD25}$ complex in Susd2$^{-/-}$ mice.
Figure 13B:
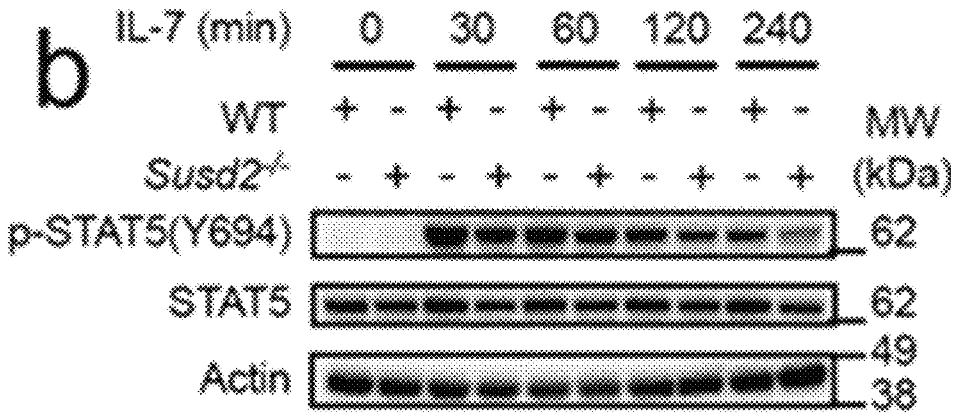
Figure 13C:
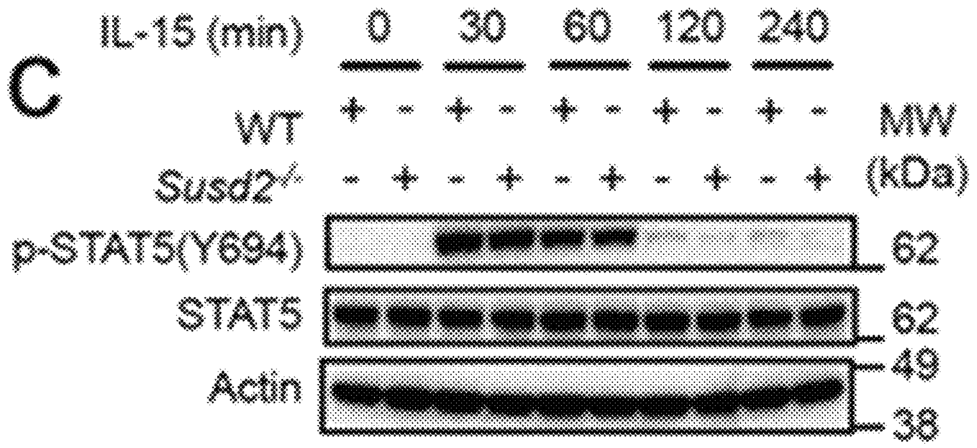
Figure 13D:
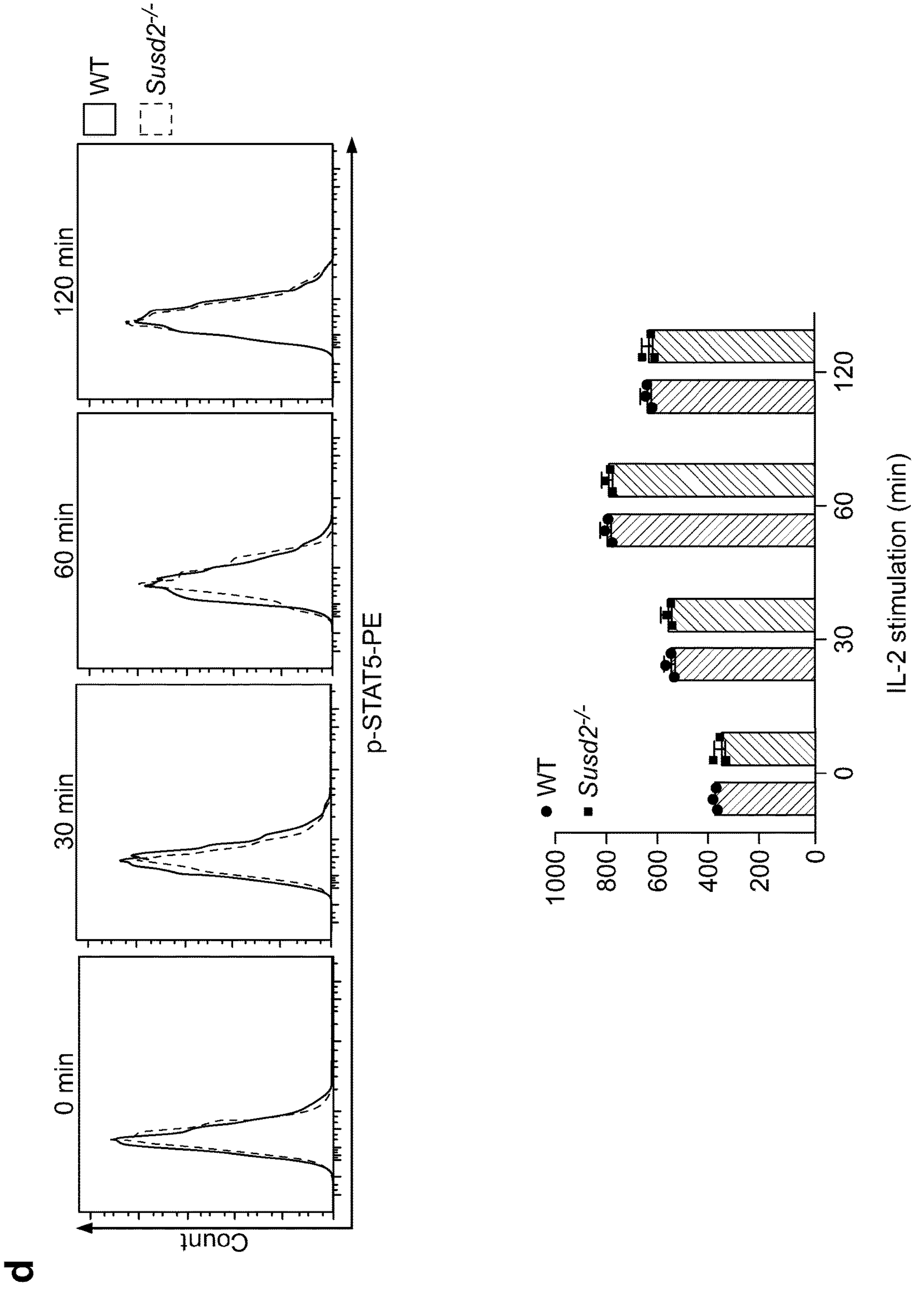
Figure 13E:
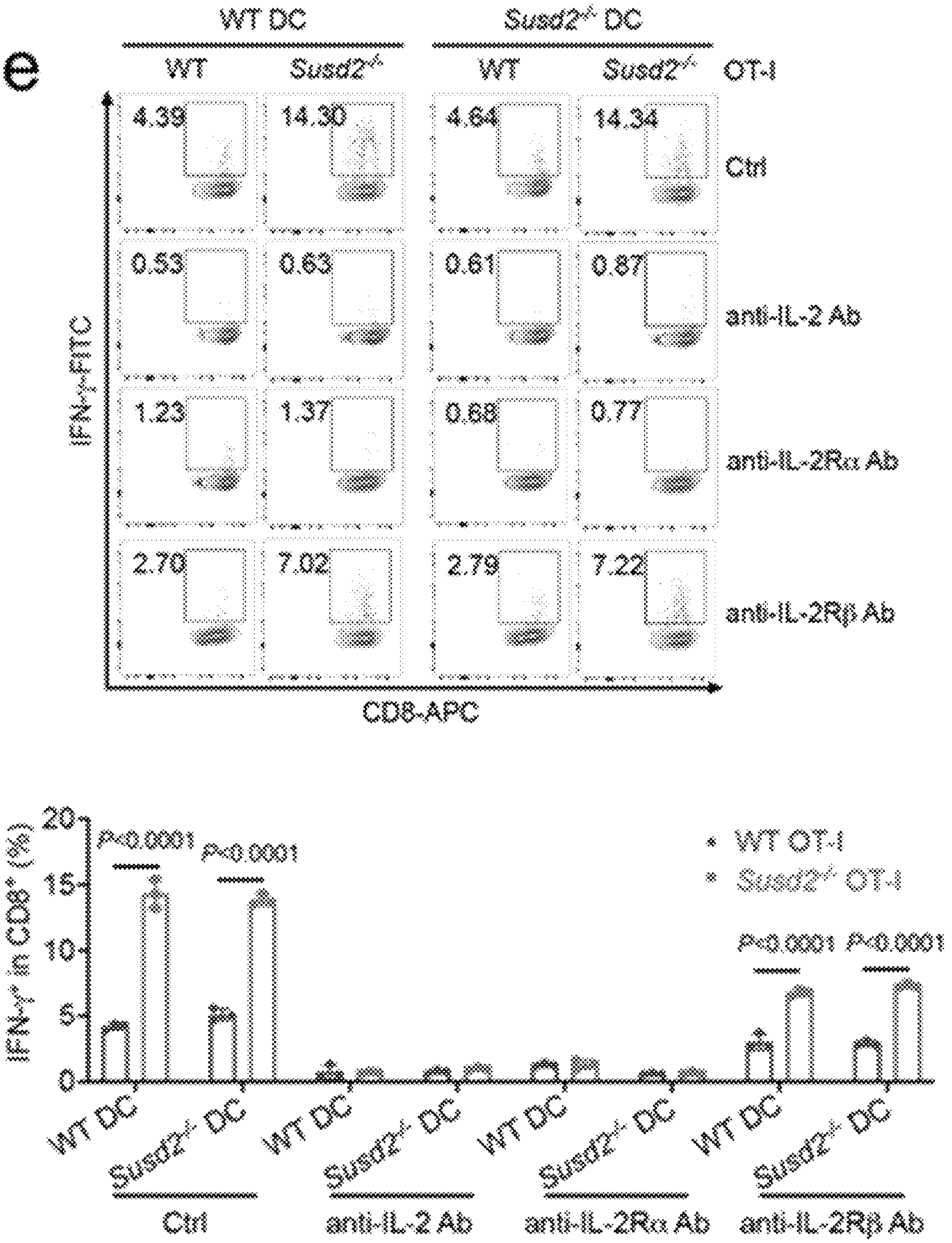
Figure 13E:
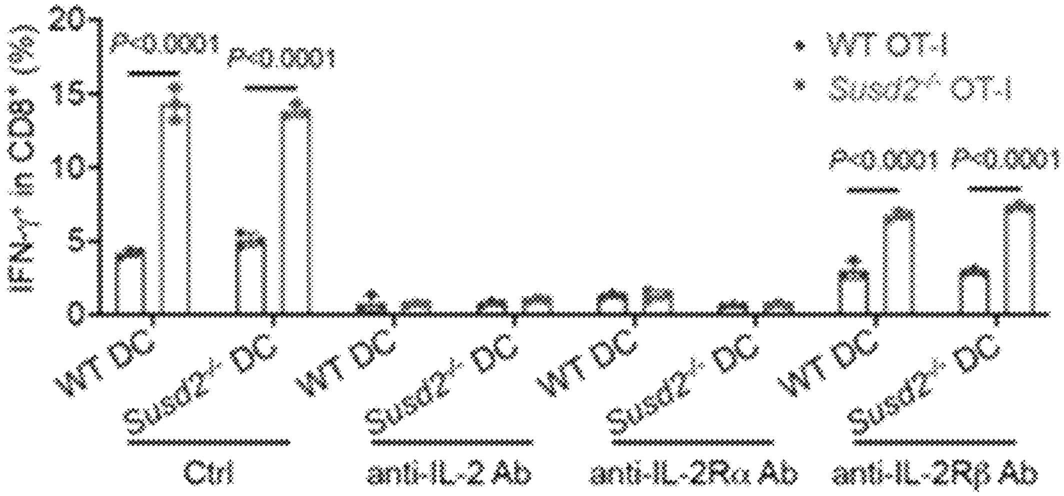
Figure 13F:
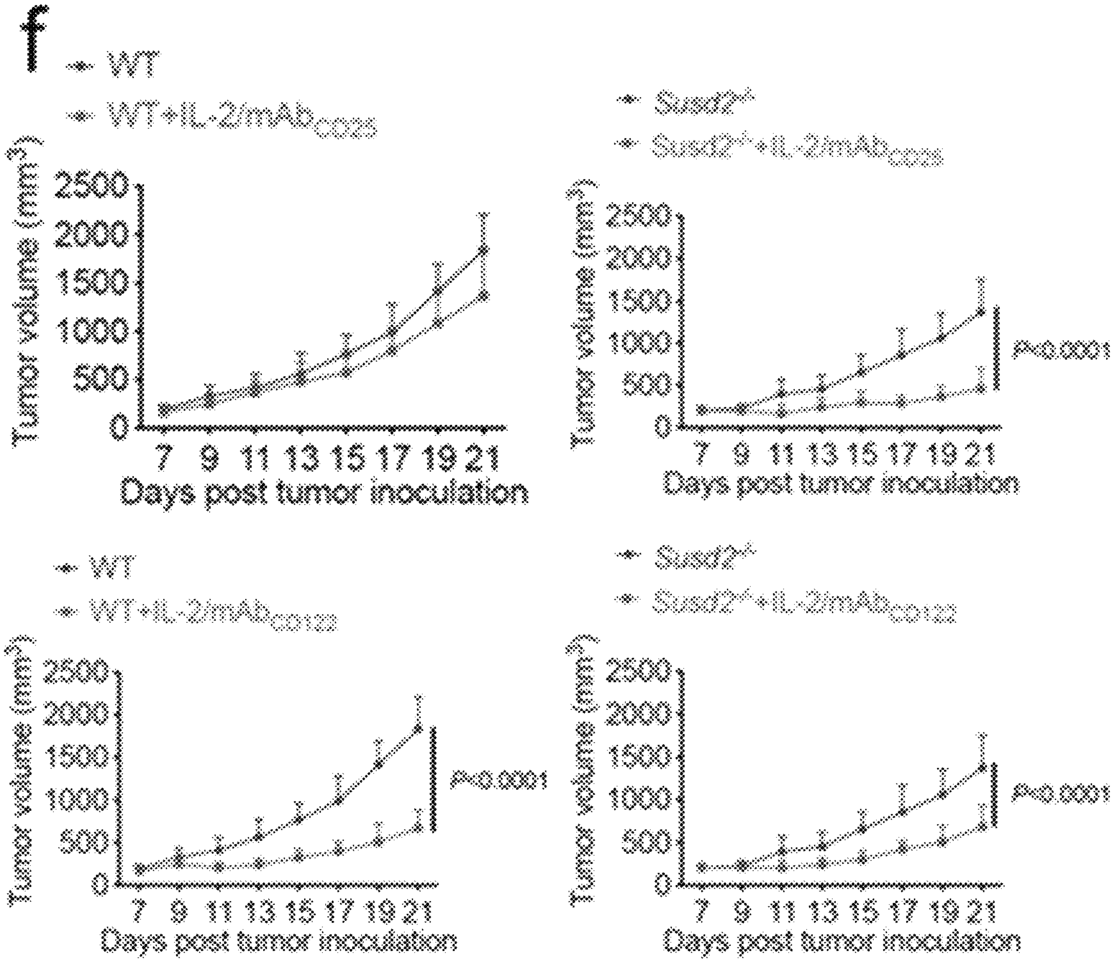

Because IL-2 signaling regulates effector function of $CD8^+$ T cells, SUSD2 interference with IL-2 signaling through the IL-2R was investigated. Stimulation of naïve $CD8^+$ T cells with the 7 chain family cytokine IL-2, IL-7 or IL-15 only induced a slight increase in the expression of Susd2, in contrast to the strong upregulation of Susd2 gene transcription in TCR-activated $CD8^+$ T cells (FIG. 13A). When OVA257-264-activated OT-I T cells were rested overnight before stimulation with either IL-2, IL-7 or IL-15[7], IL-2-treated $Susd2^{-/-}$ OT-I T cells showed enhanced phosphorylation of STAT5, an essential transcription factor downstream of IL-2 signaling, and elevated production of GzmB compared to IL-2-treated wild-type OT-I T cells (FIG. 5A-5B and FIG. 13B), while IL-γ- or IL-15-treated wild-type and $Susd2^{-/-}$ OT-I T cells induced the same amount of p-STAT5 and GzmB (FIG. 5A-5B and FIG. 13C-13D). p-STAT5 was comparable in IL-2-treated wild-type and $Susd2^{-/-}$ Treg cells (FIG. 13E), showing that SUSD2 specifically affected IL-2R signaling in $CD8^+$ T cells. Blocking Abs for IL-2 (clone JES6-1A12) or IL-2Rα (clone PC61), but not blocking Abs for IL-2Rβ (Clone™-β1), abolished the elevated production of IFN-γ and GzmB in $Susd2^{-/-}$ OT-I T cells stimulated with a suboptimal dose (200 ng/ml) of OVA257-264 (FIG. 5C-5D). The enhanced production of IFN-7 (FIG. 13F) and increased apoptosis (FIG. 5E) of $Susd2^{-/-}$ $CD8^+$ T cells cocultured with OVA257-264-pulsed were attenuated by blocking antibodies against IL-2 or IL-2Rα, but not IL-2Rβ. Cell surface expression of IL-2Rα was similar between wild-type and $Susd2^{-/-}$ OT-I T cells (FIG. 5F), showing that enhanced IL-2 signaling in $Susd2^{-/-}$ OT-I T cells was not due to elevated expression of IL-2Rα.

Figure 5G:
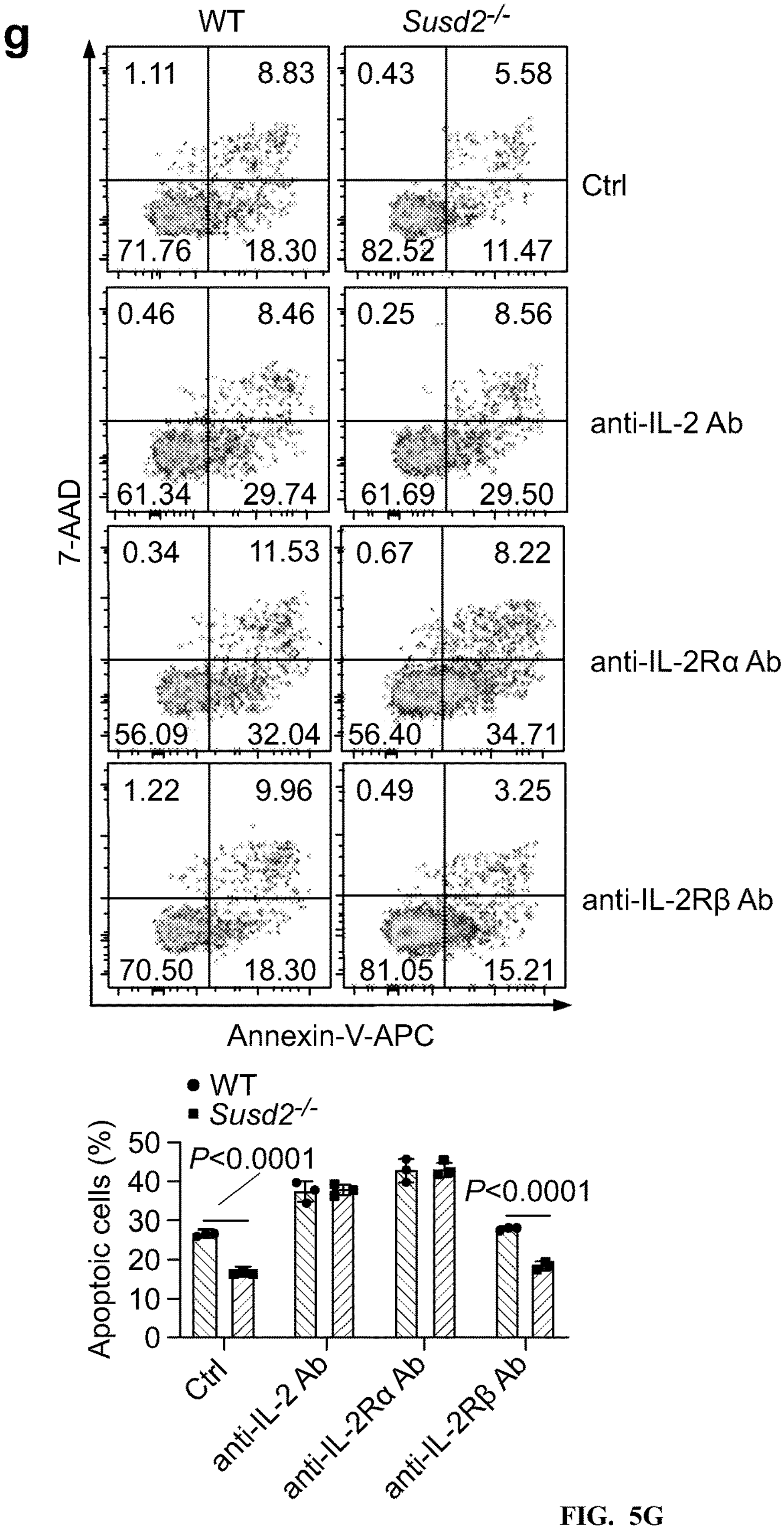
Figure 5H:
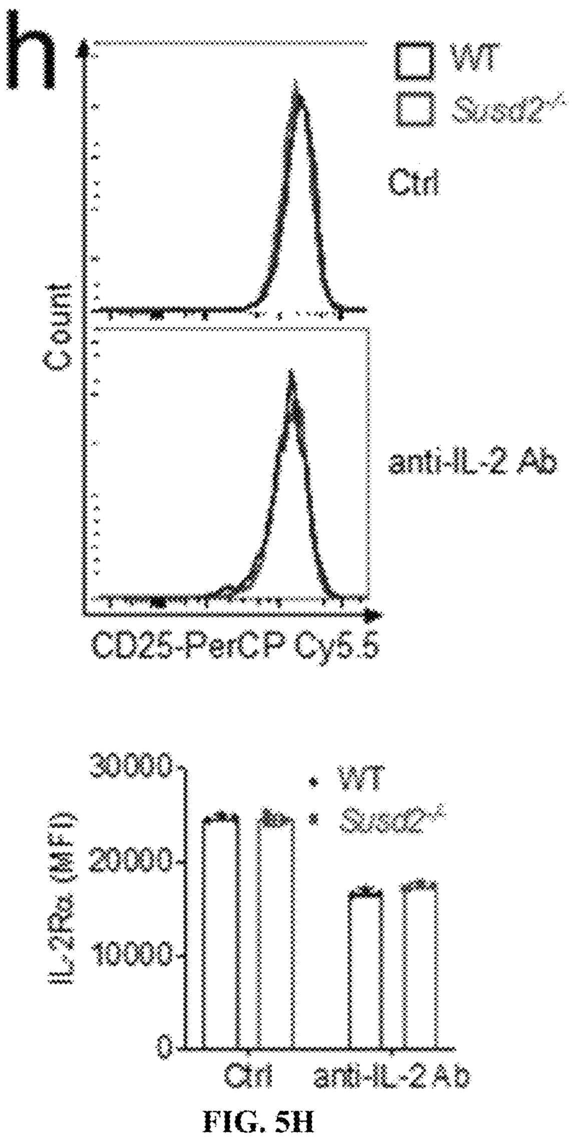
Figure 5I:
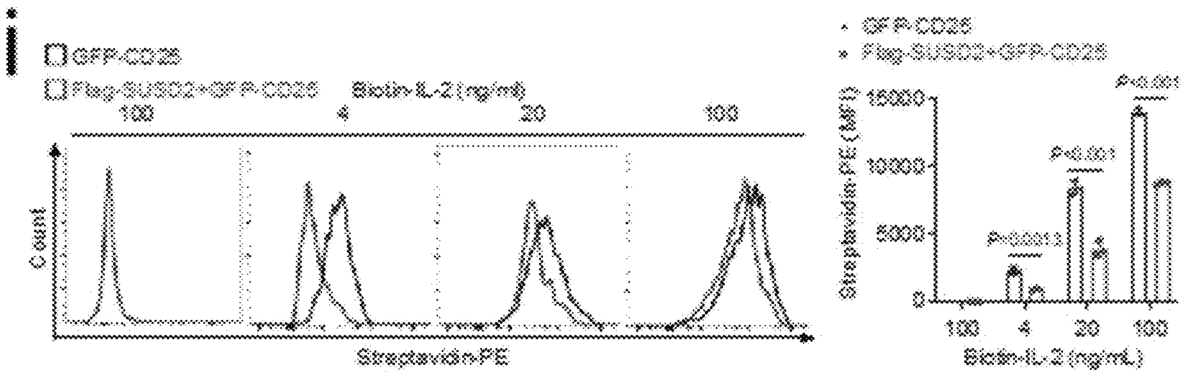
Figure 5J:
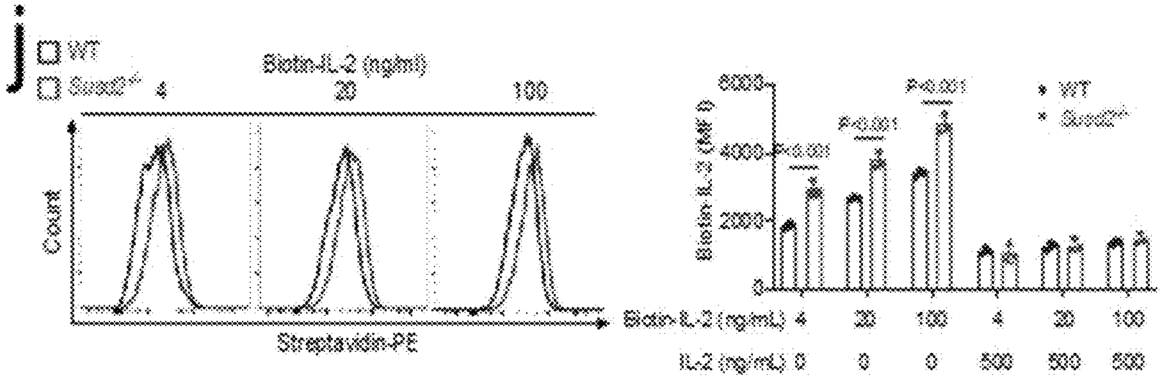

Based on the crystal structure of IL-2 in complex with IL-2Rα, IL-2 engages IL-2Rα along the length of SD1. To test that SUSD2 competitively blocked the SD-dependent binding of IL-2 to IL-2Rα, an IL-2 binding assay was performed using biotinylated IL-2 in 293T cells that overexpressed V5-SUSD2 and/or Flag-IL2RA. Direct binding between SUSD2 and biotinylated IL-2 was not detected, but overexpression of V5-SUSD2 significantly decreased binding of biotinylated IL-2 to overexpressed Flag-IL2RA (FIG. 5G). Increased binding of biotinylated IL-2 to OVA257-264-activated $Susd2^{-/-}$ OT-I T cells was observed compared to similarly treated wild-type OT-I T cells (FIG. 5H), showing that SUSD2 negatively regulated IL-2R signaling by interfering with IL-2-IL-2Rα binding.

Figure 13G:
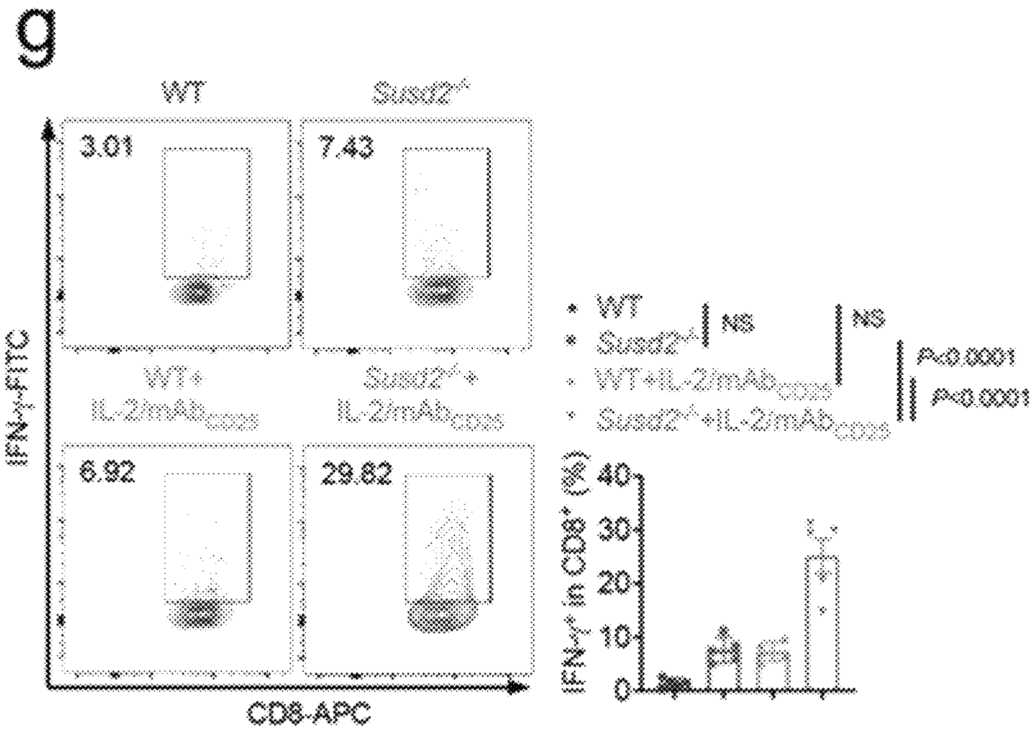
Figure 13H:
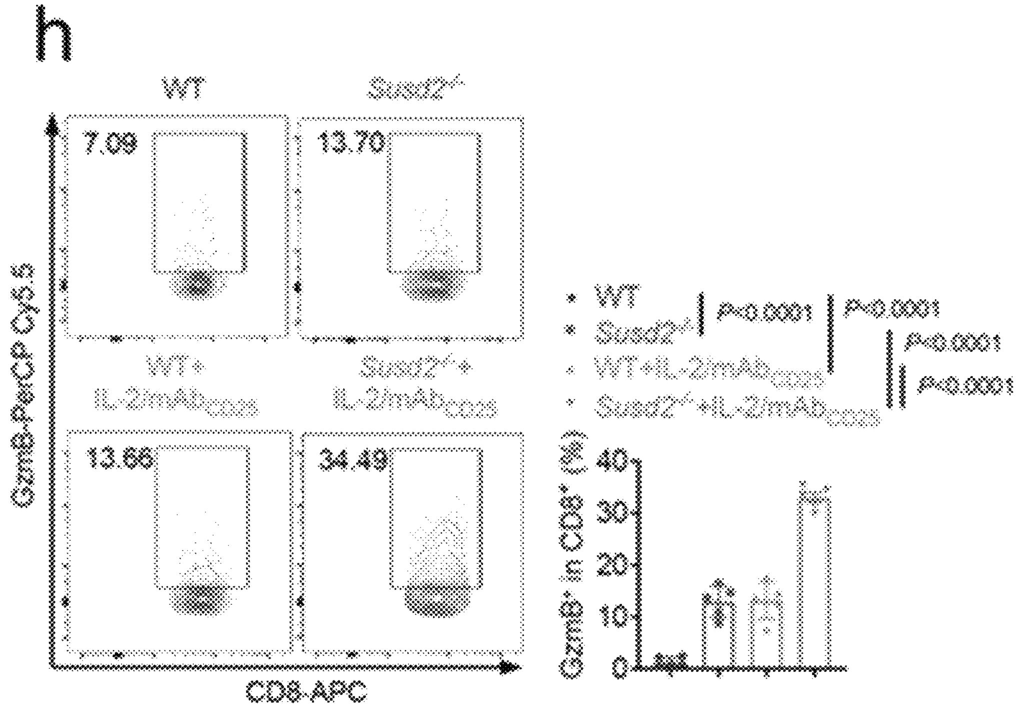
Figure 13I:
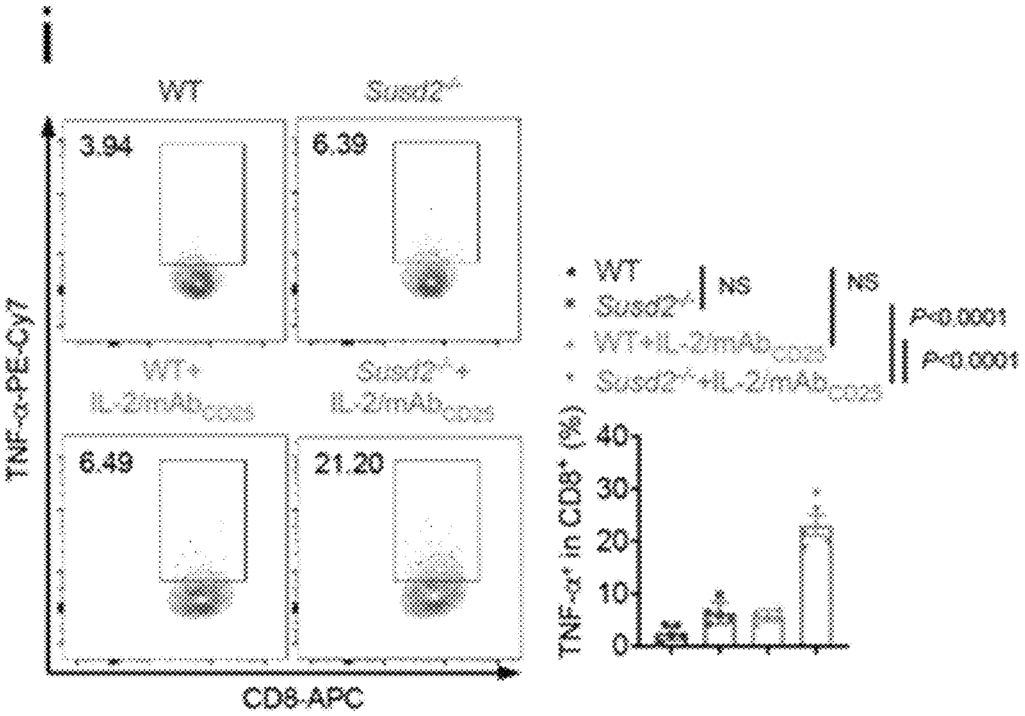

Selective targeting of IL-2/IL-2 Ab immune complexes on IL-2 receptors improves IL-2 immunotherapy against tumors. To examine the impact of SUSD2 on IL-2R signaling during an antitumor response in vivo, the efficacy of IL-2/IL-2 Ab complexes in limiting the growth of B16-F10 tumors was compared in wild-type and $Susd2^{-/-}$ mice. An IL-2Rα-targeting complex (IL-2/AbCD25, which is mouse IL-2 complexed with IL-2 Ab, clone JES6-1A12) and a CD122-targeting complex (IL-2/AbCD122, mouse IL-2 complexed with IL-2 Ab, clone S4B6-1) was used. IL-2/AbCD25 had a minimal effect on tumor growth in wild-type mice compared to PBS injection (FIG. 13G), but significantly blunted the growth of B16-F10 tumors in $Susd2^{-/-}$ mice (FIG. 6G), while IL-2/AbCD122 caused a similar reduction of tumor growth in wild-type and $Susd2^{-/-}$ mice (FIG. 13H). IL-2/AbCD25-treated $Susd2^{-/-}$ mice had significantly increased percentages of intratumoral $CD8^+$ T cells that produced IFN-γ, GzmB and TNF compared to IL-2/AbCD25-treated wild-type mice (FIG. 13I-13K). Collectively, these findings showed an inhibitory effect of SUSD2 on IL-2R function.

SUSD2 Inhibits $CD8^+$ T Cell Antitumor Function Via SD

Figure 6A:
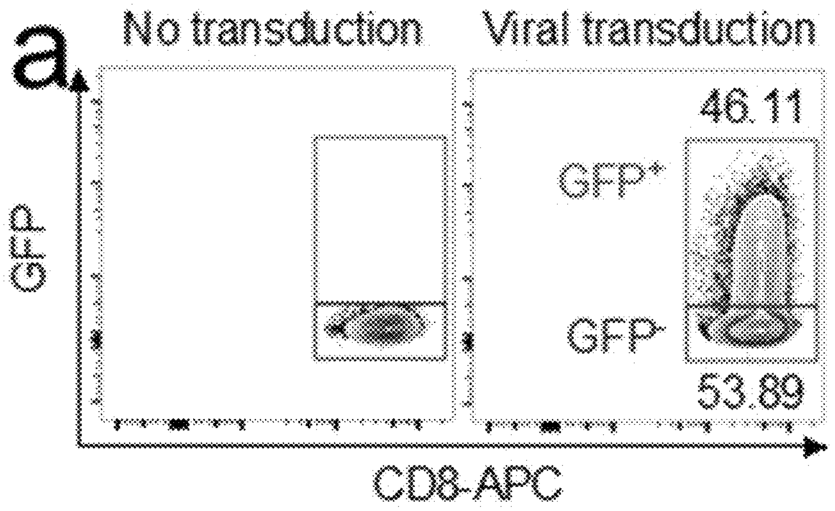
FIGS. 6A-6M show SUSD2-IL-2Rα interaction impairs antitumor effector function of $CD8^+$ T cells.
Figure 6B:
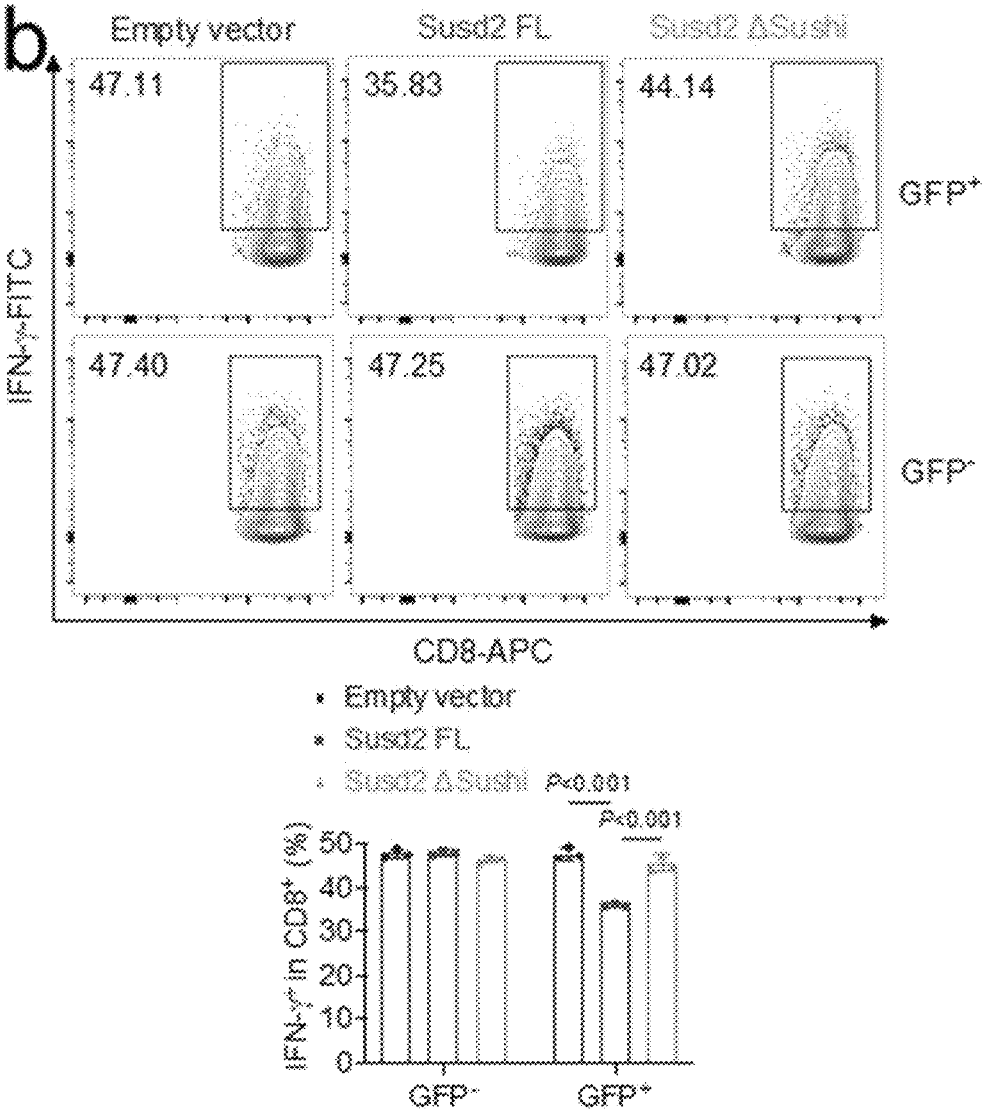
Figure 6C:
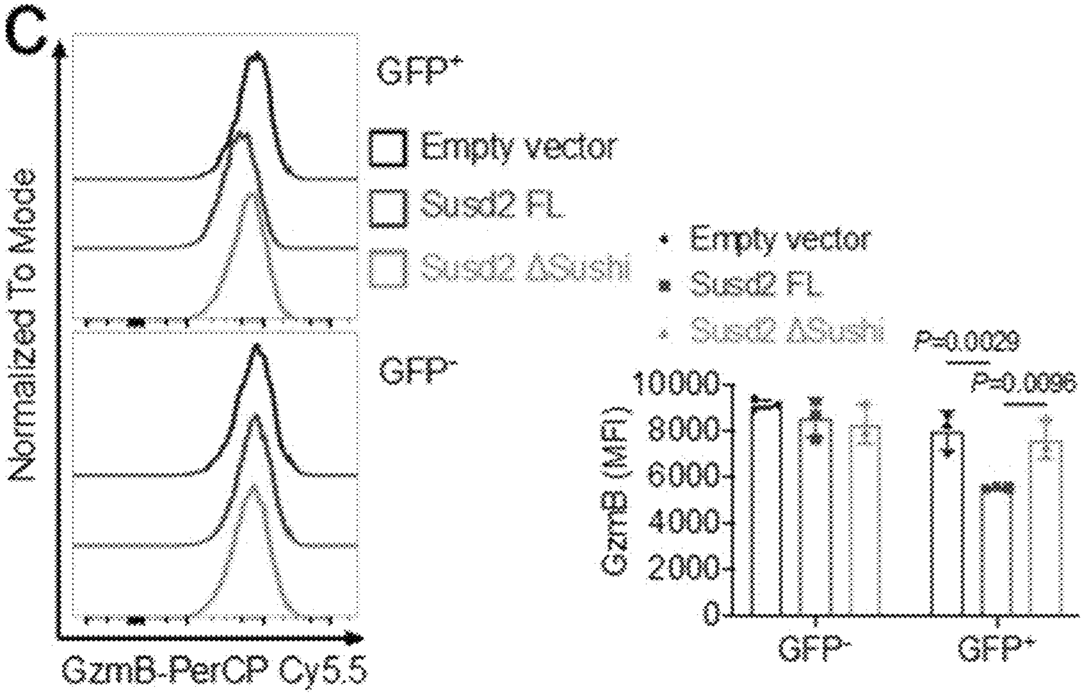
Figure 6D:
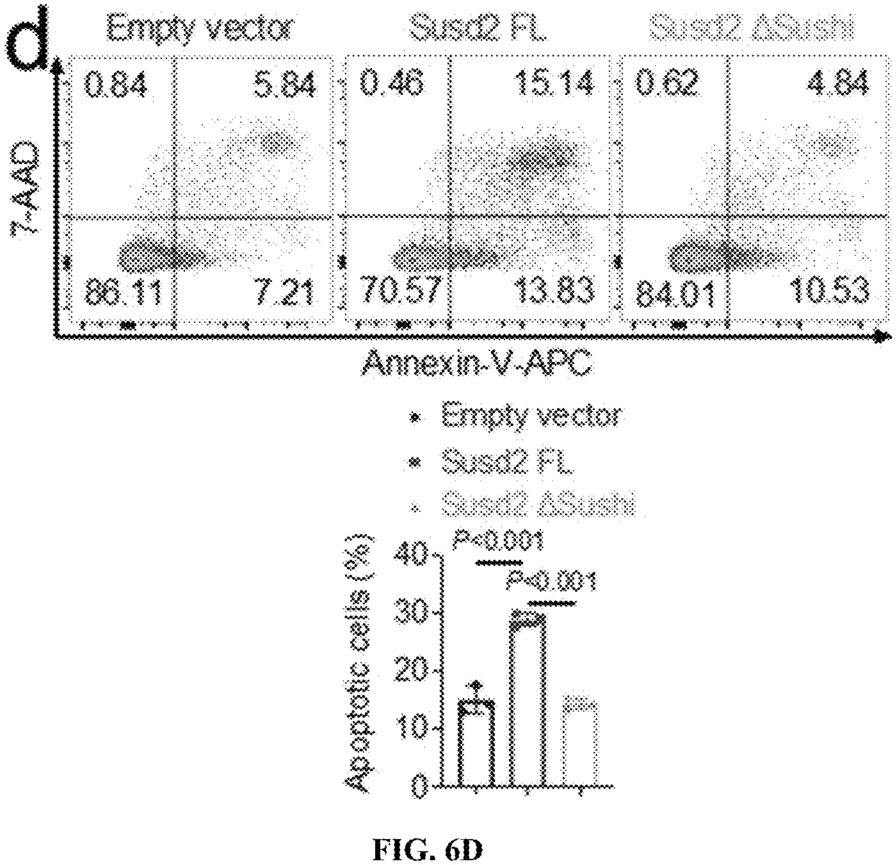
Figure 6E:
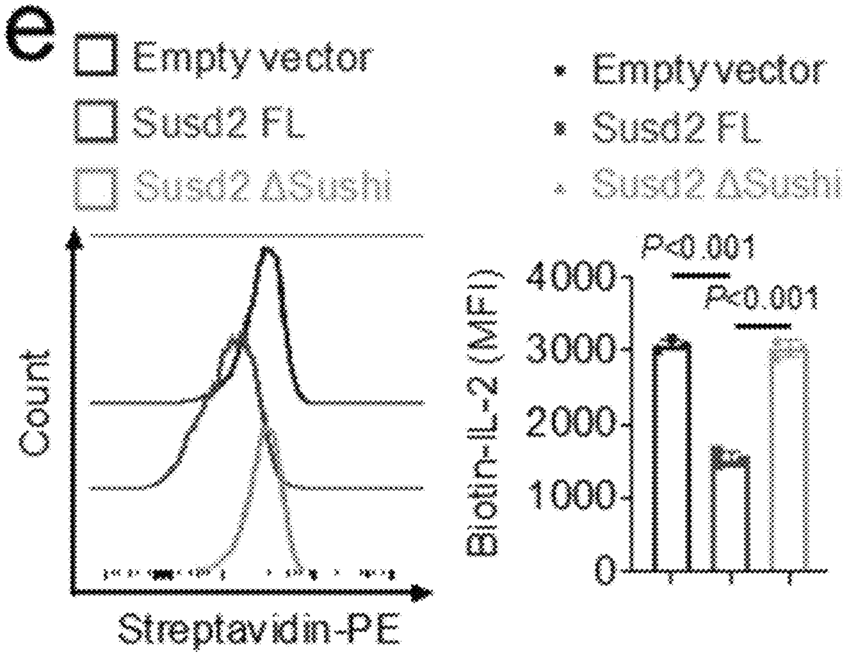
Figure 6F:
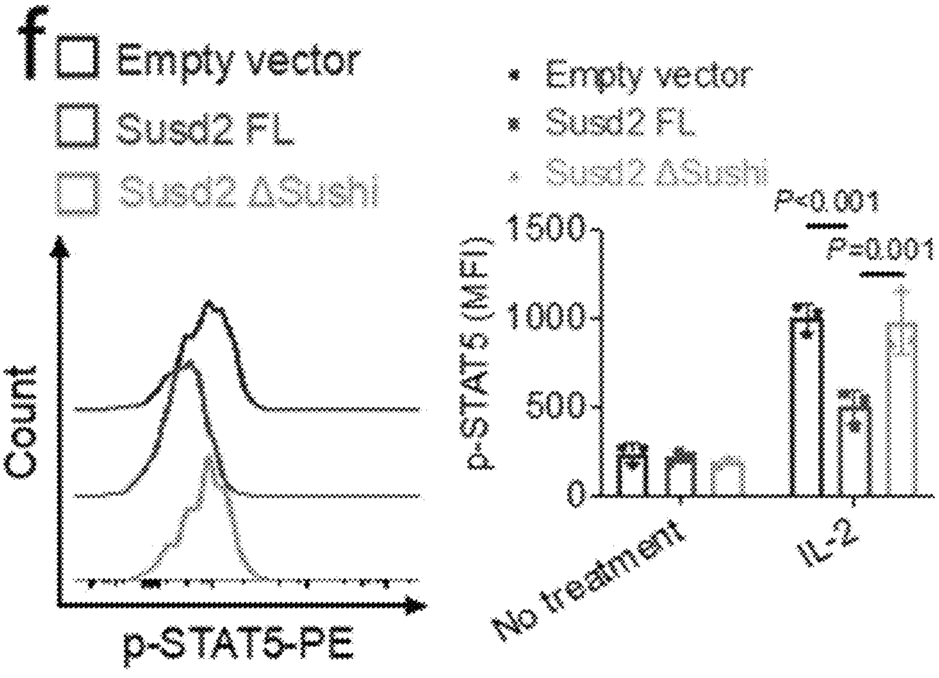

Next, the interaction between SUSD2 and IL-2Rα was examined for requiring the inhibitory effect of SUSD2 on $CD8^+$ T cell activation. In OVA257-264-activated $Susd2^{-/-}$ OT-I T cells retrovirally transduced with GFP-tagged full-length SUSD2 ($SUSD2^{FL}$-GFP), $SUSD2^{\Delta SD}$-GFP or EV-GFP with about 50% of transduction efficiency (FIG. 6A), decreased production of IFN-7 and GzmB (FIG. 6B-6C) and increased apoptosis (FIG. 6D) was observed in $GFP^+$ OT-I T cells reconstituted with $SUSD2^{FL}$-GFP, but not with $SUSD2^{\Delta SD}$-GFP compared to cells reconstituted with EV-GFP. Moreover, transduction of $Susd2^{-/-}$ OT-I T cells with $SUSD2^{FL}$-GFP, but not $SUSD2^{\Delta SD}$-GFP, inhibited the binding of biotinylated IL-2 to $Susd2^{-/-}$ OT-I T cells (FIG. 6E) and IL-2-induced STAT5 phosphorylation (FIG. 6F). These results showed that loss of SUSD2 interaction with IL-2Rα ablated its inhibitory effect on $CD8^+$ T cell effector function in vitro.

Figure 6G:
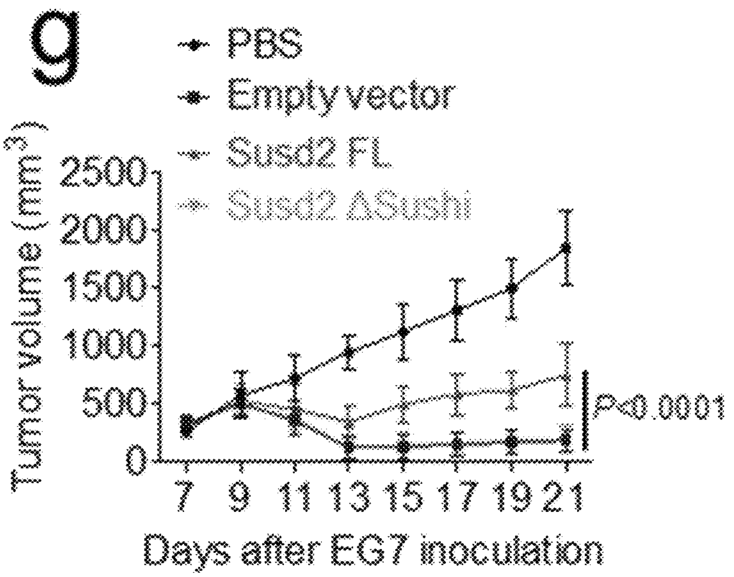
Figure 6H:
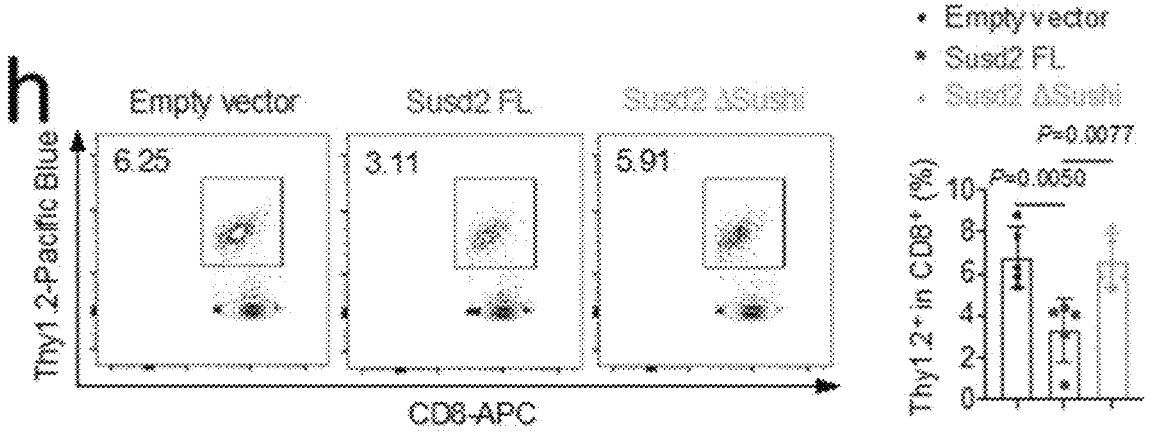
Figure 6I:
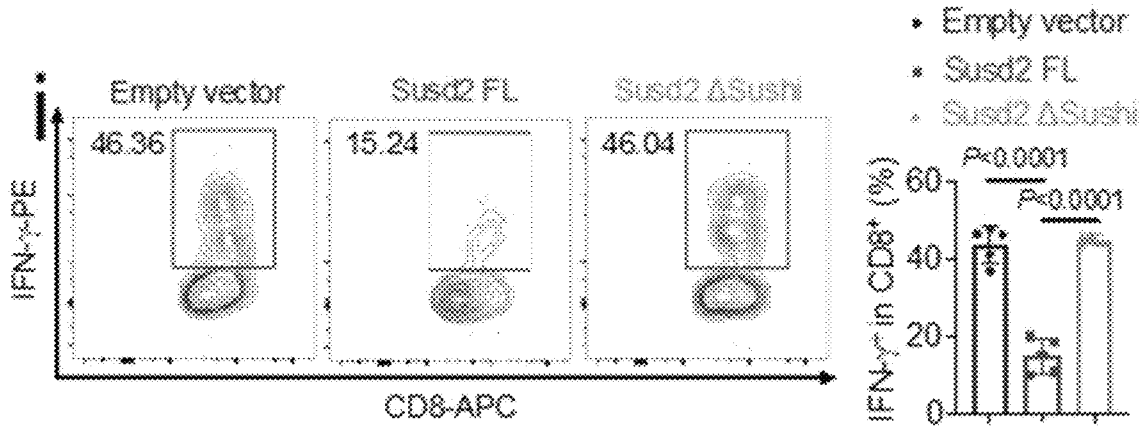
Figure 6J:
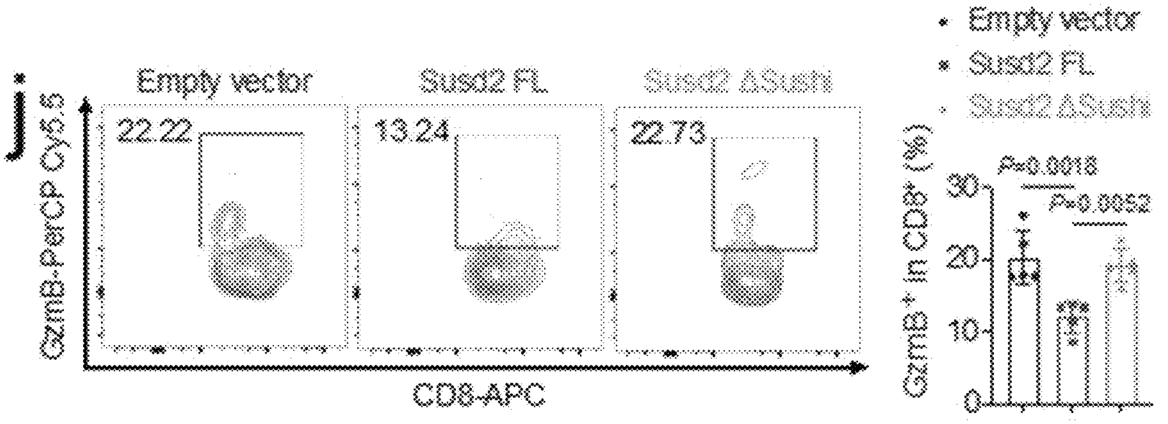
Figure 6K:
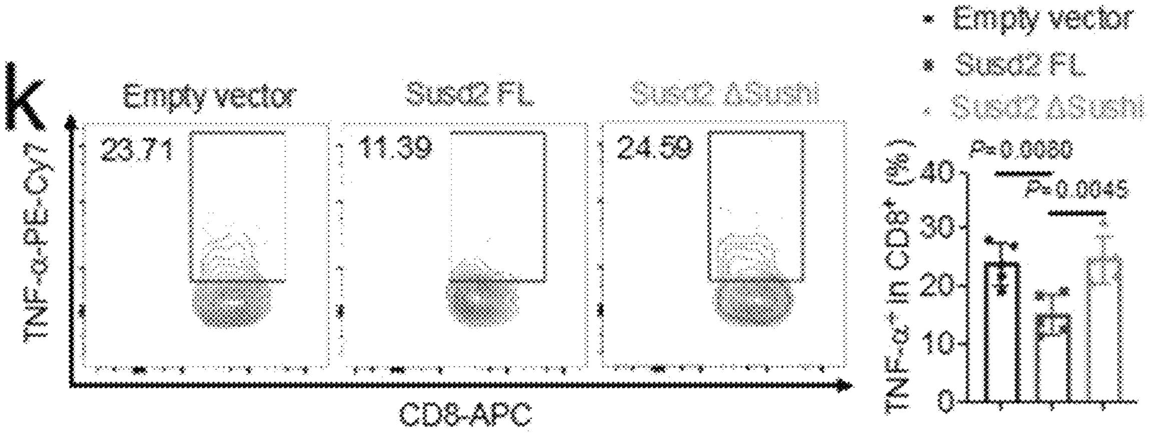
Figure 6L:
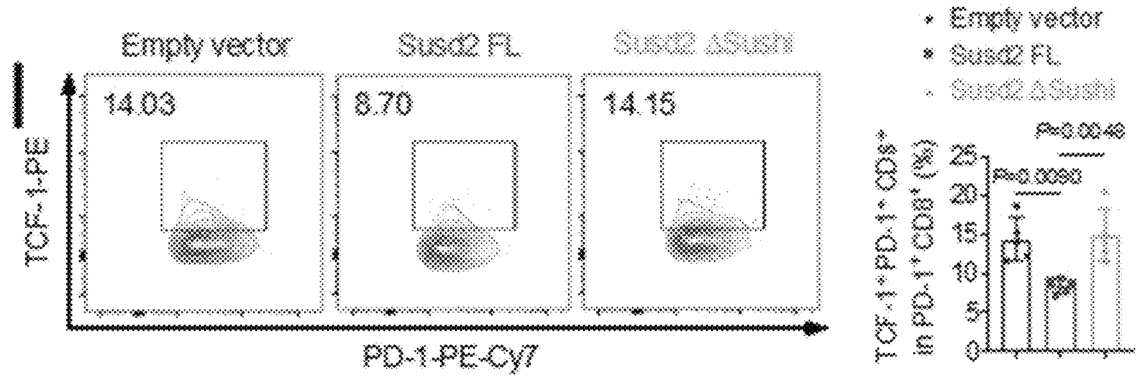
Figure 6M:
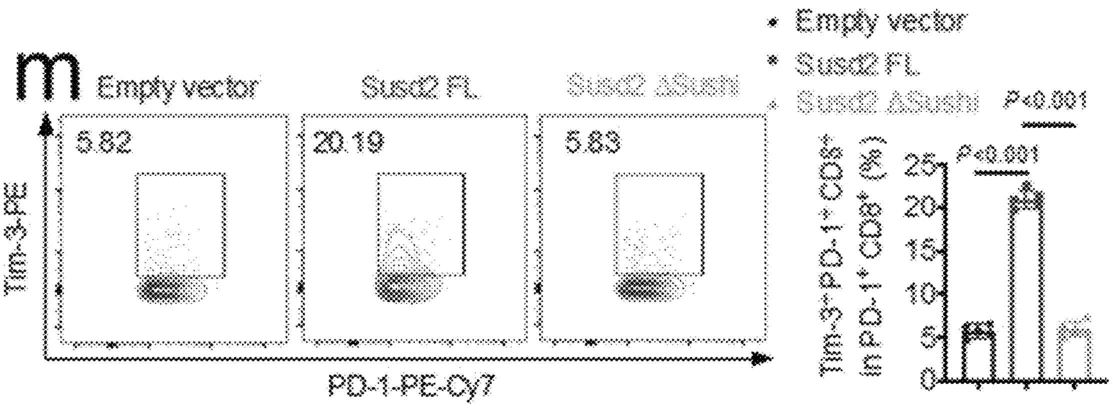
Figure 15:
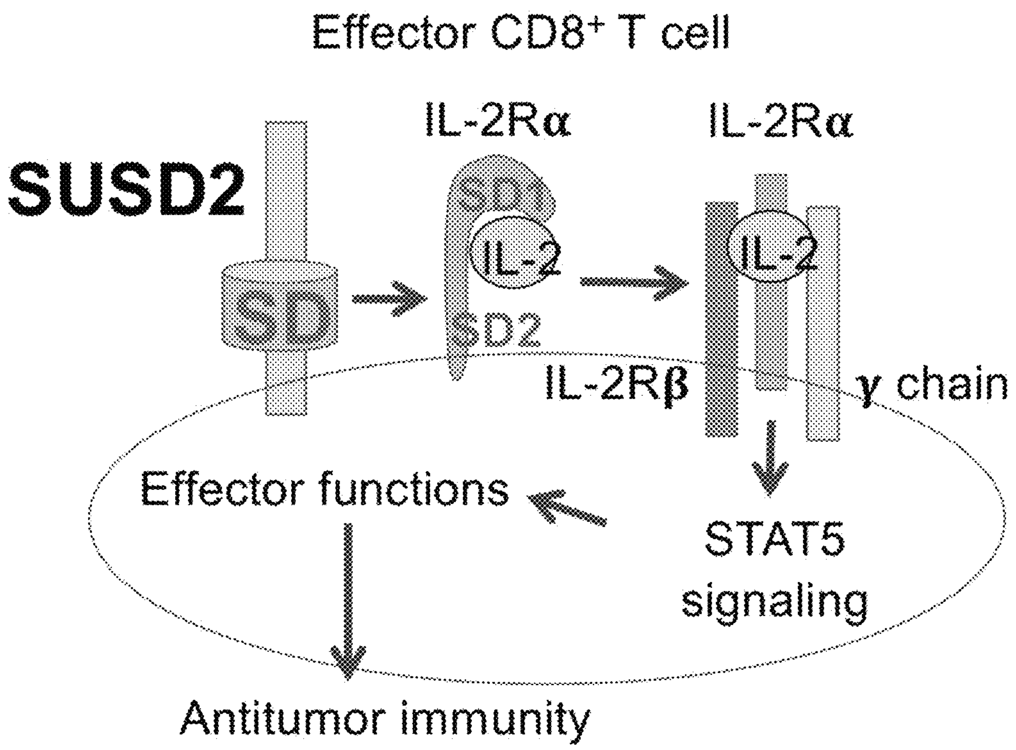
FIG. 15 shows a model for an inhibitory role of SUSD2 in effector CD8$^+$ T cell antitumor immunity by modulating IL-2R signaling. The present disclosure has identified SUSD2 as a negative regulator of IL-2-mediated effector CD8$^+$ T cell functions and antitumor immunity. Both SUSD2 and IL-2Rα chain (IL-2Rα) contain the sushi domain (SD). Genetic ablation of SUSD2 (Susd2$^{-/-}$) leads to elevated IFN-γ, GzmB and TNF production in effector CD8$^+$ T cells and improved tumor growth control in multiple syngeneic tumor models. Mechanistically, SD-dependent interaction between SUSD2 and IL-2Rα competitively inhibits IL-2-IL-2Rα binding, leading to an attenuated IL-2R signaling. Therefore, SUSD2 represents a therapeutic target of tumor immunotherapy. Green and red arrows indicate promoting and inhibiting effect, respectively.

To determine whether the Susd2-IL-2Rα interaction modulated the antitumor effector function of $CD8^+$ T cells in vivo, $Thy1.2^+Susd2^{-/-}$ OT-I T cells transduced with $SUSD2^{FL}$-GFP, $SUSD2^{\Delta SD}$-GFP or EV-GFP were adoptively transferred into $Thy1.1^+$ mice challenged with EG7 tumor cells 7 days before cell transfer. While $SUSD2^{FL}$-GFP $Susd2^{-/-}$ OT-I T cells exhibited impaired capacity to control EG7 tumor growth, $SUSD2^{\Delta SD}$-GFP $Susd2^{-/-}$ OT-I T cells controlled tumor growth at levels comparable to EV-GFP Susd2$^{-/-}$ OT-I T cells (FIG. 6G). SUSD2$^{FL}$-GFP, but not SUSD2$^{\Delta SD}$-GFP Susd2$^{-/-}$ OT-I T cells had attenuated tumor infiltration, decreased production of IFN-γ, GzmB and TNF (FIG. 6H) and significantly decreased about 42% of CD8$^+$ TExP cell (FIG. 6I) and increased about 77% of CD8$^+$ TExT cells (FIG. 6J) compared to EV-GFP Susd2$^{-/-}$ OT-I T cells. This showed that the SUSD2-IL-2Rα interaction was required for the inhibitory role of SUSD2 on the antitumor effector function of CD8$^+$ T cells (FIG. 15).

Deletion of Susd2 Improves Antitumor Efficacy of CAR T Cells.

Figure 7A:
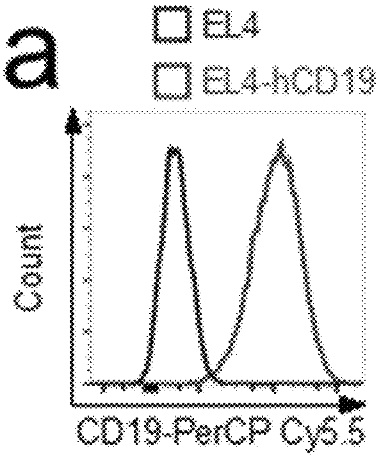
FIGS. 7A-7S show deletion of Susd2 improves antitumor efficacy of CAR T cells.
Figure 7B:
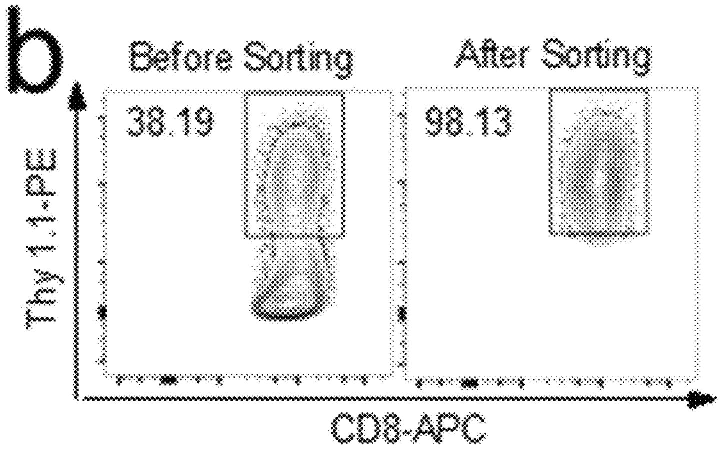
FIG. 7B-7E shows the frequencies of IFN-$\gamma^+CD8^+$ T cells, $GzmB^+CD8^+$ T cells, $TNF^+CD8^+$ T cells, annexin $V^+$7-$AAD^+CD8^+$ T cells, PD-$1^+$ $CD8^+$ T cells, and $LAG3^+$ $CD8^+$ T cells in EL4-hCD19 tumors isolated from $Rag2^{-/-}$ mice that received WT or $Susd2^{-/-}$ CAR T cells at day 18 post tumor inoculation.
Figure 7C:
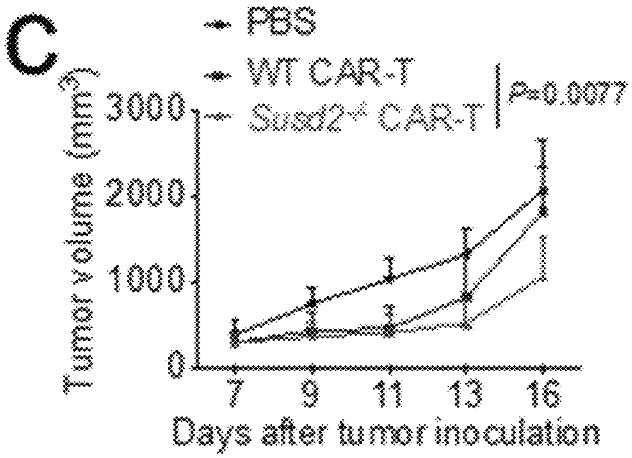
Figure 7D:
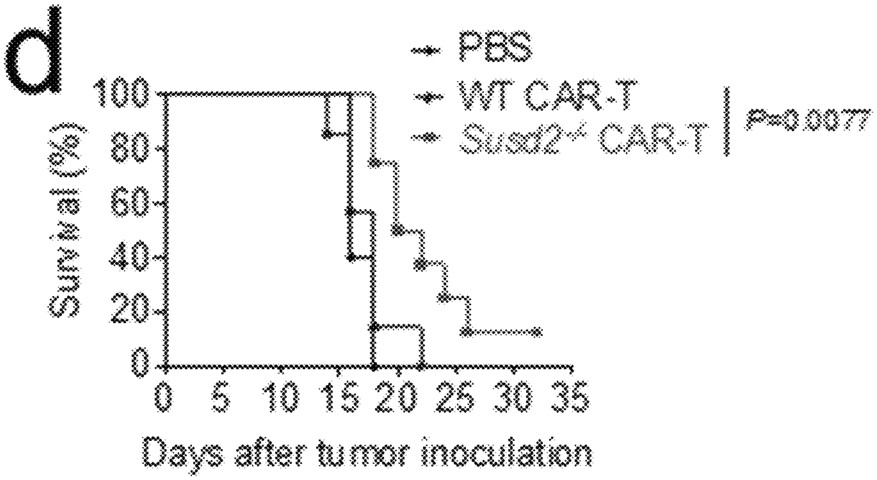
Figure 7E:
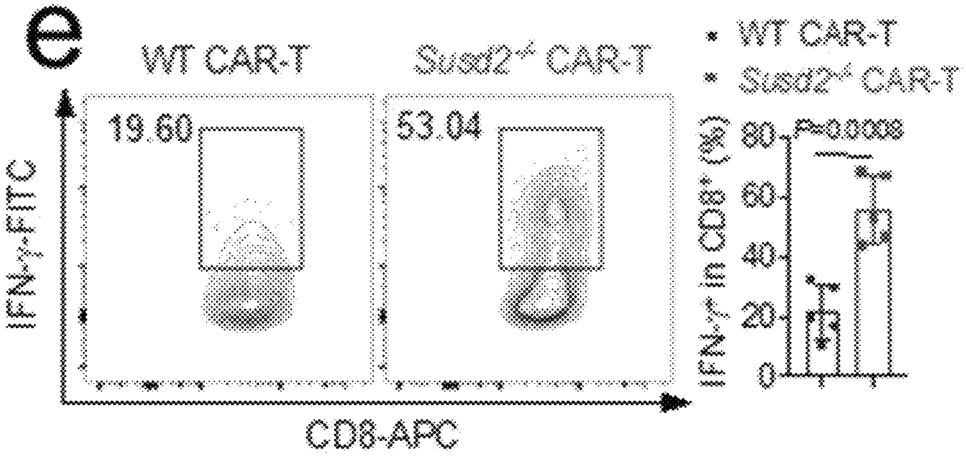
Figure 7F:
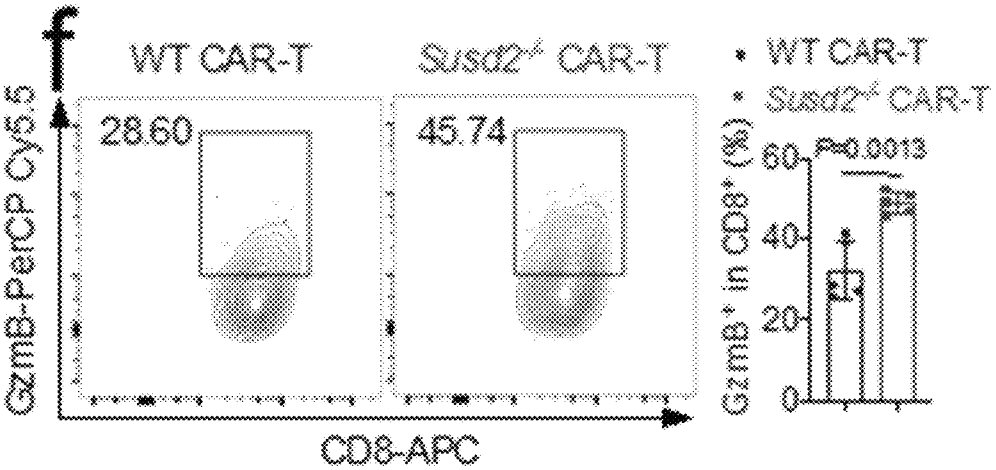
FIG. 7F shows the tumor growth and survival in EL4-hCD19-bearing $Rag2^{-/-}$ mice that received CAR T cells containing either scrambled gRNA (sgRNA) or Susd2 gRNA at day 7 post tumor inoculation.
Figure 7G:
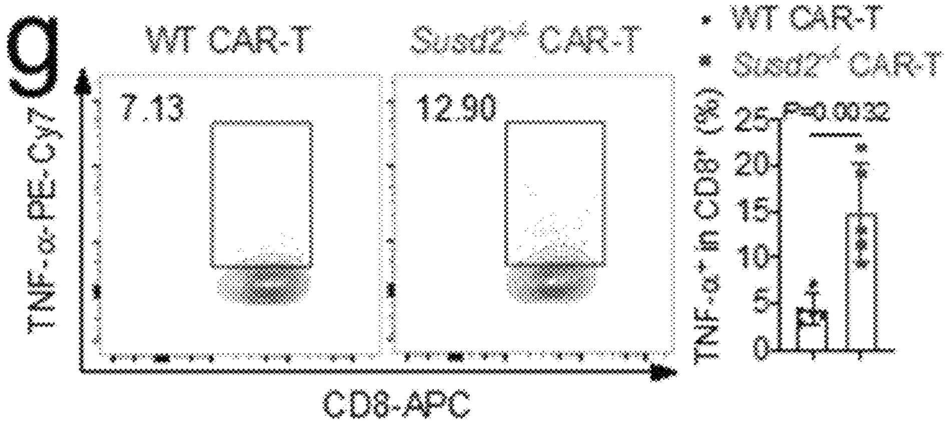
Figure 7H:
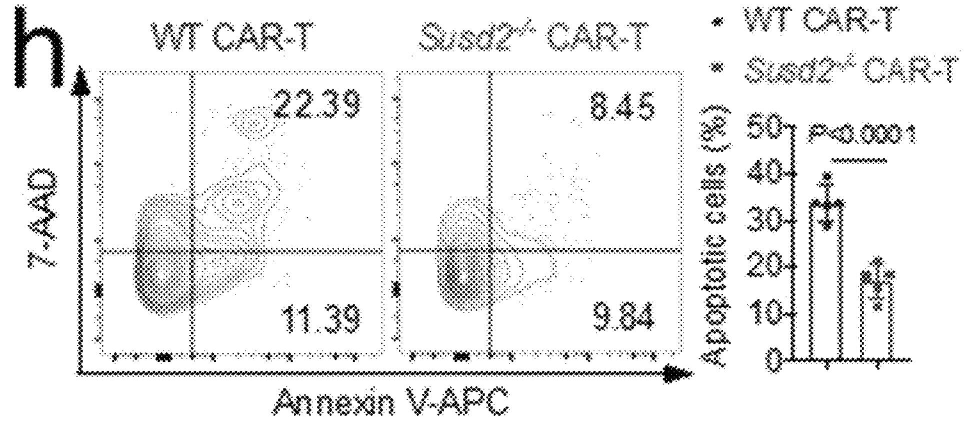
Figure 7I:
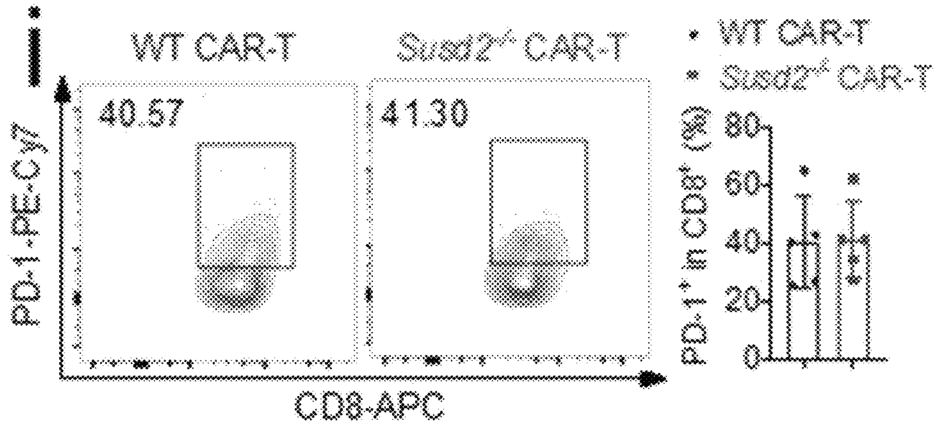
Figure 7J:
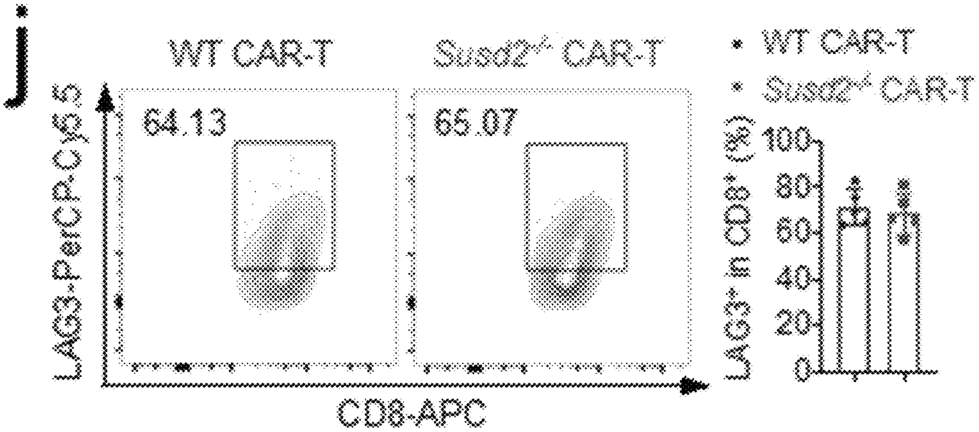
Figure 7K:
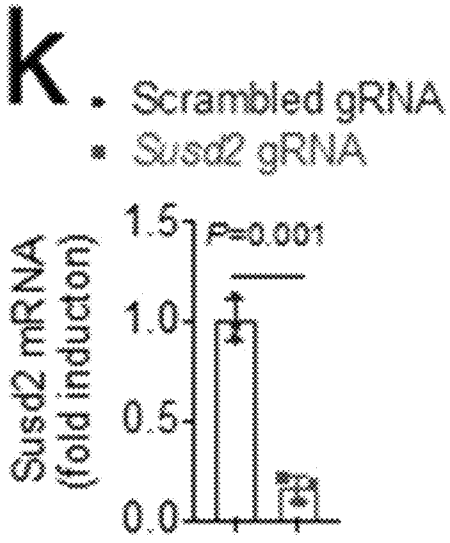
Figure 7L:
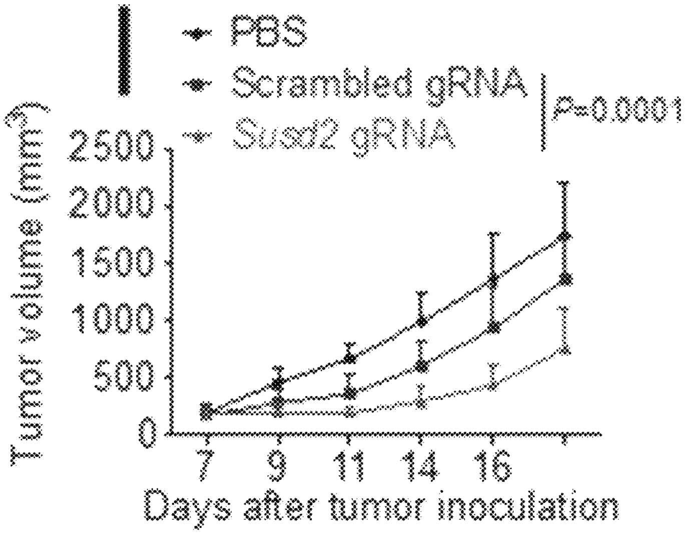
Figure 7M:
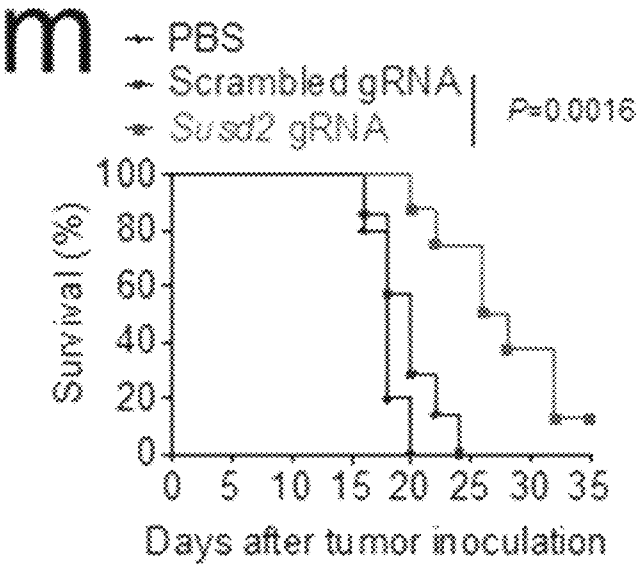
Figure 7N:
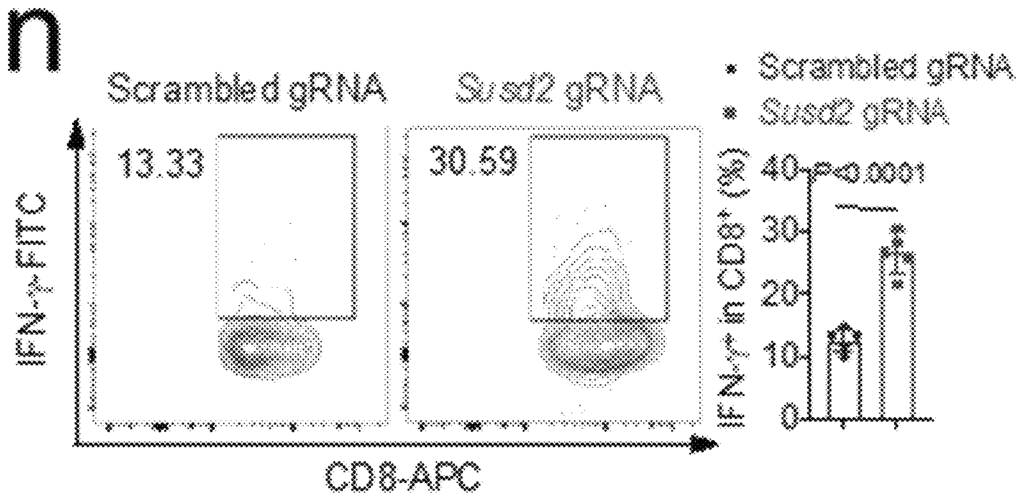
Figure 7O:
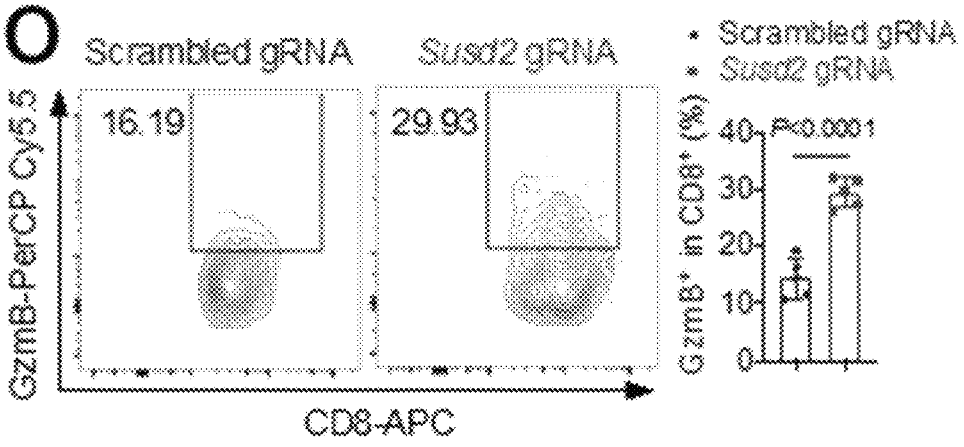
Figure 7P:
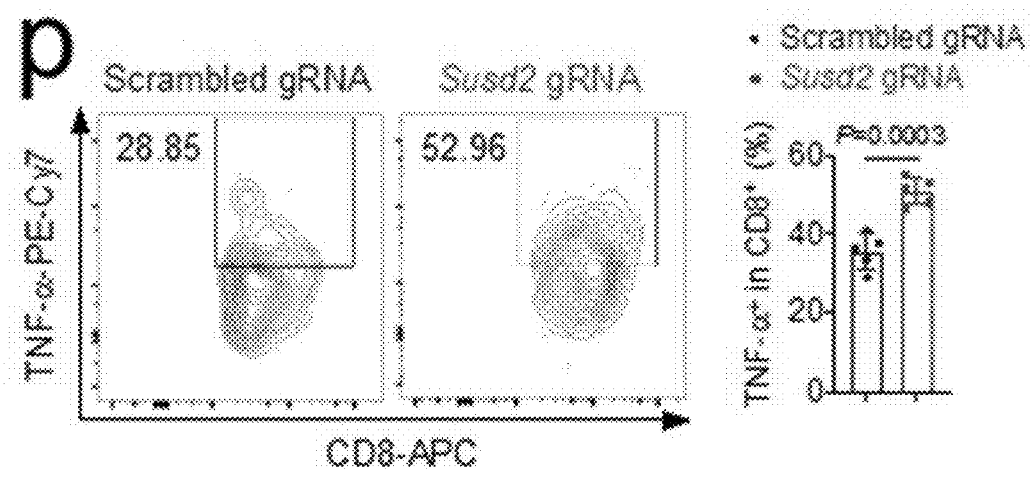
Figure 7Q:
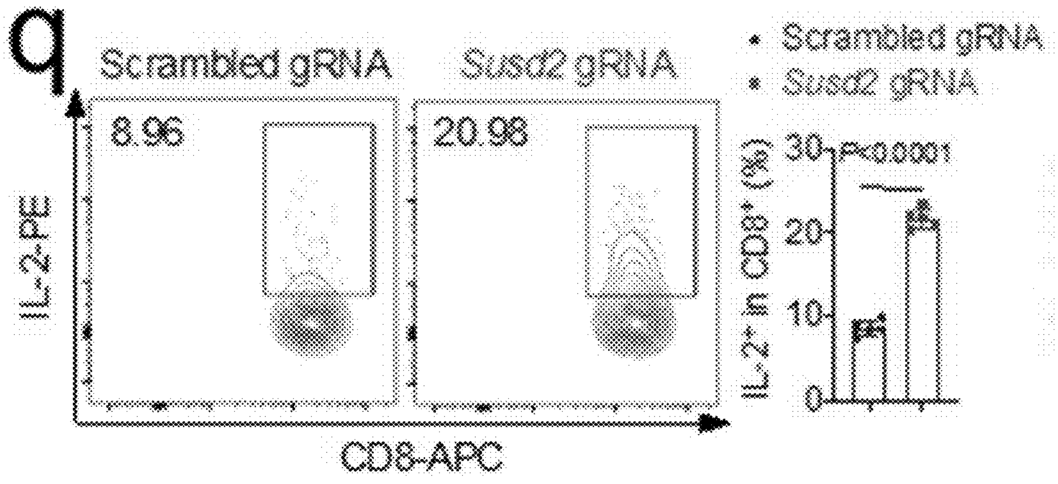
Figure 7R:
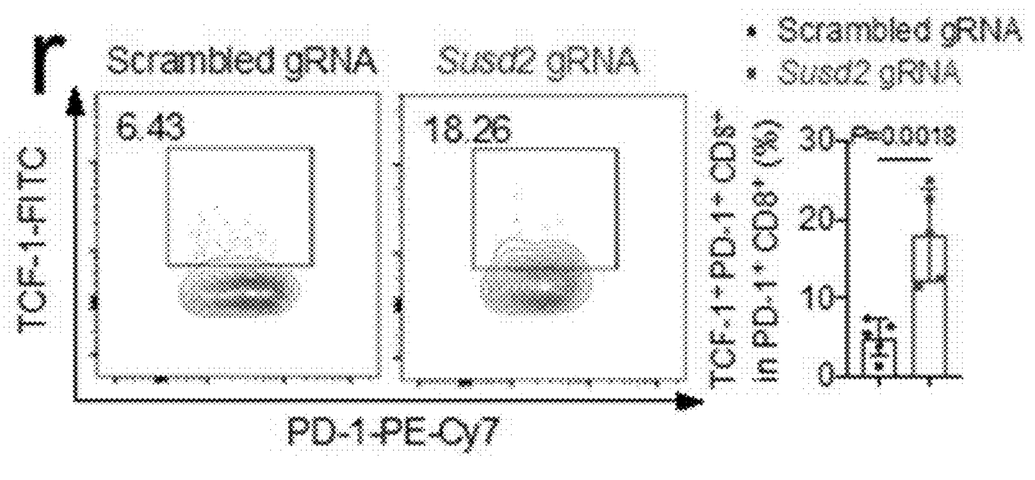
Figure 7S:
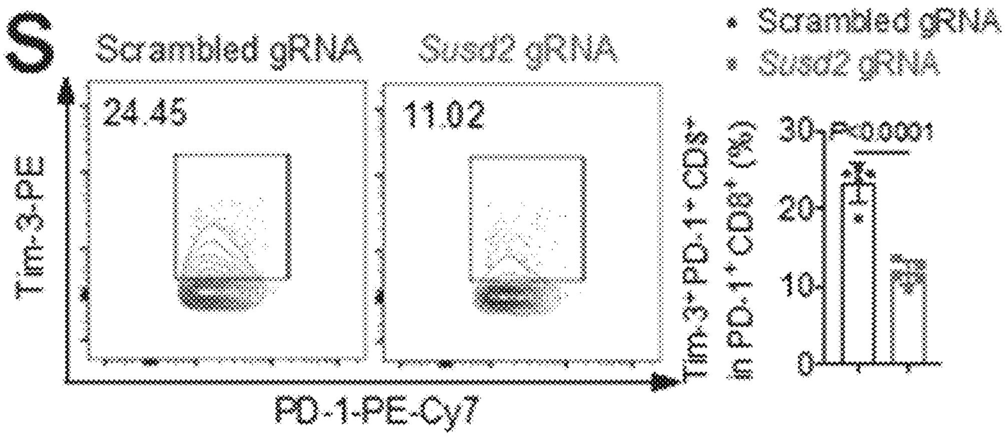
Figure 14A:
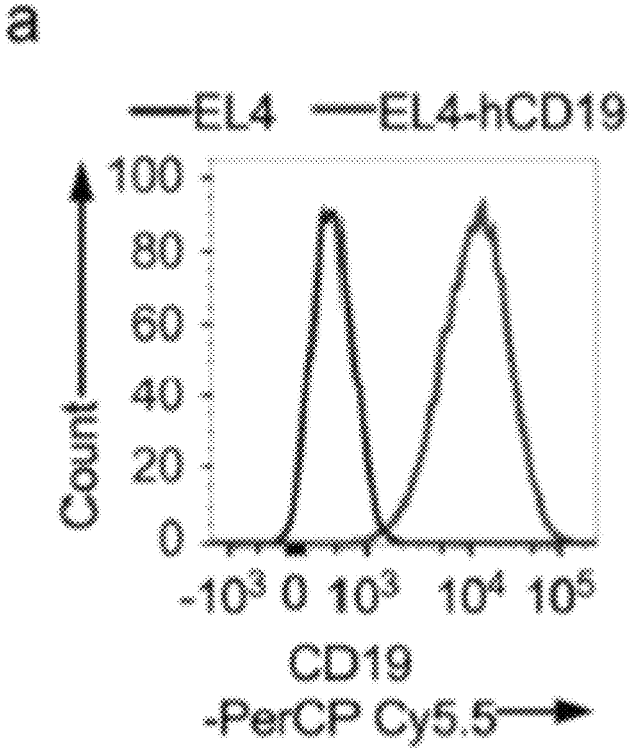
FIGS. 14A-14C show the identification of EL4-hCD19 cells and CAR T cells.
Figure 14B:
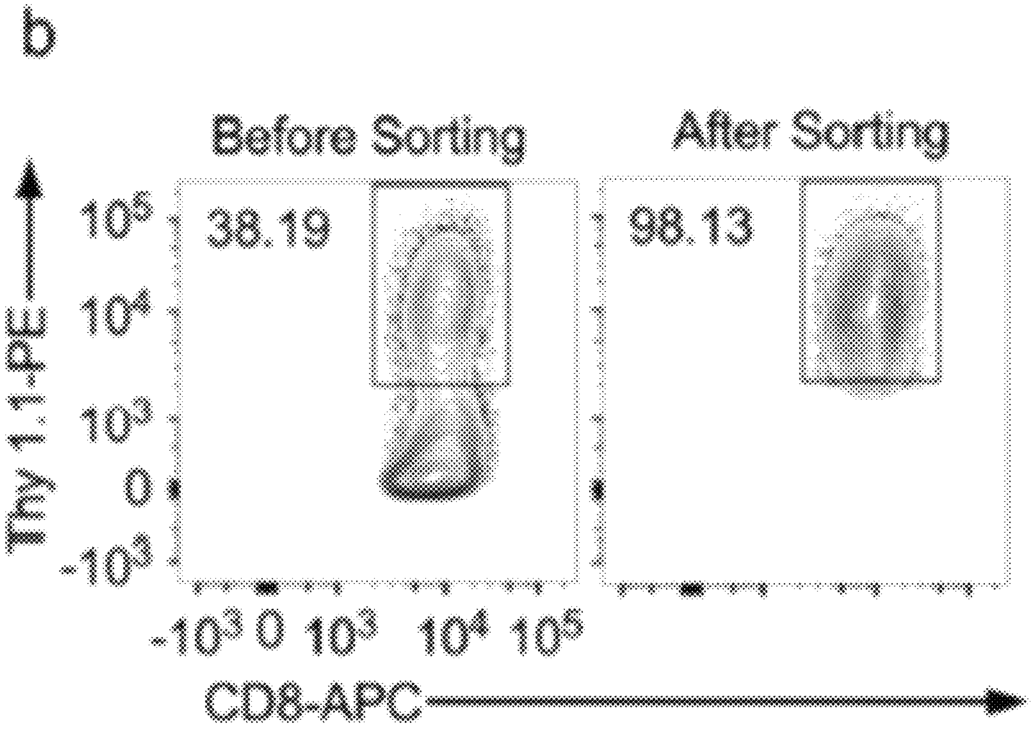
Figure 14C:

To evaluate the potential of SUSD2 as an immunotherapy target for cancer, the role of SUSD2 in regulating the antitumor efficacy of human CD19 (hCD19)-targeting CAR T cells was investigated. The mouse EL4 thymoma cell line was engineered to express hCD19 (FIG. 14A) and wild-type or Susd2$^{-/-}$ CD8$^+$ T cells were retrovirally transduced with a second-generation CAR containing a portion of hCD19 single chain variable fragment (ScFv) fused with the signaling domains from mouse CD28 and a mouse CD3 (sequence in which the first and third ITAMs had been inactivated. Sorted CAR T cells with a 98% live cell purity were transferred into Rag2$^{-/-}$ mice that have been inoculated with EL4-hCD19 tumor cells 7 days before CAR T cell transfer (FIG. 14B). While wild-type CAR T cells restrained tumor growth before day 13 post tumor cell inoculation, tumor growth rebounded at day 13, leading to similar survival in Rag2$^{-/-}$ mice with or without wild-type CAR T cell transfer (FIG. 7A). Transfer of Susd2$^{-/-}$ CAR T cells significantly reduced tumor growth at day 16 post tumor cell inoculation and translated in improved survival compared to wild-type CAR T cells (FIG. 7A). Enhanced production of IFN-γ, GzmB and TNF as well as improved cell survival in intratumoral Susd2$^{-/-}$ CAR T cells compared to wild-type CAR T cells (FIG. 7B-7C). Intratumoral Susd2$^{-/-}$ and wild-type CAR T cells had similar expression of PD-1 or LAG3 (FIG. 7D-7E). As such, deletion of SUSD2 in CAR T cells lead to an improved antitumor response in an EL4-hCD19 tumor model. Next, endogenous Susd2 was depleted in wild-type CAR T cells using Cas9 nucleoprotein (RNP) complex electroporation (FIG. 14C). Transfer of Susd2-depleted CAR T cells in Rag2$^{-/-}$ mice resulted in improved control of EL4-hCD19 tumors and increased survival compared to transfer of wild-type CAR T cells (FIG. 7F). Increased production of IFN-γ, GzmB, TNF and IL-2 (FIG. 7G) and increased percentages of TCF1$^+$PD-1$^+$CD8$^+$ T ExP cells and decreased percentages of TCF1-PD-1$^+$ Tim-3$^+$ CD8$^+$ TExT in Susd2-depleted CAR T cells compared to wild-type CAR T cells (FIG. 7H-7I), showing that therapeutic deletion of SUSD2 improved effector function of CAR T cells and counteracted the differentiation of terminally exhausted CAR T cells.

DISCUSSION

This example showed an inhibitory effect of SUSD2 on IL-2R signaling, consequently leading to an inhibition of the antitumor function of CD8$^+$ T cells. SUSD2 was found to interact with IL-2Rα via a sushi domain-dependent manner and interfered with IL-2-mediated effector functions of CD8$^+$ T cells. Deletion of SUSD2 in adoptively transferred TEFF cells and CAR T cells led to an improved antitumor efficacy, showing a targetable relevance of SUSD2 in immunotherapy for cancer. IL-2 was originally discovered as a T cell growth factor with a robust effect to promote the expansion of cytotoxic CD8$^+$ T cells. Clinical studies revealed promising results for IL-2 therapy in cancer patients. However, an intrinsic challenge of IL-2-based cancer immunotherapy is the activation of cytotoxic CD8$^+$ T cells in peripheral sites, which causes undesirable tissue damage. Among various immune cell types, SUSD2 was highly expressed in CD8$^+$ T cells and was further upregulated when CD8$^+$ T cells migrated from the secondary lymphoid organ into the TME. Therefore, based on the inhibitory effect of SUSD2 on IL-2R signaling, blockade of SUSD2 preferentially enhance the survival and function of antitumor CD8$^+$ T cells and avoid the activation of peripheral CD8$^+$ T cells. Meanwhile, since the current animal model employed a whole-body gene deletion strategy. Both experimental studies in tumor animal models and clinical cancer studies have characterized CD8$^+$ T cell exhaustion in the TME. CD8$^+$ TEFF cells with high expression of antitumor effectors, such as IFN-7 and granzymes, are critically required for the execution of the antitumor response. Intratumoral CD8$^+$ TExP cells can either differentiate into CX3CR1$^+$CD8$^+$ TEFF cells or TExT cells via distinct transcriptional, epigenetic and metabolic programs. IL-2R signaling potently activates the effector responses of CD8$^+$ T cells and IL-2 in combination with PD-L1 Ab therapy can rejuvenate TExT cells in a chronic virus infection model. Therefore, targeting IL-2R signaling, either alone or in combination with other ICB therapies, represents an approach to escalate the antitumor function of CD8$^+$ T cells, while minimizing T cell exhaustion. The scRNA-seq assay herein showed an increased percentage of CD8$^+$ TEFF cells and decreased percentage of TExT cells in tumor-bearing Susd2$^{-/-}$ mice, highlighting a therapy of SUSD2 to reverse T cell exhaustion.

Depletion of endogenous Susd2 gene in wild-type CAR T cells resulted in an improved control of tumor growth, increased effector function and decreased T cell death and terminal exhaustion. SUSD2 is also expressed in certain types of cancers. In summary, these results provide a mechanistic link between the SUSD2-modulated IL-2R signaling and the antitumor effector function of CD8$^+$ T cells and expand current understanding of molecular mechanisms driving immunosuppression in the TME. Considering the rapid advancements in the development of immunotherapy antibodies, blockade of SUSD2 by neutralizing antibody represents a therapeutic approach for cancer. Moreover, because SUSD2 modulates CD8$^+$ T cell effector function independently of PD-1, blockade of SUSD2 seems suitable for combinatorial therapy, especially for tumors resistant to PD-1 therapy.

Methods

Cell lines. Human 293T cell line (CRL-3216), B16-F10 cell line (murine melanoma, CRL-6475), EL4 cell line (murine thymoma, TIB39), EG7 cell line (murine thymoma expressing OVA, CRL-2113), Jurkat cell line (clone E6-1, TIB152) and Phoenix Eco Packaging cell line (CRL-3214) were purchased from the American Type Culture Collection (ATCC). B16-OVA cell line (SCC420) was purchased from Sigma-Aldrich. MC38 cell line (murine colon adenocarcinoma) was kindly provided by Dr. Yangxin Fu (UT Southwestern Medical Center. Platinum-E (Plat-E) Retroviral Packaging cell line (RV-101) was purchased from Cell Biolabs. 293T, MC38, and B16-OVA cells were cultured in Dulbecco's Modified Eagle Medium (DMEM; Gibco) supplemented with 10% fetal bovine serum (FBS; Sigma-Aldrich), 1% glutamine (Gibco), 1% sodium pyruvate, 1% non-essential amino acids (Gibco), 100 IU/ml penicillin and 100 mg/ml streptomycin (Gibco). EL4, EG7, B16-F10, and Jurkat cells were grown in RPMI-1640 (Gibco) supplemented with 10% FBS, 1% glutamine, 1% sodium pyruvate, 1% non-essential amino acids, 100 IU/ml penicillin, and 100 mg/ml streptomycin. All cell lines were maintained at 37° C., 5% $CO_2$. Buffy coats from healthy donors were purchased from the Gulf Coast Regional Blood Center and PBMCs were isolated by Ficoll-Paque (GE-Healthcare, 17-1440-03) density centrifugation.

Mice. Susd2$^{-/-}$ mice were generated by Cygan Biosciences with a CRISPR/Cas9-mediated genome engineering strategy (details of the gene targeting strategy in FIG. 8A) Exon 1 and 15 were selected as target sites. One pair of guide RNA (gRNA) targeting vector were constructed and generated by in vitro transcription. Cas9 mRNA and gRNA were co-injected into fertilized eggs (C57BL/6 background). The resultant pups were genotyped by PCR, followed by sequencing analysis. For genotyping, Susd2$^{-/-}$ mice, tail genomic DNA was isolated and then amplified by PCR using the following primers:

```
Primer 1:
                                    (SEQ ID NO: 3)
CAACACTTCTCCATCAGTAACCTGCACT;

Primer 2:
                                    (SEQ ID NO: 4)
ACTCTAAAGCTGGCTGGCTATTCATCA;

Primer 3:
                                    (SEQ ID NO: 5)
CTCACGGACAGTTATGGAACCGTG.
```

The PCR conditions was 95° C. 3 min; 95° C. 30 s; 60° C. 60 s, 72° C. 60 s, repeated for 35 cycles. C %&BL/6J mice (000664), Thy1.1 mice (000406), Rag2$^{-/-}$ mice (008449) and OT-I mice (003831) were obtained from the Jackson Laboratory. OT-II mice have been previously described. Susd2$^{-/-}$ OT-I and Susd2$^{-/-}$ OT-II mice were generated by crossing Susd2$^{-/-}$ with OT-I and OT-II mice, respectively. All mice were housed in the specific pathogen-free facility and all in vivo experiments were performed in according with the guidelines established by The Ohio State University and National Institute of Health Guide for the Care and Use of Laboratory Animals and the Institutional Animal Care and Use Committee (IACUC).

Tumor cell inoculation. Eight to ten-week-old male mice were inoculated subcutaneously with $1\times10^6$ MC38, EG7, or B16-OVA cells in the right flank. For adoptive T cell transfer experiments, $1\times10^6$ EG7 cells were inoculated subcutaneously into the right flank of Thy1.1 mice (day 0). On day 7 after inoculation, mice were adoptively transferred with $4\times10^6$ WT or Susd2$^{-/-}$ OT-I cells via tail vein. For CAR T transfer experiments, $1\times10^6$ EL4-hCD19 cells were inoculated subcutaneously into the right flank of Rag2$^{-/-}$ mice (day 0). On day 7 after inoculation, mice were injected with $5\times10^6$ WT or Susd2$^{-/-}$ CAR T cells. For CD8$^+$ T cells depletion experiments, WT or Susd2$^{-/-}$ mice were treated with 200 μg of control IgG (clone LTF-2, Bio X cell) or anti-CD8a depleting antibody (clone 2.43, Bio X cell) at day 0, 7, and 14 after tumor cell inoculation. For PD-L1 blockade experiments, WT or Susd2$^{-/-}$ mice were intraperitoneally injected with 250 μg of control IgG and anti-PD-L1 antibody (clone 10F.9G2, Bio X Cell) at day 7, 10, and 13 after tumor cell inoculation. Digital caliper was used to measure tumor volume at least three times a week and tumor volume were calculated using the formula $mm^3$=(Length× width×width/2). Mice were sacrificed when tumors reached a size of 2000 $mm^3$.

Flow cytometry. Tumors were minced into small fragments and digested with 1 mg/mL collagenase IV and 50 U/mL DNase I for 30 min at 37° C. Samples were mechanically disaggregated and filtered with 70-μm cell strainers. Single cell suspensions were treated with purified CD16/32 Ab (clone 93; BioLegend), and then stained with fluorochrome-conjugated Abs, including CD11b, F4/80, CD11c, Ly6C, Ly6G, CD3, CD4, CD8, CD8, CD25, Thy-1.1, Thy1.2, NK1.1, CD19, PD-1 and LAG3. For intracellular staining of p-STAT5, cells were fixed with 2% paraformaldehyde for 10 min at room temperature and then incubated in pre-chilled methanol for 20 min at 4° C. for permeabilization. Cells were washed 3 times with PBS containing 2% FBS and 1 mM EDTA and then stained with p-STAT5 Ab. For intracellular cytokine staining of tumor-infiltrating lymphocytes, cells were stimulated in vitro with PMA (50 ng/ml, Sigma-Aldrich) and ionomycin (500 ng/ml, Sigma-Aldrich) in the presence of GolgiPlug and GolgiStop (BD Biosciences) for 4 h, and then surface stained as aforementioned. Cells were then fixed and permeabilized using BD Cytofix/Cytoperm (BD Biosciences) and stained with IFN-γ, GzmB, TNF and IL-2 Abs. For intranuclear Foxp3 or TCF-1 staining, single-cell suspensions were stained with Abs against cell-surface antigens as aforementioned, fixed and permeabilized using Foxp3 Fix/Perm Buffer Kit (BioLegend), followed by staining with Foxp3 Ab or TCF-1 Ab. For cell apoptosis analysis, cells were resuspended in the annexin-V Binding Buffer and then stained with annexin-V and 7-AAD viability solution (BioLegend) for 15 min at 25° C.

To characterize CD8$^+$ cells in the TME, multi-dimensional flow cytometry assay with a panel of 32 lineage- and T-cell state specific markers (CD45, CD3, CD8, CD4, CD11b, NK1.1, Foxp3, Tim-3, PD-1, CD25, CD62L, CD69, CD44, Lag3, Vista, TIGIT, CD27, CD38, CD39, KLRG1, ICOS. CD95, CD103, CXCR3, TOX, TCF-1, Ki67, EOMES, IFN-γ, TNF, GzmB) was performed. Data were acquired in a 5-Laser Cytek Aurora System. Analysis was performed using OMIQ data analysis software (www.omiq.ai) (Omiq). Uniform Manifold Approximation and Projection (UMAP) algorithm was applied for dimension reduction and visualization of the data after concatenating all samples. Cells were then clustered based on their marker expression using the FlowSOM package. Heatmaps of median marker expression were generated to further understand the features of each cluster. Differences in the abundance of the clusters between the two groups were determined with EdgeR.

Cell sorting. CD4$^+$, CD8$^+$, CD11b$^+$ and CD19$^+$ cells were sorted from mouse splenocytes. Human CD4$^+$, CD8$^+$, CD14$^+$ and CD19$^+$ cells were sorted from PBMCs. Mouse Treg cells were isolated using the Mouse CD4$^+$CD25$^+$ Regulatory T Cell Isolation Kit (130-091-041; Miltenyi). Human Treg cells were isolated from PBMCs by EasySep Human CD4$^+$CD127$^{low}$CD25$^+$ Regulatory T Cell Isolation Kit (18063; STEMCELL Technologies). Cells were sorted using a 100-μm chip on a MA900 Multi-Application Cell Sorter (SONY) in PBS with 2% FBS.

scRNA-seq. Mice bearing MC38 tumor cells were sacrificed at day 18 after tumor cell inoculation. Tumors were minced into small fragments and digested with 1 mg/ml collagenase IV and 50 U/ml DNase I for 30 minutes at 37° C. Single cell suspensions were stained with 7-AAD and anti0CD45 antibody (Clone 30-F11; BioLegend) and sorted (BD FACSAria Fusion Cell Sorter). Live CD45$^+$ cells were processed using the inDrops V3 scRNA-seq platform, as previously described. inDrops libraries were sequenced on the NextSeq Illumina platform, paired-end mode. The raw sequencing files (four WT and four KO in the FASTQ format) were aligned against the pre-built 10× mouse reference genome (mm10) using the CellRanger (v3.0.2) pipeline. For each dataset, a cell was removed if it has (i) less than 200 exposed genes, (ii) fewer than 200 or higher than 4,000 total features, and (iii) mitochondria content higher than 90%. A gene was removed if it was expressed in less than four cells. The integrative analysis was then performed using the Seurat (v3.0) pipeline. Specifically, the first 20 dimensions of the canonical correlation analysis and the top 2,000 highly variable genes were used. Cell clusters were identified using the integrated data with the top five principal components (PCs) and a resolution of 0.5 in the Louvain clustering. All cell clusters were manually annotated according to the expression of curated marker genes. Differentially expressed (DE) genes were identified in each cell cluster using the Wilcoxon rank test, and the default log FC (0.25) threshold was used for filtering. Those cells were further subset with Cd8a, Trbc1, and Trbc2 expression from the integrated data. The selected data was rescaled and re-clustered with the top 10 PCs and a resolution of 0.2 in the Louvain clustering. DE genes in the subset data were identified in the same way as described above. Gene Ontology (GO) enrichment was performed via the EnrichR package (v1.0) to compare the enrichment differences between WT and KO in $CD8^+$ T cell subpopulations. GO terms with BH-adjusted p-values less than 0.05 were considered as significantly enriched.

Bulk RNA-seq. $CD8^+$ T cells were isolated by the EasySep Mouse $CD8^+$ T Cell Isolation Kit (STEMCELL Technologies) from total splenocytes of either WT or $Susd2^{-/-}$ OT-I mice left untreated or stimulated with OVA257-264 for 3 days. RNA was extracted using TRIzol Reagent (Invitrogen) and were further quantified using Qubit Fluorometer, and those with RIN values>7 were used for RNA isolation using NEBNext Poly mRNA Magnetic Isolation Module (#E7490L, New England Biolabs, NY). Subsequently, purified mRNAs were fragmented for 10 minutes. cDNAs were synthesized and amplified for 12 PCR cycles using NEBNext$^+$ Ultra™ II Directional (stranded) RNA Library Prep Kit for Illumina (E7760L; NEB) with NEBNext Multiplex Oligos Index kit (6442L; NEB). Distributions of the template length and adapter-dimer contamination were assessed using an Agilent 2100 Bioanalyzer and High Sensitivity DNA kit (Agilent Technologies). The concentration of cDNA libraries was determined using Invitrogen Qubit dsDNA HS reagents and read on a Qubit Fluorometer (Thermo Fisher Scientific), and cDNA libraries were paired end 150 bp format sequenced on a NovaSeq 6,000 SP system (Illumina). Bulk RNA-seq profiling was performed on eight samples (four WT and four KO). Quality control and data trimming of the raw sequences were performed via fastp (v0.23.2), and reads alignment was performed using HISAT2 (v2.1.0) to map sequence to the mouse reference (*Mus_musculus*. GRCm38.99). Samtools (v1.10) was used to convert and sort bam files, and subread (v2.0.1) was used to quantify reads to generate gene expression count matrix. DEG analysis was performed using DESeq2 (v1.32.0). Genes with log-fold change greater than 1.5 and p-value less than 0.05 were considered as DEGs in each comparison.

Plasmids and molecular cloning. Commercially available expression plasmids included human SUSD2 (OHu27875) from Genescript, mouse Susd2 (MmCD00315635) from the Dana-Farber/Harvard Cancer Center (DF/HCC) DNA Resource Core, IL2RA-eGFP (#86055) from Addgene and pCMV3-SP-N-Flag-mIL2ra (MG50292-NF) from Sino Biological. To generate the retrovirus vector expressing human SUSD2 and Susd2 cDNA were subcloned into the pLVX-mCherry-N1 (Clontech #632562) or pMSCV-IRES-GFP II (pMIG II, Addgene #52107) with V5 and His tag. To generate Flag-IL2RA, human IL2RA cDNA were subcloned into p3×Flag-CMV-7.1 vector. All primers used for cloning are listed in Table 1. To generate IL2RA Δ22-84 aa or A123-186 aa mutant, Phusion Site-Directed mutagenesis Kit was used according to the manufacturer's instructions (Thermo Fisher Scientific). Primers for mutagenesis PCR are listed in Table 2. All cloned genes were checked by sequencing.

Retroviral transduction of T cells. For retrovirus generation, Plat-E cells were seeded into 10-cm dishes overnight at a concentration of $5\times10^6$ cells/dish. On the following day, plasmid encoding pMIG II empty vector, pMIG II-Susd2, or pMIG II-Susd2 ASushi and packaging plasmid pCL-Eco (Addgene plasmid #12371) were mixed along with polyethylenimine (PEI) at a 3:1=PEI:DNA ratio and added into the Plat-E cells overnight. Medium was then changed, and viral supernatant was collected twice in the following 72 hour. Retroviral supernatants were concentrated by PEG 8000 and immediately stored at −80° C. For retroviral transduction, OT-I T cells ($4\times10^6$ cells/well) or Jurkat cells ($1\times10^6$ cells/well) were plated in 6-well plates, stimulated with 1 μg/ml $OVA_{257-264}$ (Genscript) for 24 hours. Viral supernatant (1:1 vol/vol ratio) and 8 μg/ml polybrene (Sigma-Aldrich) were added. Spinfection was performed at 32° C. for 2 hours at 800 g. Media was changed after 2 hours. Transduced OT-I T cells were cultured for another 48 hours with $OVA_{257-264}$ and tested in functional assays.

Antigen-presenting assay. BMDCs were prepared by flushing bone marrow from mouse hindlimbs and plating $1\times10^6$ cell/ml in RPMI-1640 media and 10% FBS and 20 ng/ml mGM-CSF. Medium were changed at day 4. On day 6, BMDCs were harvested and loaded with 1 μg/ml $OVA_{257-267}$ (Genscript) at 37° C. for 2 hours. BMDCs were then washed three times with PBS to remove excessive peptide followed by resuspension in RPMI-160 medium with 10% FBS. OT-I T cells were harvested from spleens of WT or $Susd2^{-/-}$ mice by $CD8^+$ T Cell Enrichment Kit (Miltenyi) and then co-cultured with peptide-pulsed WT or $Susd2^{-/-}$ BMDCs at a 5:1 ratio in 96-well plates. In indicated experiments, anti-IL-2 (Clone JES6-1A12), anti-IL-2Rα (Clone PC61) or anti-IL-2Rβ (Clone™-β1) blocking antibody were added to the cocultures at a concentration of μg/ml.

FACS-based in vitro killing assay. MC38, EG7 and B16-OVA cells were labeled with CFSE (C34554; Thermo Fisher Scientific), MC38 cells were pulsed with OVA257-264 peptides at 1 μg/ml for 1 h and used as target cells. In vitro activated WT or $Susd2^{-/-}$ OT-I cells were collected and incubated with peptide-pulsed MC38, EG7 and B16-OVA cells at different ratios for 4 h. The percentage of dead cells were measured with 7-AAD staining.

In vitro Treg cell suppression assay. A total of $1\times10^5$ CFSE-labeled naïve T ($CD4^+CD25^-$) cells were stimulated with 1 μg/ml anti-CD3 Ab and 1 μg/ml anti-CD28 Ab. Tregs from WT and $Susd2^{-/-}$ mice were isolated with the Mouse $CD4^+CD25^+$ Regulatory T Cell Isolation Kit (130-091-041, Miltenyi), and added to the culture to achieve Treg/$CD4^+$ T cell ratios of 0.0625:1 to 1:1. $CD4^+$ T cells only, without Tregs, were used as a positive control for T cell proliferation. Three days after stimulation, CFSE dilution of $CD4^+$ T cells were analyzed by FACS assay.

In vitro Treg cell suppression assay. A total of $1\times10^5$ carboxyfluorescein diacetate succinimidyl ester (CFSE)-labeled naïve T ($CD4^+CD25^-$) cells were stimulated with 1 μg/ml anti-CD3 Ab and 1 μg/ml anti-CD28 Ab. Tregs from WT and $Susd2^{-/-}$ mice were isolated with Mouse $CD4^+$ CD25⁻Regulatory Cell Isolation Kit (Miltenyi), and added to the culture to achieve Treg/$CD4^+$ T cell ratios of 0.0625:1 to 1:1. $CD4^+$ T cells only, without Tregs, were used as a positive control for T cell proliferation. Three days after stimulation, CFSE dilutions of $CD4^+$ T cells were analyzed and quantified by FACS analysis.

IL-2 binding assay. $1\times10^6$ WT or Susd2$^{-/-}$ OT-I cells were incubated with 5 ng biotinylated IL-2 (ACRO Biosystems) in 100 μl PBS, 0.1% BSA for 20 minutes at 4° C. Cells were washed three times with PBS and stained with streptavidin-PE (BioLegend) for 30 minutes at 4° C. Parallel aliquots of cells were pre-incubated with unlabeled IL-2 (500 ng/ml, Perprotech). FACS analysis was carried out on BD FACSCanto™ II Flow Cytometry (BD Biosciences).

RT-PCR. Total RNA was extracted from primary or in vitro cultured cells using Trizol reagent (Invitrogen). cDNA was synthesized with Moloney murine leukemia virus reverse transcriptase (Invitrogen) at 38° C. for 60 minutes. RT-PCR was performed using iTaq Universal SYBR Green Supermix (Bio-Rad) in CFX Connect Real-Time PCR Detection System (Bio-Rad). The fold difference in mRNA expression between treatment groups was determined by AACt method. β-actin was used as an internal control. The primer pair sequences of individual genes are listed in the Table 3.

Immunoprecipitation and immunoblotting. For immunoprecipitation, cells were lysed in RIPA buffer supplemented with cOmplete™ Protease Inhibitor Cocktail (Sigma-Aldrich). Total protein extracts were incubated with goat anti-V5 agarose (S190-119, Bethyl Laboratories) or anti-Flag M2 Affinity Gel (A2220, Sigma-Aldrich) overnight at 4° C. under gentle agitation. Samples were washed 5 times with cold RIPA buffer. To elute proteins from the beads, samples were incubated with 30 μl of SDS sample buffer at 95° C. for 10 minutes. Protein content in the supernatant was analyzed by immunoblotting. For immunoblotting, electrophoresis of protein was performed by using the NuPAGE system (Invitrogen) according to the manufacturer's protocol. Briefly, cultured $CD8^+$ T cells or Jurkat cells were collected and lysed with RIPA buffer. Proteins were separated on a NuPAGE precast gel and were transferred onto nitrocellulose membranes (Bio-Rad). Appropriate primary antibodies and HRP-conjugated secondary antibodies were used and proteins were detected using the Enhanced Chemiluminescent (ECL) reagent (Thermo Fisher Scientific). The images were acquired with ChemiDoc MP System (Bio-Rad). Primary antibodies for immunoblotting included anti-SUSD2 (HPA004117), anti-FLAG M2-HRP (A8592), and anti-Stat5 (9363) from Cell Signal Technology; anti-mouse IL-2Rα (AF2438-SP) from R&D; anti-human IL-2Rα (sc-365511), anti-IL-2RO (sc-393093) from Santa Cruz Biotechnology; anti-V5-HRP (A00877) from Genscript; anti-γ chain (ab273023) from Abcam.

Confocal microscopy. 293T cells were transfected with plasmids expressing empty vector, GFP-IL2RA or pLVX-mCherry-N1-SUSD2. After 36 hours, cells were digested and fixed with 4% paraformaldehyde. Nuclear counterstaining was performed with DAPI (H-1200; Vector Laboratories). Then, cells were transferred into 35-mm glass bottom dishes (Mat-Tek) for image capture using a laser scanning confocal fluorescence microscope with a 60× objective (Olympus FLUOVIEW; FV3000).

Mass spectrometry assay of SUSD2 interactome. High resolution/accurate mass (HR/AM)-based quantitative proteomics strategy was employed to identify protein-protein interactions. Briefly, immunoprecipitated (anti-V5) Susd2 complex from retrovirus-infected Susd2$^{-/-}$ OT-I T cells was washed 5 times with RIPA buffer and boiled with SDS buffer followed by Suspension Trapping based on-filter digestion. Three biological replicates of the pulldown experiment were included. The digests were desalted using C18 StageTips, dried in a SpeedVac and the resuspended in 20 ul LC buffer A (0.1% formic acid in water) for LC-MS/MS analysis. The analysis was performed using an Orbitrap Eclipse MS (Thermo Fisher Scientific) coupled with an Ultimate 3000 nanoLC system and a nanospray Flex ion source (Thermo Fisher Scientific). Peptides were first loaded onto a trap column (PepMap C18; 2 cm×100 μm I.D.) and then separated by an analytical column (PepMap C18, 3.0 μm; 20 cm×75 mm I.D.) using a binary buffer system (buffer A, 0.1% formic acid in water; buffer B, 0.1% formic acid in acetonitrile) with a 165-min gradient (1% to 25% buffer B over 115 minutes; 25% to 80% buffer B over 10 minutes; back to 2% B in 5 minutes for equilibration after staying on 80% for 15 minutes). MS data were acquired in a data-dependent top-12 method with a maximum injection time of 20 ms, a scan range of 350 to 1,800 Da, and an automatic gain control target of 1e6. MS/MS was performed via higher energy collisional dissociation fragmentation with a target value of 5e5 and maximum injection time of 100 ms. Full MS and MS/MS scans were acquired by Orbitrap at resolutions of 60,000 and 17,500, respectively. Dynamic exclusion was set to 20 seconds. Protein identification and quantification were performed using the MaxQuant-Andromeda software suite (version 1.6.3.4) with most of the default parameters. An UniProt mouse database (17,089 sequences) was used for the protein identification. Other parameters include trypsin as an enzyme with maximally two missed cleavage sites; protein N-terminal acetylation and methionine oxidation as variable modifications; cysteine carbamidomethylation as a fixed modification; peptide length must be at least 7 amino acids. False discovery rate was set at 1% for both proteins and peptides.

CAR T cell transfer. The EL4-hCD19 cell lines were constructed by transfecting the EL4 cell line with a MMLV retrovector carrying hCD19 with the deletion of its intracellular domain. The plasmid was packaged in Phoenix Eco cell lines and the viral supernatant was harvested 48 hours after transfection. After viral transduction, EL4-hCD were sorted to achieve the positive clone>95%. To generate hCD19-targeting CAR T cells, the CAR construct was pieced together using portions of hCD19 single chain variable fragment (ScFv), and portions of the murine CD28 and CD3 sequences (with first and third ITAMs of the CD3 molecule inactivated) and cloned into a MSGV retrovector. The retroviral vector was transfected to Phoenics Eco cell lines to generate viral supernatant. The harvest, stimulation and transfection of T cells were conducted. In brief, splenocytes from WT and Susd2$^{-/-}$ mice were subjected to T cell isolation (EasySep Mouse T Cell Isolation Kit, STEMCELL Technologies) then stimulated at 37° C. for 24 hours. On the following day, viral supernatant was spun at 2000 g, 32° C., for 2 hours on RetroNectin (TAKARA Bio)-coated plate. Activated T cells were loaded to the plate and expanded for 2-3 days.

Statistics analysis. Statistical analyses were performed with GraphPad Prism 8 (GraphPad Software). Unless specified, Student's t test was used for comparisons of two groups, One-way ANOVA or Two-way ANOVA for comparison of multiple groups with posthoc Tukey's test for multiple comparisons. Significance of in vivo experiments was calculated by log-rank (Mantel-Cox) test for Kaplan-Meier survival analysis or Two-way ANOVA with posthoc Tukey's test for multiple comparisons. Differences between groups are shown as the mean±SEM. P values of less than 0.05 were considered statistically significant $p<0.05$=*; $p<0.01$=; $p<0.001$=*; $p<0.0001$=****.

Example 3. Therapeutics and SUSD2 Inhibition

Based on the inhibitory effect of SUSD2 on antitumor effector function of $CD8^+$ T cells, the therapeutic use of a SUSD2 blockade is applied, via either genetic knockdown strategy or neutralizing antibody, in tumor immunotherapy. Three major usages are described below:

1. Inhibition of SUSD2 to maximize the antitumor efficacy of adoptive T cell transfer (ACT) therapy. ACT therapy has been documented to ACT is a process of transferring pre-activated antigen-specific T cells for the treatment of established cancers. To maximize antitumor efficacy of ACT therapy, gene-deletion of SUSD2 was conducted in in vitro activated antigen-specific T cells before cell transfer via a CRISPR-Cas9 based genomic engineering strategy.
2. Inhibition of SUSD2 to maximize the antitumor efficacy of CAR T cell transfer therapy. CAR T cell therapy is a revolutionizing antitumor immunotherapy that takes advantage of genetically engineered T cell with chimeric antigen receptor. To generate hCD19-targeting CAR T cells, the CAR construct was pieced together using portions of hCD19 single chain variable fragment (ScFv), and portions of the human CD28 and CD3 (sequences, and cloned into a MSGV retrovector. To maximize antitumor efficacy of CAR T cell therapy, gene-deletion of SUSD2 was performed in in vitro generated CAR T cells before cell transfer.
3. SUSD2 blockade in combination with anti-PD-L1 therapy. These results indicate that deletion of Susd2 in mice results in an increased antitumor effect of anti-PD-L1 therapy, highlighting that SUSD2 blockade can have a synergistic effect with anti-PD-L1 treatment.

Unless defined otherwise, all technical and scientific terms used herein have the same meanings as commonly understood by one of skill in the art to which the disclosure belongs. Publications cited herein and the materials for which they are cited are specifically incorporated by reference.

Those skilled in the art will appreciate that numerous changes and modifications can be made to the preferred embodiments of the disclosure and that such changes and modifications can be made without departing from the spirit of the disclosed. It is, therefore, intended that the appended claims cover all such equivalent variations as fall within the true spirit and scope of the disclosure.

TABLE 1

Primer sequences for RT-PCR (related to FIGS. 4-6).

| Genes | Forward | Reverse |
|---|---|---|
| Mouse Il6 | AGCTGGAGTCACAGAAGGAG (SEQ ID NO: 6) | AGGCATAACGCACTAGGTTT (SEQ ID NO: 7) |
| Mouse Tnfa | GTCAGGTTGCCTCTGTCTCA (SEQ ID NO: 8) | TCAGGGAAGAGTCTGGAAAG (SEQ ID NO: 9) |
| Mouse Actb | AGGGCTATGCTCTCCCTCAC (SEQ ID NO: 10) | CTCTCAGCTGTGGTGGTGAA (SEQ ID NO: 11) |
| Human IFNB1 | CATTACCTGAAGGCCAAGGA (SEQ ID NO: 12) | CAATTGTCCAGTCCCAGAGG (SEQ ID NO: 13) |
| Human IL6 | CGGGAACGAAAGAGAAGCTCTA (SEQ ID NO: 14) | GGCGCTTGTGGAGAAGGAG (SEQ ID NO: 15) |
| Human TNFA | GAGGCCAAGCCCTGGTATG (SEQ ID NO: 16) | CGGGCCGATTGATCTCAGC (SEQ ID NO: 17) |
| Human GADPH | ATGACATCAAGAAGGTGGTG (SEQ ID NO: 18) | CATACCAGGAAATGAGCTTG (SEQ ID NO: 19) |

TABLE 2

| Primer sequences for molecular cloning (related to FIG. 4). p3xFLAG-CMV-7.1-RUBCN WT |
|---|
| Forward GCGAATTCAATGCGGCCGGAGGGCGCGGG (SEQ ID NO: 20) |
| Reverse GCGGATCC TCAGGTGGCCTCCAGGACGG (SEQ ID NO: 21) |

| Primer sequences for site-directed mutagenesis (related to FIG. 3). |
|---|
| RUBCN (K426R) Forward CTCCAGAATCCTGCAATGATAGGGCGAAGTTGAGAGGCCCTTTG (SEQ ID NO: 22) |
| Reverse CAAAGGGCCTCTCAACTTCGCCCTATCATTGCAGGATTCTGGAG (SEQ ID NO: 23) |
| RUBCN (K549R) Forward GCGCCAGCAAATCCGCACCAGGAACCTGCTCCCCATGTACCAG (SEQ ID NO: 24) |
| Reverse CTGGTACATGGGGAGCAGGTTCCTGGTGCGGATTTGCTGGCGC (SEQ ID NO: 25) |

-continued

| Primer sequences for site-directed mutagenesis (related to FIG. 3). |
|---|
| RUBCN (K682R) Forward GCAGCACGCTGACATCTACAGGCTGCGGATTCGTGTTCGTG (SEQ ID NO: 26) |
| Reverse CACGAACACGAATCCGCAGCCTGTAGATGTCAGCGTGCTGC (SEQ ID NO: 27) |
| RUBCN (K734R) Forward GACTGACCCTGATTACATCAGGCGACTGCGGTACTGTGAGTAC (SEQ ID NO: 28) |
| Reverse GTACTCACAGTACCGCAGTCGCCTGATGTAATCAGGGTCAGTC (SEQ ID NO: 29) |
| RUBCN (K765R) Forward CCCCAGCCGGGTTCTGCGCAgGTGGGACTTCAGCAAGTACTAC (SEQ ID NO: 30) |
| Reverse GTAGTACTTGCTGAAGTCCCACCTGCGCAGAACCCGGCTGGGG (SEQ ID NO: 31) |
| RUBCN (K860R) Forward GAATGACCTGACTGCGACCAGGAgGGGGGAGCTGGGGCCCCGGC (SEQ ID NO: 32) |
| Reverse GCCGGGGCCCCAGCTCCCCCCTCCTGGTCGCAGTCAGGTCATTC (SEQ ID NO: 33) |

SEQUENCES

1. SEQ ID NO: 1 - Mouse Susd2 (NP_082166.3)
MKLALLPWILMLLSTIPGPGFTAGAQGSCSLRCGAQDGLCSCHPTCSGLGTCCEDFLDY
CLEILPSSGSMMGGKDFVVQHLKWTDPTDGVICRFKESIQTLGYVDDFYQVHCISPLLYE
SGYIPFTISMDNGRSFPHAGTWLAAHPYKVSESEKSQLVNETHWQYYGTSDTRGNLNLT
WDTSALPTPAVTIELWGYEETGKPYSGNWTSKWSYLYPLATNIPNTGFFTFTPKPASPQ
YQRWKVGALRISSSRNYPGEKDVRALWTNDHALAWHLGDDFRADSVAWARAQCLAW
EALEDQLPNFLTELPDCPCTLAQARADSGRFFTDYGCDIEHGSVCTYHPGAVHCVRSVQ
ASPRYGSGQQCCYTAAGTQLLTSDSTSGSTPDRGHDWGAPPYRTPPRVPGMSHWLYDV
ISFYYCCLWAPECPRYMKRRPSSDCRNYRPPRLASAFGDPHFVTFDGTSFSFSGNGEYVL
LETTLSDLRVQGRAQPGRMPNGTQARGTGLTAVAVQEDNSDVIEVRLAGGSRVLEVLL
NQKVLSFTEQNWMDLKGMFLSVAAQDKVSIMLSSGAGLEVGVQGPFLSVSILLPEKFLT
HTRGLLGTLNNNPRDDFTLRNGQVLPLNASAQQVFQFGADWAVSNTSSLFTYDSWLLV
YQFVYGPKHNPNFKPLFPDETTLSPSQTEDVARLCEGDRFCILDVMSTGSSSVGNATRIA
HQLHQHRLKSLQPVVSCGWLPPPANGHKEGLRYLEGSVVRESCNNGYSLVGPESSTCQ
ADGKWSMPTPECQPGRSYTVLLSIIFGGLAIVALISIIYMMLHRRRKSNMTMWSSQP 2 SEQ ID NO: 2 - Human Susd2 (NP_062547)
MKPALLPWALLLLATALGPGPGPTADAQESCSMRCGALDGPCSCHPTCSGLGTCCLDF
RDFCLEILPYSGSMMGGKDFVVRHFKMSSPTDASVICRFKDSIQTLGHVDSSGQVHCVS
PLLYESGRIPFTVSLDNGHSFPRAGTWLAVHPNKVSMMEKSELVNETRWQYYGTANTS
GNLSLTWHVKSLPTQTITIELWGYEETGMPYSQEWTAKWSYLYPLATHIPNSGSFTFTPK
PAPPSYQRWRVGALRIIDSKNYAGQKDVQALWTNDHALAWHLSDDFREDPVAWARTQ
CQAWEELEDQLPNFLEELPDCPCTLTQARADSGRFFTDYGCDMEQGSVCTYHPGAVHC
VRSVQASLRYGSGQQCCYTADGTQLLTADSSGGSTPDRGHDWGAPPFRTPPRVPSMSH
WLYDVLSFYYCCLWAPDCPRYMQRRPSNDCRNYRPPRLASAFGDPHFVTFDGTNFTFN
GRGEYVLLEAALTDLRVQARAQPGTMSNGTETRGTGLTAVAVQEGNSDVVEVRLANR
TGGLEVLLNQEVLSFTEQSWMDLKGMFLSVAAGDRVSIMLASGAGLEVSVQGPFLSVS
VLLPEKFLTHTHGLLGTLNNDPTDDFTLHSGRVLPPGTSPQELFLFGANWTVHNASSLLT
YDSWFLVHNFLYQPKHDPTFEPLFPSETTLNPSLAQEAAKLCGDDHFCNFDVAATGSLS
TGTATRVAHQLHQRRMQSLQPVVSCGWLAPPPNGQKEGNRYLAGSTIYFHCDNGYSLA
GAETSTCQADGTWSSPTPKCQPGRSYAVLLGIIFGGLAVVAAVALVYVLLRRRKGNTH
VWGAQP -continued

| SEQUENCES |
|---|

3. SEQ ID NO: 3
CAACACTTCTCCATCAGTAACCTGCACT

4. SEQ ID NO: 4
ACTCTAAAGCTGGCTGGCTATTCATCA

5. SEQ ID NO: 5
CTCACGGACAGTTATGGAACCGTG

6. SEQ ID NO: 6
AGCTGGAGTCACAGAAGGAG

7. SEQ ID NO: 7
AGGCATAACGCACTAGGTTT

8. SEQ ID NO: 8
GTCAGGTTGCCTCTGTCTCA

9. SEQ ID NO: 9
TCAGGGAAGAGTCTGGAAAG

10. SEQ ID NO: 10
AGGGCTATGCTCTCCCTCAC

11. SEQ ID NO: 11
CTCTCAGCTGTGGTGGTGAA

12. SEQ ID NO: 12
CATTACCTGAAGGCCAAGGA

13. SEQ ID NO: 13
CAATTGTCCAGTCCCAGAGG

14. SEQ ID NO: 14
CGGGAACGAAAGAGAAGCTCTA

15. SEQ ID NO: 15
GGCGCTTGTGGAGAAGGAG

16. SEQ ID NO: 16
GAGGCCAAGCCCTGGTATG

17. SEQ ID NO: 17
CGGGCCGATTGATCTCAGC

18. SEQ ID NO: 18
ATGACATCAAGAAGGTGGTG

19. SEQ ID NO: 19
CATACCAGGAAATGAGCTTG

20. SEQ ID NO: 20
GCGAATTCAATGCGGCCGGAGGGCGCGGG

21. SEQ ID NO: 21
GCGGATCCTCAGGTGGCCTCCAGGACGG

22. SEQ ID NO: 22
CTCCAGAATCCTGCAATGATAGGGCGAAGTTGAGAGGCCCTTTG

23. SEQ ID NO: 23
CAAAGGGCCTCTCAACTTCGCCCTATCATTGCAGGATTCTGGAG

24. SEQ ID NO: 24
GCGCCAGCAAATCCGCACCAGGAACCTGCTCCCCATGTACCAG

25. SEQ ID NO: 25
CTGGTACATGGGGAGCAGGTTCCTGGTGCGGATTTGCTGGCGC

26. SEQ ID NO: 26
GCAGCACGCTGACATCTACAGGCTGCGGATTCGTGTTCGTG

27. SEQ ID NO: 27
CACGAACACGAATCCGCAGCCTGTAGATGTCAGCGTGCTGC

-continued

| SEQUENCES |
|---|
| 28. SEQ ID NO: 28<br>GACTGACCCTGATTACATCAGGCGACTGCGGTACTGTGAGTAC |
| 29. SEQ ID NO: 29<br>GTACTCACAGTACCGCAGTCGCCTGATGTAATCAGGGTCAGTC |
| 30. SEQ ID NO: 30<br>CCCCAGCCGGGTTCTGCGCAgGTGGGACTTCAGCAAGTACTAC |
| 31. SEQ ID NO: 31<br>GTAGTACTTGCTGAAGTCCCACCTGCGCAGAACCCGGCTGGGG |
| 32. SEQ ID NO: 32<br>GAATGACCTGACTGCGACCAGGAgGGGGGAGCTGGGGCCCCGGC |
| 33. SEQ ID NO: 33<br>GCCGGGGCCCCAGCTCCCCCCTCCTGGTCGCAGTCAGGTCATTC |
| 34. SEQ ID NO: 34<br>CAATGGGAGCAATAGCAGAGCTCGTTTAGTGACCGTCAGAATTAACCATGGA<br>CTACAAAGACCATGA**CGGTGATTATAAAGATCATGACATCGATTACAAGGA**<br>**TGACGATGACAAGCTTGCGGCCGCGAATTCAATG**GATTCATACCTGCTGAT<br>GTGGGGACTGCTCACGTTCATCATGGTGCCTGGCTGCCAGGCAGAGCTCTGTG<br>ACGATGACCCGCCAGAGATCCCACACGCCACATTCAAAGCCATGGCCTACAA<br>GGAAGGAACCATGTTGAACTGTGAATGCAAGAGAGGTTTCCGCAGAATAAAA<br>AGCGGGTCACTCTATATGCTCTGTACAGGAAACTCTAGCCACTCGTCCTGGGA<br>CAACCAATGTCAATGCACAAGCTCTGCCACTCGGAACACAACGAAACAAGTG<br>ACACCTCAACCTGAAGAACAGAAAGAAAGGAAAACCACAGAAATGCAAAGT<br>CCAATGCAGCCAGTGGACCAAGCGAGCCTTCCAGGTCACTGCAGGGAACCTC<br>CACCATGGGAAAATGAAGCCACAGAGAGAATTTATCATTTCGTGGTGGGGCA<br>GATGGTTTATTATCAGTGCGTCCAGGGATACAGGGCTCTACACAGAGGTCCTG<br>CTGAGAGCGTCTGCAAAATGACCCACGGGAAGACAAGGTGGACCCAGCCCCA<br>GCTCATATGCACAGGTGAAATGGAGACCAGTCAGTTTCCAGGTGAAGAGAAG<br>CCTCAGGCAAGCCCCGAAGGCCGTCCTGAGAGTGAGACTTCCTGCCTCGTCAC<br>AACAACAGATTTTCAAATACAGACAGAAATGGCTGCAACCATGGAGACGTCC<br>ATATTTACAACAGAGTACCAGGTAGCAGTGGCCGGCTGTGTTTTCCTGCTGAT<br>CAGCGTCCTCCTCCTGAGTGGGCTCACCTGGCAGCGGAGACAGAGGAAGAGT<br>AGAAGAACAATCTAGTCTAGAGGATCCCGGGTGGCATCCCTGTGACCCCTCCC<br>CAGTGCCTCTCCTGGCCCTGGAAGTTGCCACTCCAGTGCCCACCAGCCTTGTCC<br>TAATAAAATTAAGTTGCATCATTTTGTCTGACTAGGTGTCCTTCTATATATTAT<br>GGGGTGGAGGGGGGKGKGGWWWKGRRSCAAGGGGCAAGTTGGGAAGAMAC<br>CTGTAGGGCCTGCGGGTYTATTGGGAACCAAGCTGGAGTGCAGKGCACATCT<br>GGCTCMCTGCATCTCCGCCTCCTGGGTCAGCGATCTCCTGCCTCAGCCTCCCG<br>AGTTGTGGGATTCAGGCATGCATGACAGGCTCAGCTATTTTTGTTTTTTGTARR<br>ACGGTTTCACCATATTGGCAGCTGGTCTCCACTCCTATYYCAGGKGATCTACC<br>CACCTTGGCCTCCAAA |

What is claimed is:

1. A genetically modified cell comprising a deletion of the Susd2 gene or a fragment thereof, wherein interaction between SUSD2 and IL-2Rα is disrupted.

2. The cell of claim 1, wherein the cell comprises a complete deletion of the Susd2 gene.

3. The cell of claim 1, wherein the cell is a T cell.

4. The cell of claim 3, wherein the T cell is a $CD8^+$ T cell.

5. The cell of claim 1, wherein the cell comprises a chimeric antigen receptor (CAR).

6. A composition comprising the cell of claim 1 and an anticancer agent.

7. The composition of claim 6, wherein the anticancer agent is an immunotherapeutic agent.

8. The composition of claim 7, wherein the immunotherapeutic agent comprises an anti-PD-L1 antibody.

9. The composition of claim 7, wherein the immunotherapeutic agent comprises an anti-PD-1 antibody.

10. A method of treating a cancer comprising administering to a subject a genetically modified cell comprising a deletion of the SUSD2 Susd2 gene or a fragment thereof.

11. The method of claim 10, wherein the cell comprises a complete deletion of the Susd2 gene.

12. The method of claim 10, wherein the cell is a T cell.

13. The method of claim 12, wherein the T cell is a $CD8^+$ T cell.

14. The method of claim 10, wherein the cell comprises a chimeric antigen receptor (CAR).

15. The method of claim 10, wherein the subject is further administered an anticancer agent.

16. The method of claim 10, wherein the subject is further administered an immunotherapeutic agent.

17. The method of claim 10, wherein the subject is further administered an anti-PD-L1 antibody.

18. The method of claim 10, wherein the subject is further administered an anti-PD-1 antibody.

19. The method of claim 10, wherein the subject is further administered an anti-CTLA-4 antibody.

20. The method of claim 10, wherein the cancer is a colon adenocarcinoma.

21. The method of claim 10, wherein the cancer is a lymphoma.

* * * * *

SEQUENCE LISTING

```
Sequence total quantity: 34
SEQ ID NO: 1           moltype = AA  length = 820
FEATURE                Location/Qualifiers
source                 1..820
                       mol_type = protein
                       organism = synthetic construct
SEQUENCE: 1
MKLALLPWIL MLLSTIPGPG FTAGAQGSCS LRCGAQDGLC SCHPTCSGLG TCCEDFLDYC  60
LEILPSSGSM MGGKDFVVQH LKWTDPTDGV ICRFKESIQT LGYVDDFYQV HCISPLLYES  120
GYIPFTISMD NGRSFPHAGT WLAAHPYKVS ESEKSQLVNE THWQYYGTSD TRGNLNLTWD  180
TSALPTPAVT IELWGYEETG KPYSGNWTSK WSYLYPLATN IPNTGFFTFT PKPASPQYQR  240
WKVGALRISS SRNYPGEKDV RALWTNDHAL AWHLGDDFRA DSVAWARAQC LAWEALEDQL  300
PNFLTELPDC PCTLAQARAD SGRFFTDYGC DIEHGSVCTY HPGAVHCVRS VQASPRYGSG  360
QQCCYTAAGT QLLTSDSTSG STPDRGHDWG APPYRTPPRV PGMSHWLYDV ISFYYCCLWA  420
PECPRYMKRR PSSDCRNYRP PRLASAFGDP HFVTFDGTSF SFSGNGEYVL LETTLSDLRV  480
QGRAQPGRMP NGTQARGTGL TAVAVQEDNS DVIEVRLAGG SRVLEVLLNQ KVLSFTEQNW  540
MDLKGMFLSV AAQDKVSIML SSGAGLEVGV QGPFLSVSIL LPEKFLTHTR GLLGTLNNNP  600
RDDFTLRNGQ VLPLNASAQQ VFQFGADWAV SNTSSLFTYD SWLLVYQFVY GPKHNPNFKP  660
LFPDETTLSP SQTEDVARLC EGDRFCILDV MSTGSSSVGN ATRIAHQLHQ HRLKSLQPVV  720
SCGWLPPPAN GHKEGLRYLE GSVVRFSCNN GYSLVGPESS TCQADGKWSM PTPECQPGRS  780
YTVLLSIIFG GLAIVALISI IYMMLHRRRK SNMTMWSSQP                       820

SEQ ID NO: 2           moltype = AA  length = 822
FEATURE                Location/Qualifiers
```

```
source                    1..822
                          mol_type = protein
                          organism = synthetic construct
SEQUENCE: 2
MKPALLPWAL LLLATALGPG PGPTADAQES CSMRCGALDG PCSCHPTCSG LGTCCLDFRD  60
FCLEILPYSG SMMGGKDFVV RHFKMSSPTD ASVICRFKDS IQTLGHVDSS GQVHCVSPLL  120
YESGRIPFTV SLDNGHSFPR AGTWLAVHPN KVSMMEKSEL VNETRWQYYG TANTSGNLSL  180
TWHVKSLPTQ TITIELWGYE ETGMPYSQEW TAKWSYLYPL ATHIPNSGSF TFTPKPAPPS  240
YQRWRVGALR IIDSKNYAGQ KDVQALWTND HALAWHLSDD FREDPVAWAR TQCQAWEELE  300
DQLPNFLEEL PDCPCTLTQA RADSGRFFTD YGCDMEQGSV CTYHPGAVHC VRSVQASLRY  360
GSGQQCCYTA DGTQLLTADS SGGSTPDRGH DWGAPPFRTP PRVPSMSHWL YDVLSFYYCC  420
LWAPDCPRYM QRRPSNDCRN YRPPRLASAF GDPHFVTFDG TNFTFNGRGE YVLLEAALTD  480
LRVQARAQPG TMSNGTETRG TGLTAVAVQE GNSDVVEVRL ANRTGGLEVL LNQEVLSFTE  540
QSWMDLKGMF LSVAAGDRVS IMLASGAGLE VSVQGPFLSV SVLLPEKFLT HTHGLLGTLN  600
NDPTDDFTLH SGRVLPPGTS PQELFLFGAN WTVHNASSLL TYDSWFLVHN FLYQPKHDPT  660
FEPLFPSETT LNPSLAQEAA KLCGDDHFCN FDVAATGSLS TGTATRVAHQ LHQRRMQSLQ  720
PVVSCGWLAP PPNGQKEGNR YLAGSTIYFH CDNGYSLAGA ETSTCQADGT WSSPTPKCQP  780
GRSYAVLLGI IFGGLAVVAA VALVYVLLRR RKGNTHVWGA QP                    822

SEQ ID NO: 3              moltype = DNA  length = 28
FEATURE                   Location/Qualifiers
source                    1..28
                          mol_type = other DNA
                          organism = synthetic construct
SEQUENCE: 3
caacacttct ccatcagtaa cctgcact                                    28

SEQ ID NO: 4              moltype = DNA  length = 27
FEATURE                   Location/Qualifiers
source                    1..27
                          mol_type = other DNA
                          organism = synthetic construct
SEQUENCE: 4
actctaaagc tggctggcta ttcatca                                     27

SEQ ID NO: 5              moltype = DNA  length = 24
FEATURE                   Location/Qualifiers
source                    1..24
                          mol_type = other DNA
                          organism = synthetic construct
SEQUENCE: 5
ctcacggaca gttatggaac cgtg                                        24

SEQ ID NO: 6              moltype = DNA  length = 20
FEATURE                   Location/Qualifiers
source                    1..20
                          mol_type = other DNA
                          organism = synthetic construct
SEQUENCE: 6
agctggagtc acagaaggag                                             20

SEQ ID NO: 7              moltype = DNA  length = 20
FEATURE                   Location/Qualifiers
source                    1..20
                          mol_type = other DNA
                          organism = synthetic construct
SEQUENCE: 7
aggcataacg cactaggttt                                             20

SEQ ID NO: 8              moltype = DNA  length = 20
FEATURE                   Location/Qualifiers
source                    1..20
                          mol_type = other DNA
                          organism = synthetic construct
SEQUENCE: 8
gtcaggttgc ctctgtctca                                             20

SEQ ID NO: 9              moltype = DNA  length = 20
FEATURE                   Location/Qualifiers
source                    1..20
                          mol_type = other DNA
                          organism = synthetic construct
SEQUENCE: 9
tcagggaaga gtctggaaag                                             20

SEQ ID NO: 10             moltype = DNA  length = 20
FEATURE                   Location/Qualifiers
source                    1..20
                          mol_type = other DNA
```

```
                      organism = synthetic construct
SEQUENCE: 10
agggctatgc tctccctcac                                              20

SEQ ID NO: 11         moltype = DNA  length = 20
FEATURE               Location/Qualifiers
source                1..20
                      mol_type = other DNA
                      organism = synthetic construct
SEQUENCE: 11
ctctcagctg tggtggtgaa                                              20

SEQ ID NO: 12         moltype = DNA  length = 20
FEATURE               Location/Qualifiers
source                1..20
                      mol_type = other DNA
                      organism = synthetic construct
SEQUENCE: 12
cattacctga aggccaagga                                              20

SEQ ID NO: 13         moltype = DNA  length = 20
FEATURE               Location/Qualifiers
source                1..20
                      mol_type = other DNA
                      organism = synthetic construct
SEQUENCE: 13
caattgtcca gtcccagagg                                              20

SEQ ID NO: 14         moltype = DNA  length = 22
FEATURE               Location/Qualifiers
source                1..22
                      mol_type = other DNA
                      organism = synthetic construct
SEQUENCE: 14
cgggaacgaa agagaagctc ta                                           22

SEQ ID NO: 15         moltype = DNA  length = 19
FEATURE               Location/Qualifiers
source                1..19
                      mol_type = other DNA
                      organism = synthetic construct
SEQUENCE: 15
ggcgcttgtg gagaaggag                                               19

SEQ ID NO: 16         moltype = DNA  length = 19
FEATURE               Location/Qualifiers
source                1..19
                      mol_type = other DNA
                      organism = synthetic construct
SEQUENCE: 16
gaggccaagc cctggtatg                                               19

SEQ ID NO: 17         moltype = DNA  length = 19
FEATURE               Location/Qualifiers
source                1..19
                      mol_type = other DNA
                      organism = synthetic construct
SEQUENCE: 17
cgggccgatt gatctcagc                                               19

SEQ ID NO: 18         moltype = DNA  length = 20
FEATURE               Location/Qualifiers
source                1..20
                      mol_type = other DNA
                      organism = synthetic construct
SEQUENCE: 18
atgacatcaa gaaggtggtg                                              20

SEQ ID NO: 19         moltype = DNA  length = 20
FEATURE               Location/Qualifiers
source                1..20
                      mol_type = other DNA
                      organism = synthetic construct
SEQUENCE: 19
cataccagga aatgagcttg                                              20

SEQ ID NO: 20         moltype = DNA  length = 29
FEATURE               Location/Qualifiers
source                1..29
```

```
                          mol_type = other DNA
                          organism = synthetic construct
SEQUENCE: 20
gcgaattcaa tgcggccgga gggcgcggg                                   29

SEQ ID NO: 21             moltype = DNA  length = 28
FEATURE                   Location/Qualifiers
source                    1..28
                          mol_type = other DNA
                          organism = synthetic construct
SEQUENCE: 21
gcggatcctc aggtggcctc caggacgg                                    28

SEQ ID NO: 22             moltype = DNA  length = 44
FEATURE                   Location/Qualifiers
source                    1..44
                          mol_type = other DNA
                          organism = synthetic construct
SEQUENCE: 22
ctccagaatc ctgcaatgat agggcgaagt tgagaggccc tttg                  44

SEQ ID NO: 23             moltype = DNA  length = 44
FEATURE                   Location/Qualifiers
source                    1..44
                          mol_type = other DNA
                          organism = synthetic construct
SEQUENCE: 23
caaagggcct ctcaacttcg ccctatcatt gcaggattct ggag                  44

SEQ ID NO: 24             moltype = DNA  length = 43
FEATURE                   Location/Qualifiers
source                    1..43
                          mol_type = other DNA
                          organism = synthetic construct
SEQUENCE: 24
gcgccagcaa atccgcacca ggaacctgct ccccatgtac cag                   43

SEQ ID NO: 25             moltype = DNA  length = 43
FEATURE                   Location/Qualifiers
source                    1..43
                          mol_type = other DNA
                          organism = synthetic construct
SEQUENCE: 25
ctggtacatg gggagcaggt tcctggtgcg gatttgctgg cgc                   43

SEQ ID NO: 26             moltype = DNA  length = 41
FEATURE                   Location/Qualifiers
source                    1..41
                          mol_type = other DNA
                          organism = synthetic construct
SEQUENCE: 26
gcagcacgct gacatctaca ggctgcggat tcgtgttcgt g                     41

SEQ ID NO: 27             moltype = DNA  length = 41
FEATURE                   Location/Qualifiers
source                    1..41
                          mol_type = other DNA
                          organism = synthetic construct
SEQUENCE: 27
cacgaacacg aatccgcagc ctgtagatgt cagcgtgctg c                     41

SEQ ID NO: 28             moltype = DNA  length = 43
FEATURE                   Location/Qualifiers
source                    1..43
                          mol_type = other DNA
                          organism = synthetic construct
SEQUENCE: 28
gactgaccct gattacatca ggcgactgcg gtactgtgag tac                   43

SEQ ID NO: 29             moltype = DNA  length = 43
FEATURE                   Location/Qualifiers
source                    1..43
                          mol_type = other DNA
                          organism = synthetic construct
SEQUENCE: 29
gtactcacag taccgcagtc gcctgatgta atcagggtca gtc                   43

SEQ ID NO: 30             moltype = DNA  length = 43
FEATURE                   Location/Qualifiers
```

-continued

```
source                 1..43
                       mol_type = other DNA
                       organism = synthetic construct
SEQUENCE: 30
ccccagccgg gttctgcgca ggtgggactt cagcaagtac tac                   43

SEQ ID NO: 31          moltype = DNA  length = 43
FEATURE                Location/Qualifiers
source                 1..43
                       mol_type = other DNA
                       organism = synthetic construct
SEQUENCE: 31
gtagtacttg ctgaagtccc acctgcgcag aacccggctg ggg                   43

SEQ ID NO: 32          moltype = DNA  length = 44
FEATURE                Location/Qualifiers
source                 1..44
                       mol_type = other DNA
                       organism = synthetic construct
SEQUENCE: 32
gaatgacctg actgcgacca ggaggggga gctggggccc cggc                   44

SEQ ID NO: 33          moltype = DNA  length = 44
FEATURE                Location/Qualifiers
source                 1..44
                       mol_type = other DNA
                       organism = synthetic construct
SEQUENCE: 33
gccggggccc cagctccccc ctcctggtcg cagtcaggtc attc                  44

SEQ ID NO: 34          moltype = DNA  length = 1377
FEATURE                Location/Qualifiers
source                 1..1377
                       mol_type = other DNA
                       organism = synthetic construct
SEQUENCE: 34
caatgggagc aatagcagag ctcgtttagt gaccgtcaga attaaccatg gactacaaag  60
accatgacgg tgattataaa gatcatgaca tcgattacaa ggatgacgat gacaagcttg  120
cggccgcgaa ttcaatggat tcatacctgc tgatgtgggg actgctcacg ttcatcatgg  180
tgcctggctg ccaggcagag ctctgtgacg atgacccgcc agagatccca cacgccacat  240
tcaaagccat ggcctacaag gaaggaacca tgttgaactg tgaatgcaag agaggtttcc  300
gcagaataaa aagcgggtca ctctatatgc tctgtacagg aaactctagc cactcgtcct  360
gggacaacca atgtcaatgc acaagctctg ccactcggaa cacaacgaaa caagtgacac  420
ctcaacctga agaacagaaa gaaaggaaaa ccacagaaat gcaaagtcca atgcagccag  480
tggaccaagc gagccttcca ggtcactgca gggaacctcc accatgggaa aatgaagcca  540
cagagagaat ttatcatttc gtggtggggc agatggttta ttatcagtgc gtccagggat  600
acagggctct acacagaggt cctgctgaga gcgtctgcaa aatgacccac gggaagacaa  660
ggtggaccca gccccagctc atatgcacag gtgaaatgga gaccagtcag tttccaggtg  720
aagagaagcc tcaggcaagc cccgaaggcc gtcctgagag tgagacttcc tgcctcgtca  780
caacaacaga ttttcaaata cagacagaaa tggctgcaac catggagacg tccatattta  840
caacagagta ccaggtagca gtggccggct gtgttttcct gctgatcagc gtcctcctcc  900
tgagtgggct cacctggcag cggagacaga ggaagagtag aagaacaatc tagtctagag  960
gatcccgggt ggcatccctg tgacccctcc ccagtgcctc tcctggccct ggaagttgcc  1020
actccagtgc ccaccagcct tgtcctaata aaattaagtt gcatcatttt gtctgactag  1080
gtgtccttct atatattatg gggtggaggg gggkgkggww wkgrrscaag gggcaagttg  1140
ggaagamacc tgtagggcct gcgggtytat tgggaaccaa gctggagtgc agkgcacatc  1200
tggctcmctg catctccgcc tcctgggtca gcgatctcct gcctcagcct cccgagttgt  1260
gggattcagg catgcatgac aggctcagct atttttgttt tttgtarrac ggtttcacca  1320
tattggcagc tggtctccac tcctatyyca ggkgatctac ccaccttggc ctccaaa     1377
```